US010718772B2

(12) United States Patent
Navratil et al.

(10) Patent No.: US 10,718,772 B2
(45) Date of Patent: Jul. 21, 2020

(54) METHOD OF DETECTION OF ANALYTE ACTIVE FORMS AND DETERMINATION OF THE ABILITY OF SUBSTANCES TO BIND INTO ANALYTE ACTIVE SITES

(71) Applicant: USTAV ORGANICKE CHEMIE A BIOCHEMIE AKADEMIE VED CR, V.V.I., Prague (CZ)

(72) Inventors: Vaclav Navratil, Prague (CZ); Pavel Sacha, Prague (CZ); Jiri Schimer, Prague (CZ); Jan Konvalinka, Prague (CZ); Pavel Majer, Prague (CZ)

(73) Assignee: USTAV ORGANICKE CHEMIE A BIOCHEMIE AKADEMIE VED CR, V.V.I. (CZ)

( * ) Notice: Subject to any disclaimer, the term of this patent is extended or adjusted under 35 U.S.C. 154(b) by 201 days.

(21) Appl. No.: 15/500,970

(22) PCT Filed: Aug. 4, 2015

(86) PCT No.: PCT/CZ2015/000084
§ 371 (c)(1),
(2) Date: Feb. 1, 2017

(87) PCT Pub. No.: WO2016/019929
PCT Pub. Date: Feb. 11, 2016

(65) Prior Publication Data
US 2017/0219583 A1 Aug. 3, 2017

(30) Foreign Application Priority Data
Aug. 5, 2014 (CZ) .............................. PV 2014-527

(51) Int. Cl.
C12P 19/34 (2006.01)
G01N 33/573 (2006.01)
C12Q 1/6804 (2018.01)
G01N 33/58 (2006.01)
G01N 33/543 (2006.01)

(52) U.S. Cl.
CPC ......... G01N 33/573 (2013.01); C12Q 1/6804 (2013.01); C12Y 302/01018 (2013.01); C12Y 304/17021 (2013.01); C12Y 304/23005 (2013.01); C12Y 304/23016 (2013.01); C12Y 402/01001 (2013.01); G01N 33/54306 (2013.01); G01N 33/54353 (2013.01); G01N 33/58 (2013.01); G01N 2333/924 (2013.01); G01N 2333/948 (2013.01); G01N 2333/9513 (2013.01); G01N 2333/96472 (2013.01); G01N 2333/988 (2013.01)

(58) Field of Classification Search
CPC ............ C12Q 1/6804; C12Q 2527/127; C12Q 2537/161; C12Y 302/01018; C12Y 304/17021; C12Y 304/23005; C12Y 304/23016; C12Y 402/01001; G01N 2333/924; G01N 2333/948; G01N 2333/9513; G01N 2333/96472; G01N 2333/988; G01N 33/54306; G01N 33/54353; G01N 33/573; G01N 33/58
See application file for complete search history.

(56) References Cited

U.S. PATENT DOCUMENTS

| 5,770,176 A | 6/1998 | Nargessi |
| 2007/0003950 A1 | 1/2007 | Shen et al. |
| 2008/0085508 A1* | 4/2008 | Wei ................. G01N 33/54346 435/5 |
| 2010/0075307 A1* | 3/2010 | Belyaev .............. C12Q 1/6804 435/6.1 |
| 2010/0151472 A1 | 6/2010 | Nolan et al. |

FOREIGN PATENT DOCUMENTS

| EP | 0544212 A1 | 6/1993 |
| EP | 0625211 B1 | 10/1999 |
| EP | 2189539 A1 | 5/2010 |
| EP | 2189539 B1 | 5/2010 |
| EP | 2189539 B2 | 5/2010 |
| WO | WO-94/29329 A1 | 12/1994 |
| WO | WO-97/32214 A1 | 9/1997 |
| WO | WO-00/24913 A2 | 5/2000 |
| WO | WO-00/24913 A3 | 5/2000 |
| WO | 0216635 A2 | 2/2002 |
| WO | 03058240 A2 | 7/2003 |
| WO | 03083435 A2 | 10/2003 |
| WO | 2006130669 A2 | 12/2006 |

(Continued)

OTHER PUBLICATIONS

Adak et al., ACS applied Materials and Interfaces, 6, 10452-10460, Jun. 2014.*
Hao et al., Mol. Pharm, 10(8): 2975-2985, Aug. 2013.*
He et al., Jounral of Nanobiotechnolgy, 10: 26, 1-17, (Year: 2012).*
Leung K., Molecular Imaging and Contrast Agent Database (MICAD) [Internet]. Bethesda (MD): National Center for Biotechnology Information (US); pp. 1-5; www.ncbi.nlm.nih.gov/books/NBK84431/?report=printable, Mar. 2012.*

(Continued)

Primary Examiner — Cynthia B Wilder
(74) Attorney, Agent, or Firm — Mintz, Levin, Cohn, Ferris, Glovsky and Popeo, P.C.

(57) ABSTRACT

A method for detection of active form of analytes in a sample and/or for determination of ability of tested substances to bind to the active site of these analytes has the following steps: a) analyte or group of analytes from the sample is immobilized on the surface of a solid carrier; b) analyte or group of analytes is incubated with a detection probe; c) then the solid carrier is washed to remove unbound detection probe; and subsequently, the amount of bound detection probe is determined.

60 Claims, 10 Drawing Sheets
Specification includes a Sequence Listing.

(56) References Cited

FOREIGN PATENT DOCUMENTS

WO    WO-2007/005991 A1    1/2007
WO    WO-2012/078534 A1    6/2012

OTHER PUBLICATIONS

Nong et al., Nature Protocols, 8(6), 1234-1248, May 2013.*
International Search Report and Written Opinion of corresponding PCT/CZ2015/000084, dated Feb. 10, 2016.
Alquicer. G. et al. (Sep. 2012, e-published Jun. 29, 2012). "Development of a high-throughput fluorescence polarization assay to identify novel ligands of glutamate carboxypeptidase II," *J Biomol Screen* 17(8):1030-1040.
Anonymous. "Antibody Basics," located at <https://www.sigmaaldrich.com/technical-documents/articles/biology/antibody-basics.html> last visited Nov. 21, 2019, 5 pages.
Bachovchin, D.A. et al. (Aug. 2014, e-published Jul. 6, 2014). "A high-throughput, multiplexed assay for superfamily-wide profiling of enzyme activity," *Nat Chem Biol* 10(8):656-663.
Barinka, C. et al. (Feb. 2002). "Substrate specificity, inhibition and enzymological analysis of recombinant human glutamate carboxypeptidase II," *J Neurochem* 80(3):477-487.
Gad, H. et al. (Apr. 10, 2014, e-published Apr. 2, 2014). "MTH1 inhibition eradicates cancer by preventing sanitation of the dNTP pool," *Nature* 508(7495):215-221.

Hendrickson, E.R. et al. (Feb. 11, 1995). "High sensitivity multianalyte immunoassay using covalent DNA-labeled antibodies and polymerase chain reaction," *Nucleic Acids Res* 23(3):522-529.
Henry, N. et al. (Mar. 2009). "Inappropriate treatment of prostate cancer caused by heterophilic antibody interference," *Nat Clin Pract Urol* 6(3):164-167.
Inglese, J. et al. (Aug. 2007). "High-throughput screening assays for the identification of chemical probes," *Nat Chem Biol* 3(8):466-479.
Lepor, H. et al. (Jun. 2012, e-published Oct. 12, 2011). "Clinical evaluation of a novel method for the measurement of prostate-specific antigen, AccuPSA(TM) as a predictor of 5-year biochemical recurrence-free survival after radical prostatectomy: results of a pilot study," *BJU Int* 109(12):1770-1775.
Loeb, S. et al. (May 2009). "Investigation of human anti-mouse antibodies as potential cause of postprostatectomy PSA elevation," *Urology* 73(5):947-949.
Navrátil, V. et al. (Jan. 25, 2017, e-published Sep. 26, 2016). "DNA-linked Inhibitor Antibody Assay (DIANA) for sensitive and selective enzyme detection and inhibitor screening," *Nucleic Acids Res* 45(2):e10, with Supplementary Information 43 pages.
Preissner, C.M. et al. (Jan. 2005). "Prevalence of heterophilic antibody interference in eight automated tumor marker immunoassays," *Clin Chem* 51(1):208-210.
Ruzicka, V. et al. (Apr. 30, 1993). "Immuno-PCR with a commercially available avidin system," *Science* 260(5108):698-699.
Zhou, H. et al. (Dec. 25, 1993). "Universal immuno-PCR for ultra-sensitive target protein detection," *Nucleic Acids Res* 21(25):6038-6039.

* cited by examiner

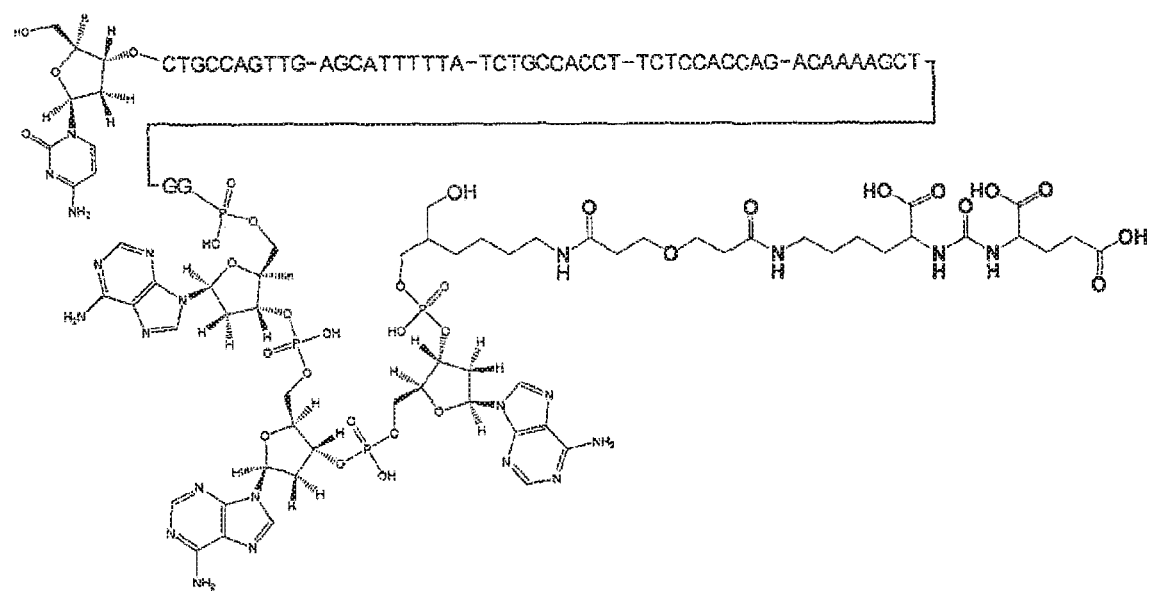
Fig. 5    SEQ ID NO: 1
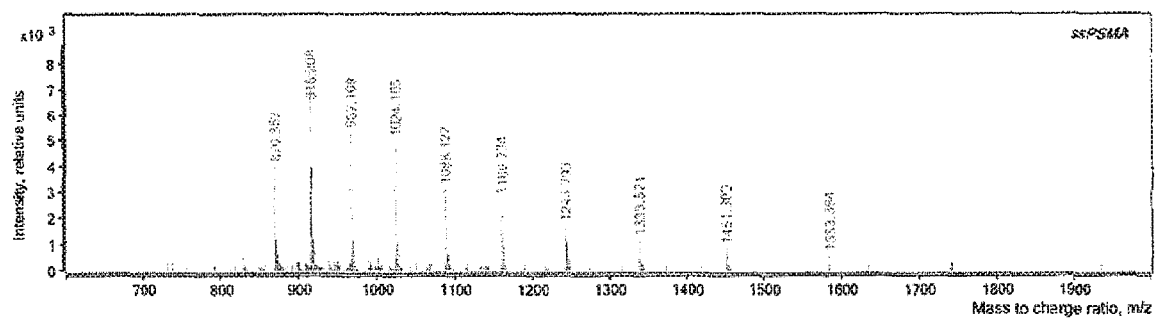
Fig. 6

SEQ ID NO: 4

SEQ ID NO: 1

METHOD OF DETECTION OF ANALYTE ACTIVE FORMS AND DETERMINATION OF THE ABILITY OF SUBSTANCES TO BIND INTO ANALYTE ACTIVE SITES

FIELD OF THE INVENTION

The present invention relates to a method for detecting active form of analytes in a sample and determining the ability of tested substances to bind to the active site of these analytes.

BACKGROUND ART

The present technical solution provides for a sensitive quantification of active forms of analytes, preferably proteins, as well as for a determination of the ability of tested substances to bind to the active sites of these analytes. Therefore, current approaches to solve both these problems are summarized below.

Today's standard for sensitive and specific determination of proteins (antigens) in biological samples is called "Enzyme-Linked Immuno-Sorbent Assay" (abbr. ELISA), and to a limited extent, also "Western Blot" (abbr. WB). Both methods use the possibilities to prepare (monoclonal or polyclonal) antibody selectively binding a given antigen, and the amount of bound antibody, which is proportional to the amount of antigen in the sample, is converted into a measurable signal. Preparation of such antibodies has become a quite routine and commercially available method in the past two decades. The most versatile and widely used method of in vitro diagnostics of today is the so-called "Sandwich ELISA", in which the first antibody is immobilized on a solid carrier, the antigen contained in a biological sample is then bound to the antibody, and after washing, the second detection antibody is bound to the antigen (both antibodies must recognize different epitopes on the same antigen). The detection antibody is conjugated with an enzyme and after repeated washing and addition of substrate, e.g. coloured of luminescent product is produced (depending on the choice of enzyme and substrate) whose amount is proportional to the amount of antigen in the sample. There are several ELISA variants, e.g. fluorophore or radionuclide can be conjugated with the detection antibody instead of an enzyme.

For example, prostate specific antigen (abbr. PSA) can be detected at a concentration of 0.008 ng/ml serum using "ultrasensitive" sandwich ELISA (Abbott Diagnostics). Quantification of PSA in the blood serum is now routinely used for the screening of male population for prostate cancer and in particular for monitoring the patient's response to treatment (Catalona et al. 1991, N Engl J Med, p. 1156; Stamey et al. 1987, N Engl J Med, p. 909). The only definitive treatment of prostate cancer is prostate removal; after this procedure PSA disappears from the blood. If surgery fails to remove all tumour tissue, after some time, the concentration of PSA rises again to the detectable limit. After the surgery, over a period of months to years, PSA levels are below the detection limit of today's methods; therefore more sensitive methods could determine the exact prognosis much earlier than existing methods (Lepor et al. 2012, Bju International, p. 1770).

The very sensitive test using ELISA is generally restricted by the presence of so-called interfering heterophilic antibodies in the blood. These may recognize the sandwich antibodies and thereby connect them without the presence of antigen, which leads to false positive results even in such established methods like the quantification of PSA (Henry et al. 2009, Nature Clinical Practice Urology, p. 164; Preissner et al. 2005, Clinical Chemistry, p. 208). Therefore, to reach at least partial removal of such antibodies, it is sometimes necessary to include additional steps in the processing of blood (de Jager et al. 2005, J. Immunol Methods, p. 124), for which a commercial product is used (Scantibodies). It is also appropriate to include controls for measuring the extent of the interference (Bjerner et al. 2005, Clinical Chemistry, p. 9). Commercial kits for the measurement of PSA normally contain blocking agents, which should help to avoid the effects of interfering antibodies; or the two sandwich antibodies do not originate from the same organism, but even so completely reliable results are not secured (Loeb et al. 2009; Preissner et al. 2005, see above).

It is desirable to further increase the sensitivity of today's ELISA methods, in particular for the above mentioned determination of PSA. Due to high expression of PSA in prostate tissue it can be assumed that there will be a number of tumour markers in the blood in substantially lower concentrations than the concentration of PSA, especially in the early stages of the disease. Furthermore, if antibodies as sensitive as antibodies against PSA are not available against a given antigen, the sensitivity of ELISA decreases substantially. Generally, more sensitive detection would be beneficial also for early detection of viral diseases (HIV) or reliable diagnosis of certain bacterial infections (Lyme disease). Increased sensitivity of up to two orders of magnitude while maintaining a simple ELISA format can usually be achieved by conjugating the detection antibody with an oligonucleotide, which is then quantified by the real-time polymerase chain reaction, i.e. quantitative PCR (qPCR for short). Deoxyribonucleic acid (hereinafter DNA) can be conjugated with the antibody by non-covalent interactions of biotin with streptavidin to be used in method called universal immuno-PCR, abbr. iPCR (Ruzicka et al. 1993, Science, p. 698; Zhou et al. 1993, Nucleic Acids Research, p. 6038; EP 2189539) or by covalent bond formed by chemical agents that are commercially available (e.g. Solulink) to be used in method called direct iPCR (Hendrickson et al. 1995, Nucleic Acids Research, p. 522; EP 0544212; EP 0625211). Despite the high sensitivity of iPCR in laboratory conditions, however, a comparable sensitivity cannot be expected when applied in clinical practice, because the iPCR (like sandwich ELISA) is prone to erroneous results caused by the presence of interfering antibodies in the biological matrices, especially in serum and plasma. New ultrasensitive methods applicable without limitation for determination in biological matrices are therefore still needed. Currently used high-throughput screening (HTS) assays for enzyme inhibitors are mostly based on quantification of either substrate/product or displacement of active site probe by the tested substances (Inglese et al. 2007, Nature Chemical Biology, p. 466). Example of the first type of assay would be absorbance measurement of coloured product originating from reaction of malachite green and phosphate, which is liberated by the action of phosphorylases (Gad et al. 2014, Nature, p. 215). The most versatile assays utilize active site probes and detect their displacement from the active site by the tested substances. Typical readouts in these assays are fluorescence or fluorescence polarisation and the measured property differs between bound and unbound state of the probe which makes possible to discriminate between these two states (Inglese et al. 2007, Nature Chemical Biology, p. 466). Despite the high versatility of these assays, they often suffer from low sensitivity of the detection, which requires the use of high probe and enzyme amounts (Alquicer et al. 2012, J Biomol Screen, p. 1030). Consequently, these assays may tend to produce a lot of false negative results, because weaker inhibitors are not able to displace the probe, which is used in a concentration highly above its $K_d$. For example, if the working probe concentration is 20 times above its $K_d$ and positive result is reported after 50% decline in the fluorescence polarization, only inhibitors with $K_i$ below 50 $nmol \cdot l^{-1}$ are detected if 1 $\mu mol \cdot l^{-1}$ concentration of tested substances is used. Moreover, the signal to background ratio is typically not higher than one order of magnitude and thus only qualitative information about the binding of tested substances is obtained (Inglese et al. 2007, Nature Chemical Biology, p. 466; Gad et al. 2014, Nature, p. 215). Additional issue of these assays is the inability to accurately screen fluorescent or coloured substances since they interfere with assay readout.

Prostate Specific Membrane antigen (PSMA, also known as GCPII) and Carbonic Anhydrase IX (CA-IX) are both enzymes and are known to be markers of certain types of cancer with possible use as diagnostic and prognostic markers which is limited by the lack of accurate and sensitive bioanalytical methods for their quantification (Barve et al. 2014, Journal of Controlled Release, p. 118; Hyrsl et al. 2009, Neoplasma, p. 298). Both proteins are also targets of drug development campaigns. Drugs consisting of toxin conjugated to small molecular inhibitor of both proteins are under evaluation in clinical and preclinical trials with promising results (Haberkorn et al. 2015, Ann Oncol 26, p. ii33; Krall et al. 2014, Angewandte Chemie-International Edition, p. 4231). Additionally, the inhibition of GCPII is beneficial in animal models of several neuropathies (Barinka et al. 2012, Current Medicinal Chemistry, p. 856), whereas the inhibition of CA-IX has suppressive effects on tumor growth in several animal models (Lock et al. 2013, Oncogene, p. 5210). Despite the promising results, better inhibitors for both proteins are still needed as known compounds exhibit several important adverse effects. More specifically, the current GCPII inhibitors are multiply charged and cannot effectively penetrate the blood brain barrier to reach their intended target organ, whereas known CA-IX inhibitors are sulphonamides with unfavorable pharmacological profiles (Supuran 2008, Nature Reviews Drug Discovery, p. 168). The discovery of novel scaffolds inhibiting these enzymes is strongly limited by the absence of accurate screening methods, the only developed assay for GCPII HTS of inhibitors suffers of low sensitivity (Alquicer et al. 2012, J Biomol Screen, p. 1030) and no HTS of inhibitors is available for CA-IX. On the basis of the present invention we were able to develop currently the most sensitive assays for quantification of both enzymes in complex biological matrices as well as first assays for sensitive and accurate screening of inhibitors of both enzymes.

DISCLOSURE OF THE INVENTION

The invention provides a method for detecting active form of analytes and/or determining the ability of tested substances to bind to active sites of analytes, wherein the analyte is immobilized on a solid carrier, preferably selectively through a binding molecule; and a detection probe is selectively bound to the analyte. The detection probe consists of a compound for selective binding to the active site of the analyte (ligand portion), preferably of molecular weight less than 2500 Da, more preferably less than 1000 Da, and a DNA template for the polymerase chain reaction (oligonucleotide tag), covalently bound by a chemical linker. After washing the unbound probe away, the amount of the bound probe is determined, which is directly proportional to the amount of immobilized analyte; preferably the determination is performed by detection of oligonucleotide tags in quantitative polymerase chain reaction (qPCR). The probe can also be incubated with immobilized analyte in the presence of a tested substance potentially binding to the active site of the analyte, or a mixture of such substances. The ability of the tested substance or mixture of tested substances to bind to the active site of the analyte is determined by comparing the amount of bound detection probe after the incubation in the presence and in the absence of a tested substance or mixture of tested substances.

The invention thus provides a method for detecting active form of analytes in the sample and/or determining ability of tested substances to bind to the active sites of these analytes, comprising the following steps:

a) analyte or group of analytes from a sample is immobilized on the surface of a solid carrier either by non-specific non-covalent adsorption or by covalent binding of surface functional groups of the analyte and corresponding functional groups on the solid carrier, or preferably via a binding molecule which is bound to the surface of the solid carrier beforehand and is capable of selectively binding the analyte or group of analytes contained in the sample during incubation of the solid carrier with the sample;

b) the analyte or group of analytes is incubated with a detection probe which binds selectively to the analyte or group of analytes via a compound for selective binding to the analyte active site; wherein the probe consists of a low molecular compound having a molecular weight of up to 2500 Da for selective binding to the analyte active site;

an oligonucleotide tag, optionally with a covalently attached fluorophore, biotin or a chemical group, and a chemical linker covalently linking the compound for selective binding to the analyte active site and the oligonucleotide tag; and optionally, the incubation is carried out in the presence of various concentrations of a tested substance, whose ability to bind to the active site is to be tested, or a mixture of such substances;

c) then the solid carrier is washed to remove the unbound detection probe;

d) subsequently, the amount of the bound detection probe is determined, either directly on the solid carrier or after releasing, whereas this amount is directly proportional to the amount of the analyte or group of analytes in the tested sample, whereas preferably, in step b) incubating the detection probe with a solid carrier, or in step a) incubating the sample with a solid carrier, at least one additive selected from the group comprising ionic detergents, nonionic detergents, casein and therefrom prepared casein blocking agents, serum albumin, DNA, and immunoglobulins, is added to the incubated solution.

In a preferred embodiment of the herein disclosed method for detecting active form of analytes in the sample and/or determining ability of tested substances to bind to the active sites of these analytes, before performing step a), the incubation of the tested sample containing the analyte or group of analytes is first incubated with the detection probe according to step b), and after step a), steps c) and d) are performed.

In another preferred embodiment of the herein described method, the steps are performed in the order a), b), c), d).

In a preferred embodiment according to the invention the analyte is selected from the group comprising enzyme or group of enzymes wherein the compound for selective binding to the active site is a selective inhibitor of the enzyme or group of enzymes; receptor or group of receptors wherein the compound for selective binding to the active site is a selective agonist or antagonist of the receptor or receptor groups; and a transporter or group of transporters wherein a compound for selective binding to the active site is a substance capable of selective binding to the transporter or group of transporters in the binding site for transported molecules.

Preferably, the oligonucleotide tag is a single stranded or double stranded DNA, optionally with one or more modifying groups selected from the group consisting of a fluorophore, biotin or a chemically reactive group, covalently attached through an additional chemical linker to a defined site of one or both strands of the oligonucleotide tag.

A substance potentially binding to the active site of the analyte is the tested substance.

In one embodiment the detection probe includes two or more molecules of the same compound for selective binding to the active site of the analyte, each individually covalently linked via a chemical linker into different positions of oligonucleotide tag.

A conjugate of the detection probe as described above, consisting of four molecules of the probe with attached biotin, and of avidin, neutravidin or streptavidin, to which fluorophores or enzymes are optionally covalently attached (see FIG. 2D), can be used for the detection.

In another preferred embodiment of the method according to the invention, the amount of the bound detection probe is determined by quantitative polymerase chain reaction, fluorescence or through coupled enzyme reactions spectrophotometrically or chemiluminescently.

In the preferred embodiment of the method according to the invention, the binding molecule capable of selectively binding to the analyte in the sample is selected from the group consisting of antibodies or their fragments, protein molecules mimicking antibodies such as affibodies, anticalins or designed ankyrin repeat proteins, and lectins, avidin, neutravidin, streptavidin, oligopeptides, and chelating agents.

In another preferred embodiment of the method according to the invention, in the step a), selective binding of the analyte or group of analytes to a binding molecule immobilized on the solid carrier is mediated by hapten, biotin, a universal epitope or affinity or purification tag, which is covalently attached to the analyte or group of analytes.

In another preferred embodiment of the method according to the invention, complex biological matrix, optionally containing interfering antibodies, selected from the group consisting of blood, blood plasma, blood serum, cerebrospinal fluid, urine, bacterial, yeast, tissue or cell lysate, conditioned bacterial, yeast or cell culture medium, synovial fluid, amniotic fluid, ascites, pleural fluid, pericardial fluid, stool extract, saliva, sweat and seminal plasma can be used as a sample.

In a preferred embodiment, the ability of the tested substance or mixture of such substances to bind to the active site of the analyte is determined from the difference in the amount of bound detection probe after incubation without tested substance and after incubation with the tested substance.

More preferably the ability of the tested substance to bind to the active site of the analyte is determined as the value of binding constant (for binding of the substance into the active site of analyte) from the difference of the amounts of bound detection probe after incubation without tested substance and after incubation with only a single concentration of tested substance.

In another preferred embodiment of the method according to the invention, human prostate specific membrane antigen, also known as glutamate carboxypeptidase II, is used as the analyte, and inhibitor of human prostate specific membrane antigen as a compound for selective binding; or human glutamate carboxypeptidase III is used as an analyte and inhibitor of human glutamate carboxypeptidase III as a compound for selective binding; or human prostate specific antigen is used as an analyte and the inhibitor of human prostate specific antigen as a compound for selective binding; or human carbonic anhydrase IX is used as an analyte and inhibitor of human carbonic anhydrase IX as a compound for selective binding; or human carbonic anhydrase XII is used as an analyte and inhibitor of human carbonic anhydrase XII as a compound for selective binding; or human influenza neuraminidase is used as an analyte and inhibitor of human influenza neuraminidase as a compound for selective binding; or human fibroblast-activating protein is used as an analyte and inhibitor of human fibroblast-activating protein as a compound for selective binding; or human dipeptidyl peptidase 4 known also as CD26 is used as an analyte and inhibitor of dipeptidyl peptidase 4 as a compound for selective binding.

The described method of determining typically proceeds so that a binding molecule capable of selectively binding the analyte is immobilized on the surface of the selected type of the solid carrier, wherein the analyte may preferably be an enzyme, a receptor or a transporter. Usually, after the immobilization of the binding molecule, the surface of the solid carrier is blocked by agents for suppressing nonspecific adsorption. Subsequently, the solid carrier is incubated with a sample containing the analyte which is selectively bound to the immobilized binding molecule, wherein the sample is typically a complex biological matrix naturally containing the analyte. The solid carrier with the immobilized binding molecule to which the analyte is bound, is then incubated with the detection probe for the selective binding of the ligand portion of the probe into the active site of the analyte, and the amount of bound detection probe is quantified after washing preferably by qPCR. Use of a complex sample is enabled by the selectivity of binding of the analyte to the binding molecule, which, unlike non-selective immobilizing, allows effective binding even in the case of minor components of the mixture. The sample may also be a solution with an analyte prepared by recombinant expression. Such analyte (in contrast to a naturally occurring analyte) can contain artificially introduced universal epitope selectively bound by an immobilized binding molecule, specifically chosen for this case.

In another embodiment, a purified analyte is used, either endogenous or recombinantly prepared, and it is immobilized (non-selectively) directly on the surface of the selected type of the solid carrier instead of a binding molecule capable of binding the analyte. This arrangement is especially useful for testing of the ability of the tested substances to bind to the active site of the analyte, as it does not require a binding molecule selectively binding the analyte, which may be hardly available or too expensive for some analytes. If the analyte is immobilized directly to the surface of the solid carrier, such surface is typically subsequently blocked with agents for suppressing nonspecific adsorption and then the solid carrier is incubated with the detection probe for selective binding to the active site of the analyte. The amount of the bound probe is determined, preferably by qPCR, after washing the unbound probe away.

In one aspect of the invention the compound constituting the ligand portion is preferably selected from the group comprising an inhibitor of an enzyme or group of enzymes, antagonist of a transporter or group of transporters and their transported substance, an agonist, a co-agonist, antagonist or blocker of a receptor or group of receptors; analyte is then selected from the group consisting of an enzyme, a group of enzymes, transporter, group of transporters, receptor or group of receptors. Preferably, the said compound for selective binding of the analyte is of an organic character and has the total molecular weight of up to 2500 Da, more preferably up to 1000 Da.

Use of a compound for selective binding to a defined group of analytes—enzymes, receptors or transporters—is preferable for analyte quantification, in which a number of different proteins can be quantified with a single detection probe since it has proved that selectivity between the group members is sufficiently ensured by immobilized binding molecule. Furthermore, it is equally preferable for measuring the ability of tested substances to bind to the active sites of the analyte, as it was proved that it is possible to test the binding effectivity both for the intended objective and possible secondary objectives with a single detection probe prepared. Finally, after the unbound probe is washed away, the amount of the bound probe is determined.

In another aspect of the invention qPCR is used for the detection and quantification of the immobilized oligonucleotide tag and thus of the bound detection probe, leading to very high sensitivity of the determination. For example, for determination of prostate specific membrane antigen (PSMA antigen, distinct from the PSA), the sensitivity of ten attograms was reached, equivalent to tens of protein molecules. This is about a million times smaller than the amount detectable with the current PSMA detection methods. Such a sensitivity of determination of other antigens could allow early detection of certain cancers, e.g. determining the progression of prostate cancer after radical prostatectomy using PSA already mentioned in the introduction. Using qPCR also allows parallel determination of multiple analytes simultaneously since parallel determination of a plurality of nucleotide templates in one mixture is a standard and widespread method. Another major advantage of using qPCR represents a large dynamic range of determining the analyte concentration. It turned out that for the detection of some analytes it reaches as high as six to seven orders of magnitude difference in the concentration of analyte in the original sample, which is three to four orders of magnitude larger than in the case of an ELISA assay. Increasing the range by several orders of magnitude compared to the commonly used conventional ELISA would reduce financial costs, since it would reduce the number of re-evaluations of clinical samples for which the amount of analyte was outside of the range of the detection.

The major limitation of the sensitivity of the described determination method is the non-specific adsorption to the surface of the solid carrier. Another aspect of the invention is that non-specific adsorption of detection probe is preferably suppressed by replacing a single stranded oligonucleotide tag with a double stranded tag. Yet another aspect of the invention is that larger distance of the signal from non-specific background can be achieved by diluting the sample and particularly the detection probe in a solution containing various blocking agents suppressing non-specific adsorption. Such agents are preferably non-ionic and ionic detergents, albumins, and casein preparations.

In another aspect of the invention the selective binding of the detection probe to the active site of the analyte is used for measuring the ability of the tested substances to bind to the active site of the analyte. In this arrangement, the detection probe with the analyte is incubated in the presence of tested substance or mixture of tested substances. If the tested substance binds to the active site of the analyte, the amount of bound probe will decrease as compared to incubation in the absence of the tested substance. It was found that dissociation constant ($K_d$) of the tested substance (which corresponds to inhibition constant ($K_i$) if the analyte is an enzyme) can be calculated from the level of the decrease in binding of the probe and the used concentration of tested substance. Therefore a big dynamic range of the setting is crucial; as the dissociation constant of the tested substance towards the analyte can be calculated in the whole dynamic range of the method from a single concentration of tested substance used for the measurement. This means that in the method range of six orders of magnitude it is possible to quantitatively determine the dissociation constant of the substance in the range of 0.5 mmol·l$^{-1}$ to 0.5 nmol·l$^{-1}$ from the used concentration of tested substance 1 mmol·l$^{-1}$ (and used concentration of detection probe corresponding to its $K_d$) or similarly, dissociation constant of the substance in the range of 0.5 µmol·l$^{-1}$ to 0.5 pmol·l$^{-1}$ can be quantitatively determined from the used concentration of tested substance 1 µmol·l$^{-1}$. As shown below, the range of measurable $K_d$ can be changed not only by changing the concentration of the tested substance, but also varying the concentration of the detection probe.

Unlike current methods, the described method thus enables a quantitative screening of substances binding to the active sites of enzymes, receptors and transporters, in which from each particular well of a microplate an accurate $K_d$ of particular tested substance is determined. Obtaining quantitative information about the inhibitory constant of tested substances in this way is much more effective than the frequently used enzyme kinetics, where it is necessary to measure the whole concentration range of the tested substance to determine its inhibition constant. The reason is the substantially lower dynamic range of commonly used determinations of substrates or products of reactions.

The extreme sensitivity of the proposed method also brings further advantages in determining inhibition constants—the efficiency of inhibition is measured with very small amounts of analyte, which is advantageous in particular for membrane proteins and other proteins difficult to prepare. Surprisingly it was also found that the sensitivity and selectivity of the determination is so high that e.g. blood plasma can be used for the screening of inhibitors, even for quite minor proteins, with the consumption of fractions of one µl for one tested substance. PSMA is an example of a minor protein which is usually found at concentrations below 1 ng·ml$^{-1}$ plasma. For comparison, serum albumin concentration ranges from 35 to 50 mg·ml$^{-1}$ plasma and is therefore nearly eight orders of magnitude higher.

Use of a biological material naturally containing an active form of the analyte has not only the advantage that difficult recombinant preparation of the analyte is not necessary, but is also applicable in so called personalized medicine. This includes e.g. measuring the resistance of the viral proteins against a drug in blood of infected patients, or determining binding affinity of drugs on the patient's cytochrome P-450 oxidases and thereby predicting the degradation rate of the drug in the patient. Another significant advantage of the proposed method is the fact that the use of a solid carrier and the possibility of removing the excess tested substance by washing make the method insensitive to erroneous results due to the fluorescence of tested substances. This is fundamentally different from e.g. methods using fluorescence polarization and consequently allows very efficient search for active substances binding to the active sites of enzymes, receptors and transporters in unpurified mixtures of substances obtained by extraction from plants or fungi, since the colour or fluorescence of said mixture does not mean any limitation to the proposed method.

In this application, the solid carrier represents a matrix for the immobilization of binding molecule capable of selectively binding the analyte, or for the direct immobilization of analyte. The solid carrier allows easy removal of excess chemicals by washing, especially the unbound detection probe, and subsequent selective determination of the amount of bound probe, similarly as in the commonly used immunoassay methods of ELISA. Likewise, it allows substitution of solutions used for immobilization of binding molecule, for binding of analyte and detection probe, and for detecting oligonucleotide tag of detection probe, preferably by qPCR.

The material of the solid carrier is selected from the group consisting of polyethylene, polypropylene, poly(4-methylbutene), polystyrene, polymethacrylate, poly(ethylene terephthalate), nylon, poly(vinyl butyrate), sepharose, sephadex, glass, ceramics, metal and metal oxides. To facilitate the covalent attachment of binding molecules or analyte, the surface of the solid carrier may be further functionalized, preferably it may contain chloromethyl, tosyl, mesyl, azide, alkyne, carboxylic, aldehyde, ketone, hydroxyl, sulfhydryl, epoxy or amino groups.

Type of the solid carrier is selected from the group consisting of microplate well surface, microparticles having a diameter typically from 100 nm to 400 μm or a specific place ("spot") on the surface of a microchip. A method of removing unbound chemicals with washing comprises removing the liquid phase, the liquid phase decantation, filtration, magnetic separation followed by removing the supernatant and centrifugation with subsequent removal of the supernatant.

Another feature of the invention is that preferably a binding molecule capable of selectively binding the analyte is first immobilized on the solid carrier; the binding molecule is selected from the group consisting of antibodies and their fragments Fab, F(ab')2, ScFv, Fv; then antibodies consisting only of a heavy chain and their fragments consisting of a single domain (single domain antibody, VHH), combinatorially prepared protein molecules mimicking antibodies (such as affibodies, anticalins, designed ankyrin repeat proteins), lectins, avidin, neutravidin, streptavidin, oligopeptides, and chelating agents (such as trisnitrilotriacetic acid for immobilization of his-tagged proteins).

The binding molecule is preferably immobilized by non-specific non-covalent adsorption, preferably directly to the polystyrene or polypropylene surface of microplate wells or multiwell PCR plates. Binding molecules capable of selectively binding the analyte are preferably also covalently immobilized to the surface of the solid carrier. A proteinaceous binding molecule is immobilized by reaction of its surface groups, which include a primary amine, a thiol (sulfhydryl), carboxyl, aldehyde, ketone and hydroxyl. The reaction takes place directly with reactive or activated groups present on the surface of a solid carrier selected from the group consisting of epoxy, chloromethyl, tosyl, mesyl, azide, alkyne, activated carboxyl, aldehyde, ketone, hydroxyl, sulfhydryl, or amino groups. Solid carriers having activated groups on the surface are commercially available (Invitrogen, PolyMicrospheres).

Immobilization may also be performed through a heterobifunctional coupling reagent; its one reactive group reacts with a corresponding group on the surface of the binding molecule and the second reactive group reacts with a corresponding group on the surface of the solid carrier. Most universally the covalent attachment to a solid carrier is reached by introducing bioorthogonal reactive pairs of groups on the surface of the binding molecule and the solid carrier. Many of the required reagents are commercially available, e.g. from companies Solulink, Click Chemistry Tools, Jena Bioscience, Sigma Aldrich. Couples of bioorthogonal groups are the same as those that are used for coupling the ligand and the oligonucleotide portion of the probe.

For selective immobilization of binding molecule capable of selectively binding the analyte, suitably treated surface of the solid carrier is preferably used, in particular if the binding molecule loses its activity after direct adsorption to the surface. Preferably, a surface with an immobilized biotin-binding component is used, and a binding molecule is surface biotinylated, for example using commercially available NHS-biotin esters (Pierce). Similarly, the binding molecule can be selectively immobilized on a suitably chosen surface through a selected universal epitope. Preferably peptide and protein tags are used, selected from the group consisting of His-tag, Strep-tag, Avi-tag, Flag-tag, GST-tag. Antibody can be preferably bound to a surface with non-specifically immobilized antibody or another compound selectively recognizing a given class of antibodies.

After immobilization of binding molecules capable of selectively binding the analyte, nonspecific adsorption to the surface of the solid carrier is prevented in the next step by incubation with a blocking solution. The blocking solution preferably contains agents selected from the group consisting of albumins, casein, casein blocking agents, nucleic acids, and immunoglobulins.

The solid carrier with the immobilized binding molecule capable of selectively binding the analyte is then incubated with the sample. Selective binding of the analyte allows binding of the analyte from the complex mixtures, where the analyte is a minor component. Monoclonal or polyclonal antibody or their fragments selectively recognizing the analyte are preferably used as the binding molecule for this purpose. High affinity of the antibody towards the analyte allows highly sensitive detection, since majority of molecules of the analyte from a complex matrix binds to the antibody, and moreover, it is not released when washing the solid carrier, especially when washing away the unbound probe. In the method according to the invention, complex biological matrix (optionally containing an interfering antibody) selected from the group consisting of blood, blood plasma, blood serum, cerebrospinal fluid, urine, tissue or cell lysate, synovial fluid, amniotic fluid, ascites, pleural fluid, pericardial fluid, feces extract, saliva, sweat and seminal plasma can be used as a sample.

It was also tested that in contrast to the currently used immunological methods based on sandwich antibodies for analyte quantification, such as sandwich ELISA or immuno-PCR, our method of quantification is not sensitive to the presence of interfering antibodies—their presence in the sample does not affect the result of measurement of analyte concentration. To suppress non-specific binding of sample components, the sample is further preferably diluted with solution containing components selected from the group consisting of ionic detergents, non-ionic detergents, casein, blocking agents prepared from casein, serum albumins, immunoglobulins or DNA.

In another preferred arrangement, solution containing a recombinantly prepared analyte selected from the group consisting of bacterial, yeast and cell lysate, conditioned bacterial, yeast and cell medium is used as a sample. Recombinantly prepared analyte can, like the binding molecule for its selective binding, contain artificially introduced universal epitope, which is used for selective binding to the binding molecule immobilized on the solid carrier or on a suitably treated surface of the solid carrier, equally as described above for selective immobilization of binding molecule on the surface of the solid carrier.

When a solution of purified recombinant or purified endogenous analyte is used as a sample, in addition to selective binding of the analyte to the binding molecule, non-specific covalent or non-covalent adsorption of the analyte directly on the surface of the solid carrier (equally as described for the direct adsorption of binding molecule) can be used to immobilize the analyte on the surface of the solid carrier. If the analyte is bound directly to the solid carrier, either by non-specific non-covalent adsorption or covalent bonding, the surface of the solid carrier is then incubated with a blocking solution. The blocking solution preferably contains ingredients selected from the group consisting of albumins, casein, casein blocking agents, nucleic acids, and immunoglobulins.

After binding the analyte from the sample, either selectively to the binding molecule or directly to the surface of the solid carrier, the solid carrier is incubated with a solution of a detection probe consisting of the compound for selective binding to the active site of the analyte (ligand portion), covalently linked through a chemical linker with an oligonucleotide tag (amplifiable DNA template), for selective binding of the ligand portion of the probe to the active site of the immobilized analyte. To suppress non-specific binding of the detection probe, the detection probe is preferably diluted with a solution containing components selected from the group consisting of ionic detergents, non-ionic detergents, casein and blocking agents prepared from casein, serum albumins, immunoglobulins or DNA.

It was also tested, that the procedure with the selective immobilization of the analyte via a binding molecule enables that the analyte in the sample can be first incubated along with the detection probe for selective binding of the detection probe to the active site of the analyte, before incubating the analyte in the sample with the solid carrier. This mixture of analyte and the detection probe is then incubated with the solid carrier and therein bound immobilized binding molecule; i.e. this step replaces the steps of incubation of the analyte in the sample with the solid carrier and subsequent incubation of detection probe along with the solid carrier with the bound analyte.

Such a procedure is particularly advantageous for endoproteases, which are usually autoproteolytically degraded. Their degradation can be effectively prevented by first incubating with a detection probe, which after binding into the active site inhibits the proteolytic activity, and then with the solid carrier. Conversely, if endoprotease is first incubated with a solid carrier with immobilized binding molecule and only then with the detection probe, autoproteolytic degradation of the protease can occur during incubation with the solid carrier. Incubation of detection probes with the analyte prior to incubation of the analyte with a solid carrier is also advantageous if the active form of the analyte is destabilized by selective binding to a binding molecule attached to the solid carrier or is otherwise unstable in time, because binding the detection probe to the active site of the analyte usually stabilizes the active form. Furthermore, this procedure saves one incubation step and optional washing, which in addition to accelerating the protocol can in some cases improve the sensitivity of the assay.

In the following step, the solid carrier is washed free of unbound probe and then the amount of bound detection probe is determined, preferably by qPCR. qPCR reaction mixture is added to the washed solid carrier, typically containing a polymerase, a mixture of deoxyribonucleotide triphosphates (dNTPs), primers, fluorogenic probe or fluorescence colour for dsDNA detection and buffer with additives. Subsequently, oligonucleotide tag is amplified in qPCR and during each cycle, fluorescence intensity is monitored from which the $C_q$ value for each sample is computed; the $C_q$ value is inversely proportional to the logarithm of the concentration of the probe, which in turn is proportional to the concentration of the analyte. Process and evaluation of qPCR is such a routine method nowadays that it is not necessary to describe it in detail.

The amount of bound detection probe is determined either directly on the solid carrier so that solution used for detecting is added to the solid carrier and subsequently observable quantity proportional to the amount of bound probe is measured. This can include not only the above-described determination by qPCR, but also by many other methods, which are further described in detail. In another arrangement, washout solution is first added to the washed solid carrier and after the bound probe is released to this solution, its amount is determined in this solution. As it was found, simple release of the probe from the active site, which is described by dissociation rate constant, $k_{off}$, can be used to release bound probe into the solution without loss of sensitivity and dynamic range. Alternatively, the chemical linker preferably contains for example a disulfide bridge, which is reduced with a suitable reagent contained in the washout solution, causing a rapid and quantitative release of the oligonucleotide tag from the surface of the solid carrier into the solution. Preferably, conventional reducing agents such as dithiothreitol, β-mercaptoethanol, tris(2-carboxyethyl) phosphine (TCEP), and immobilized TCEP that are compatible with the DNA polymerase in the following qPCR assay, are used as reducing agents. The advantage of such an arrangement is for example the possibility of using different microplates for immobilization of the analyte with the probe and for its subsequent detection, as the solution with released probe can be transferred to a new plate. This allows even polystyrene plates to be used for the immobilization before the subsequent detection by qPCR, although these are not suitable for thermal cycling in the thermal cycler for qPCR.

The practical advantage of the present invention is that the chemical structure of many compounds potently and selectively binding to the active sites of important analytes is already known, primarily because a number of receptors and enzymes are suitable targets for therapeutic intervention and their inhibition is beneficial. Likewise, key interactions between the pathogen and the host are also targets of therapeutic intervention, in particular by inhibiting the interaction between the surface ligand of the pathogen and the host cell receptor. The most successful drugs against hardly curable or otherwise incurable viral diseases are very potent inhibitors of key enzymes for viral replication. Inhibitors of HIV protease, HIV reverse transcriptase, and recently also HCV NS5B polymerase belong to the most successful clinically used inhibitors. While for clinical use low-molecular substance mustn't be toxic and must be soluble in the aqueous phase, the method disclosed in this patent application preferably uses not only related compounds for selective binding of the analyte, but also the toxic compounds or hardly soluble in the water phase or completely insoluble compounds. Insoluble compounds for selective binding of the analyte can be used because their conjugation with very polar and soluble oligonucleotide increases their solubility, so that the resulting detection probe is easily dissolved at the concentrations required for the determination.

For the purposes of this invention, enzyme inhibitor means a substance capable of binding to the active site of the enzyme and thus capable of the displacement of the substrate or substrates and/or enzyme cofactor or cofactors from its active site, which slows down the enzyme-catalysed reaction of the substrate or substrates. The enzyme is a biomacromolecule, consisting usually from polyribonucleotide or polypeptide chains, having specific three-dimensional structure that selectively catalyses a selected chemical reaction by decreasing the free energy activation barrier. The selectivity of catalysis is due to the particular arrangement of the active site of the enzyme, into which a substrate or substrates and optionally cofactors are selectively bound. There are entire groups of enzymes that catalyse the same type of reaction as well as common inhibitors of more enzymes in a given group; for example, pepstatin inhibits a large group of aspartic proteases. Although immediate vicinity of the cleaved bond may be the same, the whole binding cavity of the active site is usually different, and therefore even in such a group (e.g. aspartic proteases) each enzyme catalyses the reaction only for a more or less limited group of substrates. Due to the described differences in the binding cavity, there are selective inhibitors selectively binding to the active site of one enzyme only, or a just few various enzymes. The design of selective inhibitors is a very common and difficult problem in Medicinal Chemistry. During the development of an inhibitor as a new drug, researches often begin with substances that inhibit several different enzymes, and the inhibitor is only later modified to inhibit just the target enzyme. Inhibition of other than the target enzyme is common cause of side-effects, good example are the nonsteroidal COX-2 inhibitors that are also inhibiting COX-1.

In the proposed method of quantification of analytes, complete selectivity of the inhibitor is not needed because in addition to the inhibitor, the selectivity of determination is also given by the antibody used as binding molecule. Preferably, a common inhibitor of several enzymes can be used as the ligand part of the detection probe and in combination with various antibodies, assay for selective determination of several analytes can be then developed without the need to develop and synthesize a detection probe individually for each of them.

To test the inhibitory efficiency of the tested substances, the common inhibitor of several enzymes is even more preferably used because starting compound of the drug development pipeline, which is not sufficiently selective, is used for synthesis of the detection probe. The probe prepared is then used, as described in this patent application, to directly quantify the selectivity of other upcoming substances and based on the obtained results, those agents can be selected that selectively inhibit only the target enzyme. With a single probe, test essay can thus be developed precisely for those enzymes which are relevant for further development of pharmaceuticals. The examples of our application describe the use of a selective inhibitor of HIV protease, the common inhibitor of glutamate carboxypeptidases II and III (GCPII and GCPIII), the common inhibitor of carbonic anhydrases II and IX (CA-II and CA-IX), the common inhibitor of neuraminidases of human influenza subtypes N1 and N2, and finally the common inhibitor of aspartic protease of pepstatin.

For the purposes of this application, a receptor means a protein which is capable, after binding of the ligand, agonist, of producing intracellular signal that is reflected in altered enzymatic activity or other activity of the receptor itself, or of proteins directly or indirectly associated with the receptor, or in altered concentration of certain ions and thereby altered enzyme activity or other activity of the ion-dependent proteins, or in altered concentration of second messengers and thus altered activity of cellular proteins, and last but not least optionally in altered expression of certain genes. An example of such a receptor is typically a membrane-associated protein, usually comprising structural domains on both sides of the membrane, linked with one or more transmembrane segments. A key feature of such receptors is that upon binding of ligand, they change their conformation (often through multimerization) and thereby transfer the information about the ligand binding through the membrane.

In the first large group of receptors, the signal is transducted either via altered enzymatic activity or other activity of structural domains on the other side of the membrane of the receptor itself or of proteins (enzymes) associated with the receptor, typically GTPases (G-proteins) or protein kinases. Activated associated proteins may then activate other proteins and thereby trigger a complete signaling cascade, often involving so-called second messengers such as phosphatidyl inositol triphosphates, diacyl glycerol, calcium ions, cyclic AMP or GMP. Examples of such receptors are so called metabotropic glutamate receptors in the human nervous system, EGF-receptor, insulin receptor, integrin receptors, and many others.

The second major group of receptors, after ligand binding (either extracellular or intracellular), produces a signal by changing their permeability for selected ions, i.e. changing their intracellular concentration. Such receptors are then referred to as ionotropic receptors, and examples include glutamate AMPA, kainate or NMDA receptors. Another type of receptors are e.g. steroid hormone receptors, located in the cytoplasm, which, after ligand binding, are transferred to the nucleus, where they regulate expression of certain genes. Receptor ligands may generally be another protein, extracellular matrix components, a peptide or a substance of lipid, amino acid, carbohydrate, steroid, or combined type.

Because effector site of the receptor (i.e. ion channel itself or enzymatically or otherwise active domain) and the ligand binding site are spatially separated from each other, the use of low molecular weight ligands for binding to the active site of the receptor is more complicated than for enzymes. For the purposes of this application, agonist, co-agonist, antagonist or blocker of receptor or group of receptors are defined by an example of the NMDA ionotropic glutamate receptor: for receptor activation, both agonist and a co-agonist are bound to the corresponding binding sites, and the binding causes a conformational change leading to receptor activation. Each of these substances binds to another site of the receptor; agonist is physiologically mainly L-glutamate, while the co-agonist is physiologically glycine. Other agonists bind to the glutamate binding site, such as L-aspartate, or partial agonists such as N-methyl-D-aspartate (NMDA); and other co-agonists bind also to the glycine binding site, such as D-serine, or partial co-agonists. In addition, there is an allosteric site on the receptors, into which receptor modulators bind, e.g. polyamines or pregnenolone sulfate. Finally, substances which bind directly to receptor ion channel, serve as blockers of these receptors, as they prevent the passage of ions through the channel. Antagonists of such receptors may then be not only the mentioned blockers, acompetitive antagonists such as chloroform, phencyclidine or amantadine and noncompetitive antagonists such aptiganel, but also competitive antagonists binding to the glutamate or glycine site (such as selfotel). All of these groups of substances will be used as the ligand portion of the detection probe for sensitive detection of receptors, as well as to determine the ability of the tested substances to bind to the corresponding site of the receptor.

Depending on the type of substance used to prepare the detection probe, binding of tested substances to specific binding sites on the receptor is then tested. This approach is unique; as only the effect of the substance, not specific binding site, can be detected using current assays based on whole cells. Testing the selectivity of the inhibition of the receptors is also important, as the biggest problem in developing drugs targeting particularly NMDA receptors is their low selectivity towards other glutamate receptors, which leads to severe side effects. The method proposed here enables (similarly as described above for enzymes) systematic testing of these selectivities for large sets of substances, which has not been possible with current methods. These typically measure e.g. change in intracellular calcium ion concentration after exposure to the tested substance, which does not allow exact resolution of the tested substance mechanism of action. Similarly as with enzymes, ligands binding to a variety of different receptors can be preferably used for preparation of probes for universal testing of the ligands of respective receptors.

Another applicable object of the invention are voltage-gated channels, although they do not fall within the above described definition of receptors, however, their low-molecular-weight blockers are known, such as tetrodotoxin or lidocaine. They are useful for the preparation of a detection probe capable of binding to ion channels and usable for their quantification as well as for finding their novel blockers.

For the purposes of this application, a transporter is also defined on the basis of its biological function. It is a protein molecule capable of selective binding of the ligand, i.e. the transported substance, and capable of mediating its transport after binding. This is often the transport of low-molecular substances through the lipid membrane, which would otherwise do not pass through it, or with very low efficiency. This means that it is usually the transport of substances between inside and outside of cells. Examples include glucose, citrate or high-affinity alpha folate receptors, enabling transmission of folic acid and its methotrexate analogue used to treat certain types of tumors. Examples of a similar type are also amino acid transporters in hemoencephalitic barrier. An example of a different type of transporter is mannose-6-phosphate receptor, which upon recognition of its ligand, which is specific posttranslational modification of the protein, mediates the transport of the bound ligand into a cell component, in this case the lysosome. It is obvious that this does not have to be a transfer of ligand across lipid bilayer, but also the sorting and transfer of ligands to specific cellular components. Transported substance or other substance capable of binding to the binding site for the transported substance is used as the ligand portion of the detection probe for sensitive detection of transporters, as well as for testing the inhibitory capacity of the tested substances against the transporters.

A compound for selective binding to the active site of the analyte, i.e. the ligand portion of the detection probe, is preferably prepared with a chemical linker, through which it is then linked to the oligonucleotide tag. This linker is connected to the compound at a position that does not affect its binding into the active site of the analyte. A suitable place for connection of the linker is determined either from knowledge of the three dimensional structure of the active site with bound compound for selective binding to the active site of the analyte, or by preparing multiple compounds with various connection points of the linker and testing the strength of their binding into the active site of the analyte. Furthermore, the linker is prepared in such a length that upon binding of the compound to the active site of the analyte, the linker reaches outside the binding cavity of the analyte and thereby enable connection of the oligonucleotide tag that will not interfere with the binding of the compound to the active site of the analyte. If a suitable connection point of the linker and a suitable length of the linker can be found, already known compounds binding to the active site of the analyte can be used for the preparation of the ligand portion of detection probe. The chemical linker is preferably selected from the group consisting of polyethylene glycol; peptide; polyamide; aliphatic or hydroxylated aliphatic chain; optionally an organic polymer such as polydextran, hydroxyethyl methacrylate (HEMA), hydroxypropyl methacrylamide (HPMA); and combinations thereof. The linker is further prepared with a selected group from a pair of bioorthogonally reactive groups, and an oligonucleotide tag with the second corresponding group from the given pair of bioorthogonally reactive groups is prepared. Reaction of these groups produces the resulting detection probe, i.e. compound for selective binding to the active site of the analyte linked via a chemical linker to the oligonucleotide tag. Pairs of bioorthogonally reactive groups are preferably selected from the group consisting of amine—activated ester, hydroxyl—activated ester, amine—activated phosphate, azide—alkyne ($Cu^{2+}$ catalysis), azide—cyclooctyn, azide—dibenzylcyclooctyn, hydrazine—aldehyde or ketone, aromatic hydrazine—aromatic aldehyde or ketone, tetrazine—alkene, sulfhydryl—alkene, sulfhydryl—maleimide, sulfhydryl—sulfhydryl, amine or sulfhydryl—epoxyalkane, amine or sulfhydryl—tosylate or mesylate or alkyl halide, sulfhydryl—vinyl sulfone, amine—aldehyde or ketone (cyanoborohydride reduction), isocyanate—amine or hydroxyl, amine—sulphonyl chloride, amine—amine (via sulphuryl chloride pyridine or dichloropyrimidine or cyanur chloride), azide—nitryl, diol—boronic acid, diol—phenylboronic group, amine—hydroxyl (via cyanur chloride).

Reaction of a compound for selective binding to the active site of the analyte with a linker with the first group from the bioorthogonal pair and the oligonucleotide tag containing the second group from the bioorthogonal pair is achieved by simply mixing their solutions in suitable proportions and under suitable conditions, and most preferably by allowing to react at room temperature overnight. For the quantitative extent of reaction, molar excess of the compound for selective binding with a linker is used, as it is obtainable in larger amounts than the oligonucleotide. Molar excess of this compound is particularly important if it is prepared as an activated ester for reaction in the aqueous phase e.g. with an amine on the oligonucleotide, as an activated ester in the aqueous phase is gradually hydrolysed and thus a part of it cannot react with the amine on the oligonucleotide. A compound for selective binding is preferably used in a 5-50 fold molar excess; however, if organic phase instead of water is used, quantitative conjugation can be achieved also with lower excess or even with equimolar amounts. Similarly, with a slight excess of such compound, high efficiency conjugation e.g. between an alkyne and an azide on the reactants can be achieved. Specific reaction conditions can be chosen almost arbitrarily, optimally with regard to the type of conjugation reaction and the type of low molecular weight substance. For some types of reactions, sufficient efficiency can be achieved only in a narrow pH range, e.g. for a reaction of an activated ester with an amine. Thanks to the stability of DNA in a wide pH range, both acidic and neutral, and even basic pH can be used for conjugation reaction. If the substance is insoluble in aqueous phase, the reaction can be performed in an organic solvent, e.g. DMSO. Insolubility of the compound for selective binding to the analyte in the aqueous phase does not present a technical problem for determination of the analytes, because after conjugation with very polar and well soluble DNA, the whole conjugate is water-soluble irrespective of the hydrophobicity of the attached low molecular compound. As it turned out, by connecting the DNA, a significantly better solubility can be achieved without loss of biological activity of the original compound. Organic phase can also be used for the reaction if one of the reactive bioorthogonal groups is not stable in the aqueous phase. Use of the organic phase is possible due to the fact that DNA as a template for the PCR reaction does not need its specific three-dimensional structure and thus its dissolution in an organic solvent does not negatively influence its function (as opposed to proteins, especially antibodies). After conjugation, the resulting detection probe is purified from the remaining compounds for selective binding of the analyte, preferably by the separation on the basis of very different molecular weight of the detection probe (usually around 20 000 Da) and the compound (usually up to 1000, at most 2500 Da) by ultrafiltration in microcentrifuge columns. Preferably a "cut off" of the membrane is used, thus capturing substances having a molecular weight greater than 10 000 Da, which separates detection probe together with the optionally remaining unreacted oligonucleotide from the free compound. While the free compound for selective binding to the analyte would compete with the detection probe for binding to the analyte, and therefore needs to be separated from the detection probe, the remaining unreacted oligonucleotide does not significantly affect properties of the detection probe and therefore does not need to be separated from the probe. In the basic embodiment of the invention, the oligonucleotide tag is a single stranded DNA with a length of typically up to 200 bases, preferably 30-80 bases. To determine the amount of bound detection probe, the amount of the oligonucleotide tag is selectively quantified by qPCR. Said length of the tag is sufficient as a template for qPCR, i.e. for primer pair (forward and reverse) to anneal, and possibly a fluorogenic probe (e.g. hydrolysis TaqMan probe with sequence complementary to the oligonucleotide tag and containing a fluorophore and a quencher; the fluorophore and the quencher are separated during the DNA amplification by the cleavage of the probe by the polymerase which leads to increase of the fluorescence signal). If a fluorogenic probe is not used, it is sufficient to use fluorescent dyes such as SYBR Green (e.g. Roche) binding to double-stranded DNA generated during qPCR. The sequence of the oligonucleotide tag is freely optional; the sequence of the primers and possibly also the fluorogenic probe is then selected depending on the tag sequence.

The fact that sequence is not limited to, e.g. having to create a specific three-dimensional structure as in aptamers, advantageously allows to select different sequences for different analytes in different detection probes, so that each of these detection probes could be selectively determined in a mixture of detection probes. It is used for example for the parallel determination of multiple analytes in one reaction. In such arrangement, a mixture of binding molecules is immobilized on the solid carrier, each of which recognizes a different analyte. The solid carrier is then incubated with the sample for selective binding of the analytes contained in the sample to the corresponding binding molecules and then the solid carrier with the bound analytes is incubated with a mixture of detection probes, each containing a different oligonucleotide tag and each binding to a different analyte. Afterwards, the unbound detection probes are removed by washing (washed off) and the bound amount of each of them is selectively determined, which is proportional to the amount of corresponding analyte in the sample.

If the solid carrier is the surface of microplate wells, simultaneous selective determination of different sequences is achieved by the following ways: In the first method, after washing away the unbound probe, mixture of primers for amplification of each of the oligonucleotide tags of the detection probes is added, either specific to each sequence, or common to more sequences, and a mixture of differently coloured fluorogenic probes, which are specific (complementary) for each individual sequence. In the subsequent qPCR, in each well of the microplate, all the sequences present in all detection probes are simultaneously amplified and their selective detection is achieved by using different colours of fluorescence probes, each one specific for only one given sequence from the mixture. The number of the determined sequences simultaneously in one reaction is limited by the number of different colour filters in qPCR devices and therefore there is a practical limitation to 5-6 sequences simultaneously. Another alternative is to release bound detection probes to a solution, for example by simply incubating with an eluting solution, and the subsequent division of this solution into more wells, wherein in each well one particular sequence is selectively amplified and quantified. This is accomplished by using selective primers or at least one selective primer and one common primer; while selective fluorogenic probes are not needed. This way, the number of determined sequences is not limited at all. Another similar method uses a pre-amplification of sequences of the bound detection probes directly in the original well with specific or common primers and subsequent division of the solution containing the amplified sequence into multiple qPCR reaction and subsequent determination as in the previous method. Simultaneous determination of larger numbers of individually bound probes can also be achieved by analysis on chips with hybridization probes, or by using next generation sequencing methods.

For all the above-mentioned methods of determination, in particular by means of qPCR, it is also possible to use very short oligonucleotide tags, typically of between 10 and 30 bases. Such an oligonucleotide is too short to be a template in a polymerase chain reaction, but serves as a primer in this reaction, which after annealing and polymerization by the polymerase extends the added template DNA. The extended template DNA is then amplified using the primer pair in qPCR, wherein all or part of the complementary sequence of one of the primers is not included in the original unextended template DNA, whereas it is present in the oligonucleotide tag. Thereby the amount of a very short oligonucleotide tag is quantitatively determined.

Single-stranded DNA of oligonucleotide tags can be prepared in various modified forms. Modifications described below can either be directly introduced into this DNA strand, or this strand can be paired with the complementary strand containing the target modification. Given that the detection probe (unlike probes containing an antibody) is thermostable, selective pairing with the second strand can be performed not only prior to conjugation of the oligonucleotide tag with the ligand part, but preferably also after the conjugation. The advantage of this approach is that one chemically synthesized detection probe having a single stranded oligonucleotide tag can be used to simply prepare a quantity of derived detection probes with double-stranded DNA, bearing the desired modification. Oligonucleotides with different modifications, which are mainly fluorophores, biotin, thiol group, amino group, azido group or octyn group, are commercially available in the form of custom synthesis. Actual annealing of the second strand on the original DNA strand is done by mixing the two strands (the second strand and the detection probe) in a suitable ratio (usually equimolar) and heating followed by slow cooling.

Alternatively, the second strand containing the desired modifications is introduced by using a primer annealing to the original strand of the oligonucleotide tag and its extension with polymerase by simultaneous incorporation of bases bearing the target modification. Such modified bases are also commercially available.

Oligonucleotide tags for determination by qPCR may therefore be formed not only by single-stranded DNA, but also double-stranded. Preferably, the detection probe is prepared with biotin attached to the oligonucleotide tag; such a probe in a molar excess is then incubated with tetravalent biotin-binding protein, preferably neutravidin or streptavidin, and after binding to this protein, the whole complex is purified, preferably by ultrafiltration through a membrane with pores to capture compounds of molecular weight above 100 kDa, wherein the complex remains in the retentate, while unbound detection probe passes through. The resulting tetravalent complex is then used instead of the original detection probe for the detection of active forms of analytes and for determining the ability of tested substances to bind to the active site of these analytes. The advantage of such a complex is its tetravalence and hence increased affinity, which is demonstrated by the example of detection probe for determination of carbonic anhydrase IX, where use of such a complex improved the sensitivity of the assay over the use of the original monovalent detection probes. Due to this phenomenon, weaker inhibitors may be used for preparation of detection probes.

Alternatively, multivalent probe can be prepared by reacting a compound for selective binding to the active site of the analyte with a linker with the first group from the bioorthogonal pair and the oligonucleotide tag containing multiple copies of the second group from the bioorthogonal pair (such oligonucleotides are commercially available). Or, such oligonucleotides can be prepared by solid phase synthesis from commercially available nucleotide building blocks with attached required bioorthogonal group. For the detection of CA-IX, a single-stranded probe containing two molecules of the compound for selective binding to the active site of CA-IX was prepared and this procedure has proved very advantageous. Connecting two copies of the compound to the oligonucleotide tag helped to achieve improved affinity by at least twenty times when compared to the parent compound or when compared to oligonucleotide tag with only one copy of the compound and approximately one order of magnitude when compared to complex with neutravidin as described above. For the detection of CA-IX in a cell lysate or serum, limit of detection less than 10 fg (approximately 200 zmol) was achieved with a linear range between 10 fg and 1 ng, i.e. five orders of magnitude. Such a substantial increase in affinity due to the addition of a second molecule of the compound is due to the fact that the CA-IX forms a dimer with two active sites and the bivalent probe apparently binds simultaneously to both of these sites. Higher affinity compared with neutravidin complex is probably due to the greater flexibility of the single-stranded DNA in the bivalent probe; it is higher than for DNA complexed with neutravidin, and bound compounds thus more easily reach the active sites of CA-IX.

A way to further improve the avidity is the connection of multiple copies of the detection probe on a gold nanoparticle. Preferably a detection probe is prepared, containing thiol groups on the oligonucleotide tag for direct conjugation to gold nanoparticles. Conjugation of detection probes with gold nanoparticles is then achieved by mixing solutions of the two components and a gradual increase of ionic strength followed by separation of particles and unbound detection probes by centrifugation in sucrose gradient. A more preferred method involves the preparation of gold nanoparticles coated with a film consisting of multiple copies of molecules consisting of thiol groups connected to unbranched alkane chain containing optimally from 6 to 18 carbon atoms. This chain is (at the opposite end) connected to a polyethylene glycol chain, optimally 3 to 18 ethylene glycol units, carrying one of the bioorthogonally reactive groups at the other end, preferably an azido group. These molecules are then connected to gold nanoparticles via thiol groups; and the alkane and the ethylene glycol portion form semi-crystalline structure on the surface of the particles and thus significantly improve their colloidal stability. The azido group is then used for simple conjugation to the detection probe which preferably comprises dibenzyl cyclooctyn (DBCO) group which reacts readily with the azide group to form a triazole without catalysis. Detection probe with DBCO group is preferably prepared from single-stranded detection probe prepared by a standard way paired with a complementary strand of DNA that contains the DBCO group.

Very sensitive detection is important not only for the determination of PSA in the blood serum of cancer patients after prostatectomy, but also for tissue biopsy, as it allows taking only very small amounts of tissue, thereby reducing the invasiveness of the surgery. According to the example of CA-IX in which sensitivity of 10 fg was achieved with detection probe prepared from compound with submicromolar affinity, it can be assumed that micromolar dissociation constant of the compound and the analyte will usually allow detection of the analyte with a sensitivity of lower than 10 amol, corresponding to 1 pg of analyte with molecular weight of 100 kDa.

A compound binding tighter allows even considerably greater sensitivity of detection even without utilization of avidity, as described in the examples for the detection of PSMA, where sensitivity of ten attograms (corresponding to tens of molecules) was achieved. This is about six orders of magnitude less than using currently the most sensitive detection of PSMA by Western blotting (detection limit of 100 pg) or by ELISA (detection limit of 10 pg). At the same time, the range of the determination of more than six orders of magnitude is achieved; the examples show the quantitative detection in the range of less than 1 fg to more than 1 ng of PSMA (the maximum range of the ELISA assay is around three orders of magnitude).

A limitation of the sensitivity of determination of analytes is the nonspecific adsorption of the detection probe, as the probe bound this way is detected as well as probe selectively bound to the immobilized analyte. Increasing of assay sensitivity is therefore achieved by suppressing the nonspecific adsorption of the detection probe by adding suitable agents into the working solution of detection probes. The detection probe is diluted in a solution containing additives selected from the group consisting of ionic detergents, non-ionic detergents, casein and blocking agents prepared from casein, serum albumins, DNA or immunoglobulins. Usually the detection probe is diluted before incubation with the solid carrier with bound analyte in a buffered solution at a suitable pH, preferably physiological pH 7.4. Buffered solution also usually contains dissolved salts, preferably dissolved sodium chloride in a concentration higher than 0 and up to 1.5 mol·l$^{-1}$. The solution optionally also contains a non-ionic detergent, preferably Tween-20 (polyoxyethylene (20) sorbitan monolaurate), at a concentration of higher than 0% up to 1% (vol./vol.), preferably at a concentration of 0.1% (vol./vol.). Significant decrease in nonspecific adsorption of the probe was achieved by the addition of low levels of sodium dodecyl sulphate (SDS), preferably at final concentrations ranging from 0.001% to 0.02% (wt./vol.). Decrease of nonspecific adsorption of the probe is achieved also by the addition of small quantities of casein blocking solution, preferably in the range of the final 200-fold to 5000-fold dilutions (initial concentration of the solution was 5.5% (wt./vol.)). Adding both the SDS and the casein blocker lead to even greater suppression of nonspecific binding. As shown in the examples, several concentrations of both of these substances and their combinations is tested for each analyte and a corresponding detection probe to obtain such a composition of the solution in which the nonspecific adsorption of the detection probe is lowered and simultaneously its affinity in specific binding to the active site of the analyte is not significantly affected. Decrease in non-specific binding is typically in the range of one to two orders of magnitude (but may be considerably larger), which results in increase in signal-to-background ratio and thereby an increase assay sensitivity of the same magnitude. As also shown in the examples, further surprising way to suppress nonspecific binding by at least another order of magnitude and thereby increase the sensitivity of the analyte detection of the same magnitude is the replacement of single stranded oligonucleotide tag with a double stranded tag.

Further increase of the sensitivity of the analyte determination was achieved by incubation of the solid carrier with bound analyte with the detection probe at its optimum working concentration. To determine the optimal concentration, $K_d$ value towards the corresponding analyte is determined for each detection probe, which is practically done by titration, i.e. multiple measurements for the same analyte concentration at a changing the concentration of the detection probe.

The equation for the dissociation constant is:

$$K_d=[E]*[P]/[EP] \qquad (1),$$

where [E] is the concentration of free analyte, [P] is the concentration of free detection probe and [EP] is the concentration of the analyte in complex with the bound detection probe. The concentration of free analyte corresponds to the difference of the total analyte concentration ($E_{tot}$) and the concentration of an analyte complexed with the probe ([EP]), and by substituting this relation into the previous equation and solving for [EP] we get the equation (similarly as for the determination of Michaelis constant of substrate and enzyme):

$$[EP]=E_{tot}*[P]/(K_d+[P]) \qquad (2).$$

The concentration of the free detection probe [P] is not known, but if the total concentration of analyte is either lower than the $K_d$ of the detection probe, or the total concentration of analyte is lower than the total concentration of the detection probe $P_{tot}$, for simplification of the titration evaluation, [P] can be replaced by $P_{tot}$ and the last relation can then be written as:

$$[EP]=E_{tot}*P_{tot}/(K_d+P_{tot}) \qquad (3).$$

The concentration of bound and immobilized probe in a complex EP is quantity measured by qPCR. The actual dissociation constant is determined by plotting the measured values of EP quantities against the used analytic concentration of detection probe and their fitting to a function described by equation (3) connected for example with numerical determination of dissociation constant of the probe (and analytical concentration of the analyte that may not be known in advance).

A number of empirically observable properties can be derived from plotting the dependence of [EP] to $P_{tot}$ from the equation (3). While at $P_{tot}$ concentrations much lower than $K_d$, [EP] (i.e. amount of detection probe bound to immobilized analyte) increases linearly with increasing $P_{tot}$, at $P_{tot}$ getting close to $K_d$, the growth of [EP] slows down, and gradually reaches a plateau at $P_{tot} \gg K_d$ where the [EP] value corresponds to $E_{tot}$. E.g. at $P_{tot}=K_d$, [EP]=½ $E_{tot}$, i.e. exactly half the analyte is bound by the probe. In contrast, the observed dependence of the non-specifically adsorbed amount of the detection probe on the total concentration ($P_{tot}$) is approximately linear for all concentrations tested, i.e. at smaller, similar or greater concentration than corresponding $K_d$ of the specific interaction, which can be explained by probably substantially larger dissociation constant characterizing the non-specific interaction.

Of these observations, the optimum working concentration of the detection probe can be deduced. The highest sensitivity of the determination of analytes is achieved when using a probe concentration approximately equivalent to its $K_d$ towards a given analyte, or concentration even lower than the $K_d$ towards a given analyte in case a non-zero non-specific adsorption at a given probe concentration is observed.

Our technical solution is outstanding in the enormous dynamic range of detection, wherein the quantitative dynamic range of detection is defined as a range of analyte concentrations, in which the measured signal is linearly proportional to the total concentration of the analyte. In this case, the $C_q$ value is measured by qPCR; the $C_q$ value is indirectly proportional (linearly with a negative proportionality constant) to the logarithm of the amount of detection probe bound to the analyte ([EP]), which is within the aforementioned quantitative dynamic range directly proportional to the total analyte concentration ($E_{tot}$) i.e. the [EP]/$E_{tot}$ ratio is constant within this range. The modified equation (2):

$$[EP]/E_{tot}=[P]/(K_d+[P]) \qquad (4),$$

implies that this condition is fulfilled if the concentration of probe ([P]) can be substituted by its analytical concentration $P_{tot}$, because then the whole right side of the equation (4) is equal to a constant, since neither $P_{tot}$ nor $K_d$ depend on the changing total amount of analyte $E_{tot}$. The modified equation (2):

$$[EP]/[P]=E_{tot}/(K_d+[P]) \qquad (5),$$

further implies that [P] may be substituted by $P_{tot}$ under conditions of either $E_{tot} < K_d$ or $E_{tot} < [P]$ or $E_{tot} \ll P_{tot}$ since then [EP]<[P], and we can write [P]=$P_{tot}$ [EP] $P_{tot}$, because [EP]<$P_{tot}$. Under these conditions, the measured signal is proportional to $E_{tot}$ This leads to important observations for dynamic range of the determination; at low concentration of probe, lower than or approximately equal to the $K_d$ of the selective binding of the probe to the analyte, the dynamic range at the lower limit of detection is limited by nonspecific adsorption of detection probes, while at the upper limit of detection, it is limited by the $K_d$ of the probe. With higher probe concentrations than its $K_d$, nonspecific adsorption increases, but the upper limit of detection is not limited with $K_d$ anymore, but with the concentration of the probe, which is higher. Higher concentrations of the probe thus move the dynamic range to higher concentrations of the analyte, while the fold difference of the lower and upper limit of detection remains unaltered.

For a more precise knowledge of the range, in which [EP] is directly proportional to $E_t$, exact relationship for [EP] can be derived:

$$[EP]=(K_d+P_{tot}+E_{tot}((K_d+P_{tot}+E_{tot})^2-4*(P_{tot}*E_{tot}))^{0.5})/2 \qquad (6).$$

By comparing EP computed according to equations 3 (assuming a linear correlation) and 6 (the exact relation) we can determine the deviation of dependence [EP] on $E_{tot}$ from linear proportion. For example, if $E_{tot} > P_{tot}$ then at $E_{tot} = \frac{1}{2} K_d$ the deviation from linearity is about 40%, at $E_{tot} = K_d$ the deviation is about 20% and with decreasing the $E_{tot}$ concentration, deviation decreases further. This means that at $E_{tot} > P_{tot}$ upper limit of linear range for $E_{tot}$ concentration reaches approximately $\frac{1}{4} K_d$. In contrast, if $E_{tot} \leq P_{tot}$ then irrespective of the ratio of $E_{tot}$ and $K_d$, deviation from linearity never exceeds 25%. This means that the linear range always reaches at least to the concentration of the detection probe, confirming the possibility to shift the dynamic range by increasing the concentration of the detection probe.

The overall dynamic range is actually even greater than the linear range, which is well documented in the calibration curves of analytes in the examples. E.g. the linear range for PSMA detection covers six orders of magnitude of PSMA concentration, while the total dynamic range is approximately one order of magnitude wider. The analyte concentration can be read in outer non-linear regions as well, it is just less accurate than in the linear region.

The linear range of analyte quantification is particularly important for determining the dissociation constant of the tested substances binding to the same active site as the detection probe. The principle is a competition for binding to the active site of the analyte between the detection probe and the tested substance. The possibility to measure the strength of competition in such a large dynamic range is completely new, and it was even necessary to derive some new relations, yet unknown in enzyme kinetics, to use the benefits.

First, under the conditions described above, determined quantity of bound probe is directly proportional to the amount of immobilized analyte, more precisely to the number of free active sites of the analyte. That means that in the absence of a tested substance binding to the active site, all active sites of the analyte are free and the amount of bound probe corresponds to the total number of active sites; while if a tested substance is bound to a certain number of active sites and the probe can thus no longer bind to them, the amount of bound probe is directly proportional to the number of remaining free active sites. From the decrease in the measured concentration of the active sites by x % is therefore apparent that x % of the active sites are occupied by the tested substance; comparing the measured signals with and without the tested substance thus directly reflects the proportion of active sites with the bound tested substance.

For dissociation (inhibitory) constant of the tested substance applies analogously to equation (1) describing the dissociation (inhibitory) constant of the detection probe:

$$K_i=[E]*[I]/[EI] \qquad (7),$$

where $K_i$ is the dissociation (inhibitory) constant of the tested substance, [E] is the concentration of free analyte, [I] is the concentration of free tested substance and [EI] the concentration of the analyte complex with the bound tested substance. The variables relating to the detection probe in the next derivations remain same as in equation (1). For a total amount of analyte applies:

$$E_{tot}=[E]+[EP]+[EI] \qquad (8),$$

and the proportion of active sites occupied by the tested substance is equal to:

$$[EI]/E_{tot}=x/100 \qquad (9),$$

x is the portion of analyte with the active site occupied by the tested substance expressed as a percentage. After solving the equation (9) for $E_{tot}$ and substituting into equation (8), solving and substituting [EP] from equation (1), substituting [EI] from equation (7) and solving, an equation for $K_i$ is obtained:

$$K_i=(100/x-1)*[I]/(1+([P]/K_d)) \qquad (10),$$

expressing the concentration of the unbound tested substance [I] using the total (analytical) concentration of the tested substance $I_{tot}$, which is the sum of the concentrations of bound and unbound probes ($I_{tot}=[I]+[EI]$), substituting for [EI] from equation (9) and solving for [I] we get:

$$[I]=I_{tot}-x*E_{tot}/100 \qquad (11).$$

The resulting equation for calculating $K_i$ is:

$$K_i=(100/x-1)*(I_{tot}-x*E_{tot}/100)/(1+([P]/K_d)) \qquad (12).$$

within the quantitative range of the method, this equation is further simplified by replacing concentration of free detection probe [P] with analytic concentration of the probe $P_{tot}$, which is known. Virtually always, $I_{tot}$ is significantly higher than $E_{tot}$, the entire member ($x*E_{tot}/100$) can therefore be neglected compared $I_{tot}$. The simplified equation is then:

$$K_i=(100/x-1)*I_{tot}/(1+(P_{tot}/K_d)) \qquad (13).$$

Practically, however, the percentage of inhibition is not measured directly, but the amount of remaining free analyte after incubation with the tested substance ($E_{tot}-[EI]$) is compared with the total amount of analyte after incubation without the tested substance ($E_{tot}$), i.e. ($E_{tot}-[EI])/E_{tot}$. For each of the two quantities the $C_q$ value is measured, which is inversely proportional to the amount, i.e. with decreasing amount of free active sites of analyte the measured $C_q$ increases, and if $\Delta C_q$ is defined as $C_q$ measured for an incubation without the tested substance subtracted from $C_q$ measured for incubation with the tested substance, then applies:

$$(E_{tot}-[EI])/E_{tot}=(1+\text{eff.})^{-\Delta C_q} \qquad (14),$$

where eff. is the efficiency of the PCR reaction, which under optimal conditions is equal to one. Equation (13) is then reformulated using the previously mentioned relations for the inhibition percentage:

$$K_i=((1-\text{eff.})^{-\Delta C_q}/(1-(1+\text{eff.})^{-\Delta C_q}))*I_{tot}/(1+(P_{tot}/K_d)) \qquad (15).$$

Accuracy and range of $K_i$ measurement depending on $\Delta C_q$ are determined e.g. by graphically plotting of this dependence, from which it is evident that the dependence of log $K_i$ on $\Delta C_q$ is linear for $\Delta C_q \geq 3$, while it deviates from linearity for lower $\Delta C_q$. That does not mean that lower $\Delta C_q$ cannot be used to calculate $K_i$, only the standard error of the determination is higher for lower $\Delta C_q$. At usual standard deviation of $C_q$ determination by qPCR (equal to 0.15 of the cycle) relative standard deviations of determined $K_i$ depending on the measured $\Delta C_q$ are the following (deviation asymmetry is due to logarithmic correlation):

a) +164%−41% at $\Delta C_q$=0.25 of the cycle, which corresponds to 16% occupancy of the active sites of the analyte with the tested substance (i.e. 16% inhibition by this substance)
b) +64%−30% at $\Delta C_q$=0.42, corresponding to 25% inhibition,
c) +51%−27% at $\Delta C_q$=0.5, corresponding to 29% inhibition,
d) +25%−18% at $\Delta C_q$=1.0, corresponding to 50% inhibition,
e) +15%−13% at $\Delta C_q$=2.0, corresponding to 75% inhibition,
f) +13%−11% at $\Delta C_q$=3.0, corresponding to 88% inhibition,
g) +11%−10% at $\Delta C_q \geq 5.0$, corresponding to 97% and higher inhibition.

This means that any $\Delta C_q$ greater than or equal to 0.42 is suitable for the calculation of $K_i$, wherein for $\Delta C_q \geq 1.0$ unusually high precision is achieved. For the linear range of six orders of magnitude, applicable $\Delta C_q$ range is 0.42 to 20, which corresponds to inhibition percentage in the range from 25% to 99.9999%. Distinction of absolute differences as small as a difference in 99.9998% and 99.9999% inhibition is possible thanks to the fact that remaining free sites of the analyte are measured, the quantity of which, in a corresponding case, are 0.0002% and 0.0001%, and the detection is logarithmic, which means that fold changes rather than absolute differences are detected, which corresponds to a two-fold change for this case an thus $\Delta C_q$ equal to one, which is measured very well and accurately. Dependence of $K_i$ on $\Delta C_q$ including lines showing standard deviation is plotted in the graph in FIG. 4.

An equation for calculating the $K_i$ of the tested substances in a method using bivalent detection probe capable of dual binding to the analyte can be derived similarly:

$$K_i = (1 - 2*R_{aff})/(1 - R_{aff} - (R_{aff}^2 + (1+\text{eff.})^{-\Delta C_q} - 2*R_{aff}* (1+\text{eff.})^{-\Delta C_q})^{0.5}) \quad (16),$$

where $R_{aff}$ is equal to the proportion of dissociation constants of bivalent and monovalent probe. The formula, inter alia, implies that with a varying amount of free active sites there is a steeper change of $\Delta C_q$ than for a monovalent probe, resulting in even higher accuracy of $K_i$ determination than described above for the monovalent probe, because the accuracy of $C_q$ determination itself remains the same.

As shown in the examples for several different enzymes, using our method, it was found that values of the dissociation constants of tested substances may be determined from a single tested concentration of the tested compound. While a monovalent probe was used for most enzymes, bivalent probe was successfully used for CA-IX as well. By comparing the obtained values with the reference values derived from other, more laborious methods, mainly enzyme kinetics, it was found that dissociation constants of the tested substances are determined with great accuracy and repeatability regardless of their used concentration (within the range of the method, the concentrations used were in the range of nmol·l$^{-1}$ to mmol·l$^{-1}$), and regardless of their absolute value (dissociation constants of tested substances were in the range of tens pmol·l$^{-1}$ to units mmol·l$^{-1}$).

The uniqueness of this approach over other methods is in the very large dynamic range, which allows to apply the above derived apparatus and thereby determine the dissociation constant from a single concentration. Unlike other methods, mainly enzyme kinetics, in which the catalyzed reaction rate is measured by detecting the substrate(s)s and/or product(s), it is not necessary to measure the entire titration curve with varying concentrations of the inhibitor. It is interesting that the value of half inhibition, $IC_{50}$, is fairly accurately measurable in enzyme kinetics and is used to calculate $K_i$ using the so-called Cheng-Prusoff equation, which is a special and simplified version of equation (12). Even more significant improvement is brought by this approach for finding and measurement of substances binding to the active site of analytes which do not have an enzyme activity; because for those, it is impossible to use the effect of detection amplification by conversion of more molecules of substrate to product by one molecule of analyte. For them, it is usually necessary to search for alternative, less sensitive methods of determination, e.g. competition with a fluorescently-labeled substance binding to the active site. Our method for quantitative determination of the ability of tested substances to bind to the active site of these analytes, however, can be used with the same efficiency as for enzymes. High sensitivity of our method is advantageous for all analytes, as it allows quantitative testing of the ability of substances to bind to the active site of the analyte with a very low consumption of analyte, whose acquisition and purification, especially in the case of receptors, is usually quite difficult. The sensitivity of detection of the bound probe allows to always use a concentration of the probe lower than or equal to its $K_d$. Equation (15) then implies that our solution enables highly sensitive detection of substances binding to the active site of a given enzyme—any substance whose $K_i$ is equal to or lower than its concentration used is identified as binding. This represents a major advantage over the methods used with less sensitive detection of the bound probe, such as fluorescence polarization, where it is usually necessary to use a probe concentration significantly above its $K_d$ and therefore only those substances are identified whose $K_i$ is significantly lower than the concentration used, and that leads to many false negative results.

Very preferred is also the selectivity of this solution because the use of immobilization by a selective binding molecule allows to test the ability of tested substances to bind to the active site of the analyte without the need to purify the analyte. Preferably, endogenous analyte is directly used, optionally originating directly from biological samples taken form patients, which is enabled by the sensitivity and selectivity of the assay. Using endogenous analyte is not only advantageous because the analyte does not need to be prepared in the laboratory, but also because the binding of the tested substances can be detected directly on specific endogenous analyte, which may vary significantly e.g. between individual humans. In contrast, the option to titrate endogenous analyte with known ligands brings an opportunity to verify the accuracy of the measured amounts of the analyte, which represents an advantage compared to methods using antibody sandwich.

Tested substances are often dissolved in organic solvents, therefore it is preferable when the method of measuring their binding to the active site of the analyte is not affected by these solvents. Likewise, it is preferable when the tested substance itself does not interfere with the determination, since high concentrations of these substances are typically used. The arrangement of our method represents the optimal solution for both of these parameters; due to immobilization of the analyte, both the excess unbound probe and the unbound tested substance and the solvent can be washed away after incubation with the tested substance and the detection probe. If the solvent does not directly denature the analyte, it is compatible with the assay is and does not affect assay results. On the example of PSMA, it was shown that DMSO at a concentration of greater than 0% up to at least 10% (vol./vol.) does not affect the assay results, as well as acetonitrile and methanol in the same concentration range, and similarly non-ionic detergent Tween 20 in a concentration range greater than 0% and up to 1% (vol./vol.). On the example of HIV-1 protease, carbonic anhydrases and other proteins confirmed that DMSO or acetonitrile or methanol in concentrations of up to at least 10% (vol./vol.) do not affect the assay rasults.

Based on the examples, the dissociation constants of the compounds for selective binding to the active site of the analyte used to prepare detection probes, which is sufficient to develop the described method for testing the ability of tested substances to bind to the active site of the analyte, can be in the range of at least 100 pmol·l$^{-1}$ to at least 1 nmol·l$^{-1}$.

Possibility to compete out the detection probe from the active site of the analyte is also advantageous for detection of analytes in complex biological matrices since the detected quantity of the analyte is confirmed by titration with a substance that also binds to the active site. This is a big advantage compared to ELISA, where the same test would consume large amounts of purified analyte that is usually not available.

So far, a method of detecting bound detection probe using qPCR has been described, characterized by enormous dynamic range; but the detection probe can be detected in several other preferable ways, e.g. by fluorescence or through coupled enzyme reactions spectrophotometrically or chemiluminiscently. Such detections are not only faster compared to qPCR, because there is no need of thermal cycling in PCR, but also cheaper because there is no need of expensive reagents, or complicated devices for qPCR. Moreover, this determination is more accurate, since while the detected signal in qPCR is proportional to the logarithm of the concentration of bound detection probe, the measured signal in these methods of detection is directly proportional to the concentration of bound detection probe and thus measurement accuracy (standard deviation) of a few percent units is achieved. A disadvantage of the alternative detection compared to qPCR is a smaller dynamic range and reduced sensitivity. However, as shown on the example of PSMA, assay sensitivity of 1 pg at dynamic range of three orders of magnitude is achieved. At the same time, the assay keeps the other advantages, i.e. it is not prone to false positive results caused by heterophilic interfering antibodies present in complex biological matrices and it detects only the active form of the analyte. The alternative method of detection is therefore preferably used for the detection of analytes in complex biological matrices, where the concentration is not as low as to require detection by qPCR, and where also very small changes in their concentration are relevant e.g. for diagnosis.

Fluorescence detection is performed by preparing an oligonucleotide tag containing fluorophores. Fluorophores may be contained either directly in the DNA strand covalently conjugated to the compound for selective binding to the active site of the analyte, or in the complementary strand. The second option is preferable, because fluorophores can easily be connected to the detection probe already prepared by simply pairing the complementary strand containing the desired modification. A detection probe containing biotin can be prepared in the same way. By simple mixing with neutravidin or any other biotin-binding protein, it is possible to create a multivalent particle which can be separated from free detection probe based on the different molecular size, for example by ultrafiltration. This is particularly advantageous, since there are a number of commercially available conjugates of neutravidin with fluorophores or enzymes, particularly peroxidase. The resulting particle then contains four molecules of detection probe, each with a ligand portion and a biotin-binding protein with linked enzyme or fluorophore for detection, wherein the plurality of ligand components leads to a higher affinity for the analyte immobilized on a solid carrier due to the ability to bind at several locations simultaneously. For comparison, the same particle cannot be prepared in the same manner with a biotinylated antibody, as in contrast to the detection probe, it cannot be biotinylated at one site only, and mixing of a multiple-biotinylated antibody with neutravidin carrying multiple biotin-binding sites would result in a crosslinked product of many antibody molecules and many neutravidin molecules, which is inapplicable for the purposes of detection of analytes.

The invention also allows the identification of novel substrates and determination of their kinetic parameters $K_M$ a $k_{cat}$. This is performed so that the detection probe is incubated with the enzyme in the presence of various concentrations of tested substance. In case that the substance is a substrate, there will be not only displacement of the probe from the active site characterized by its $K_i$, but also an apparent decrease of the $K_i$ with decreasing concentrations of the tested substance, because at these concentrations a substantial portion of the substance is cleaved by the enzyme. It is obvious that the $K_i$ measured at higher substance concentrations, where there is no change of the $K_i$ value with changing concentration of the tested substance, corresponds to $K_M$. For $k_{cat}$ calculation then applies:

$$k_{cat}=(S_0-S_t+K_M*\ln(S_0/S_t))/(E_{tot}*t) \qquad (17),$$

where $S_0$ is the initial concentration of the tested substance, $S_t$ is the concentration of the substance in time t and t is the incubation time of the substance with the enzyme. Concentration $S_t$ is calculated from the $\Delta C_q$ measured during incubation with tested substances (at initial concentration $S_0$) according to the equation 15, wherein is $K_M$ substituted for $K_i$ and the equation is solved for $I_{tot}$ that corresponds to $S_t$. A prerequisite of this solution is the lower affinity of the product or products of the enzyme reaction in comparison with the substrate or substrates. The process is particularly advantageous because the new substrates are detected using a universal readout (qPCR) and is therefore not necessary to develop individual methods of detection suitable for each product or substrate.

A method is described in this application, wherein the upper antibody of the antibody sandwich used in ELISA is replaced with a fully synthetic probe composed of a low molecular compound for selective binding to the active site of the analyte and a covalently linked (by a linker) oligonucleotide tag that serves to quantify the analyte. Advantageously, e.g. known enzyme inhibitors, receptor agonists or antagonists, transporter agonists, or their transported substances can be used as selectively binding part of the probe.

In addition to exceptional sensitivity, documented by the detection limit of prostate specific membrane antigen (PSMA antigen distinct from the PSA) in the order of only tens of molecules, this method offers the extreme dynamic range of more than six orders of magnitude, which is 3-4 orders of magnitude more than in ELISA.

Furthermore, thanks to the probe binding to the active site of the analyte, this method enables measuring of the affinity of the tested substances to the active site of the analyte. In conjunction with the large dynamic range the described process allows to provide the value of the inhibition constant of the tested substances from only one measurement and using a single concentration of tested substance. Due to the high sensitivity and selectivity of the method it is not necessary to prepare a recombinant analyte, as the analyte contained in a biological matrix, e.g. blood or a cell or tissue lysate, is fully sufficient. The aforementioned advantages of the method for determination are unique and are demonstrated here not only for PSMA protein, but also for other enzymes. Finally, thanks to the fact that the described method is suitable for automation, it is industrially applicable for routine in vitro diagnostic and "high throughput screening" (HTS) of inhibitors and substrates of enzymes, agonists and antagonists of receptors or antagonists and transported substances of transporters.

Described processes allowed to prepare detection probes selectively binding to the active sites of a variety of enzymes. Said detection probes consisted of a compound for selective binding to the active sites of these enzymes connected to an oligonucleotide tag via chemical linker. The compound was either a selective inhibitor of the enzyme, or a selective inhibitor of a group of enzymes, which includes the tested enzyme. In combination with a suitable immobilization of the enzyme, either selective or nonselective, the detection probes were successfully used for a sensitive detection of these enzymes, as well as for testing the bond strength of substances in the active sites of these enzymes.

With selective immobilization via antibody and detection probe with covalently bound (S, S-2-(3-(5-amino-1-carboxy-pentyl)-ureido) pentan-1,5-dioic acid) selectively binding to the active site of human PSMA, we were able to quantify PSMA in the concentration range of more than six orders of magnitude, with a detection limit of 10 attograms, which corresponds to approximately 34 molecules of PSMA dimer. This limit of detection is at least a millionfold improvement over the most sensitive methods for detection of PSMA available until now. To reach such an ultrasensitive detection and large range, quantitative polymerase chain reaction was used, but alternative preferable detection methods can also be used, particularly chemiluminescent, because even with that detection method, the sensitivity of PSMA determination was at least ten times higher than today's most sensitive methods. PSMA was detected and quantified with the same sensitivity and dynamic range in various matrices, in addition to the recombinant purified protein diluted in buffer it was PSMA naturally contained in human blood, human urine or tissue and cell lysates. The volume of only 10 nl of human blood plasma was sufficient for a reliable determination of PSMA concentration. When the detection probe was incubated with the analyte in presence of a tested substance potentially binding to the active site of PSMA, we managed to determine the bond strength to the active site of PSMA (corresponding to $K_i$) of all tested substances with great precision. Wide linear range of the assay allowed to determine the $K_i$ of these substances from a single tested concentration in the range of more than six orders of inhibitory constant. High sensitivity allowed to determine the $K_i$ of these substances (in the same manner and with great precision) also for naturally occurring PSMA in human blood at a negligible consumption of biological material (1 µl of plasma per tested substance). The possibility of suppressing the selective binding of detection probe by simultaneous incubation with another substance binding to the active site further represents a simple control of accuracy of the signal obtained in detection of PSMA in a complex biological matrix, in particular blood plasma or serum. The detection probe selectively binds with similar affinity as for PSMA also to the active site of human glutamate carboxypeptidase III, protein closely related to PSMA. It was shown that using an antibody selectively binding PSMA, the entire detection was selective for PSMA and presence of GCPIII did not interfere with the detection at concentrations of up to six orders of magnitude higher than the concentration of PSMA.

With selective immobilization via expression tag and using the same detection probe we managed to detect and quantify the amount of recombinantly prepared proteins PSMA and GCPIII with great sensitivity and also determine (in a wide range and with high precision) the bond strength of all tested substances to the active sites of both proteins from a single concentration of the tested substances.

Very sensitive detection is achieved also by selective immobilization via antibody and detection probe with a compound derived from a covalently binding peptide inhibitor containing a boronic group also for the human prostate specific antigen (PSA). Sensitivity of the assay is less than 1 pg of PSA, and the PSA has been quantified in various matrices; in addition to the purified PSA diluted in buffered solution, PSA has been quantified in blood plasma and serum.

Similarly, a selective and sensitive detection of human-fibroblast activating protein (FAP) and human dipeptidyl peptidase 4 (DPP-4) in solution, cell and tissue lysates, urine, blood plasma and serum was achieved. In combination with an immobilized selective antibody, the assay was selective for each of the protein, even when using a compound binding to active site of both the proteins. This method also allows the quantitative determination of the ability of the tested substances to bind to the active sites of both proteins and thereby determining their selectivity.

We also succeeded to quantify HIV protease in a solution (either with selective immobilization via an antibody or with direct non-selective immobilization on a surface) and with great precision determine the bond strength to the active site of HIV protease of all the tested substances. The bond strength of the substances was determined at various pH levels. Used detection probe contained a compound derived from clinically used inhibitor Ritonavir.

Similarly, using an immobilized antibody, we managed to determine the amount of influenza neuraminidase with great sensitivity. The detection probe was prepared by covalently attaching the compound 1-(6-Azidohexyl)-(3R,4R,5S)-4-acetyl amino-5-N-tert-butoxycarbonyl-amino-3-(1-ethyl-propoxy)-1-cyclohexene-1-phosphonate to the oligonucleotide tag. Sensitivity of the assay was less than 1 pg of neuraminidase N1 originating from pandemic virus A/California/07/2009, and the neuraminidase has been measured in various biological matrices.

Another detection probes were prepared by covalently attaching an oligonucleotide tag to the compounds selectively binding to the active site of human carbonic anhydrases, especially carbonic anhydrase IX (CA-IX). In combination with the selective immobilization of CA-IX via a monoclonal antibody, a highly sensitive determination of CA-IX in solution and in a variety of biological matrices, particularly in tissue and cell lysates, as well as in blood plasma and serum, was achieved. Incubating the detection probe with CA-IX in the presence of tested substances allowed to determine the bond strength, i.e. inhibition constants, of all these substances with high accuracy.

Using bivalent probes, we obtained a sensitivity of less than 10 fg CA-IX in a cell or tissue lysate, urine, blood serum or plasma; and in a set of blood serums taken from healthy donors, and from patients with prostate cancer or clear-cell renal carcinoma, it was found that the concentration of CA-IX differed significantly between the groups and thus might be used for the diagnosis of these malignancies. Furthermore, we developed a method for highly efficient testing (HTS) of inhibitors with unpurified endogenous CA-IX contained in a cell lysate or in microliter volumes of serum. This is a unique method, because despite medical importance of carbonic anhydrase inhibitors, such kind of assay has not been developed, even using a purified recombinant protein, let alone with unpurified endogenous protein.

Similarly prepared were the detection probes of human CA-XII, and in combination with the selective immobilization of CA-XII through a monoclonal antibody, a highly sensitive determination of CA-XII in solution and in a variety of biological matrices, particularly tissue and cell lysates, urine, blood plasma and serum was achieved. A method for highly efficient testing (HTS) of CA-XII inhibitors was also developed.

Said exceptional sensitivities of detection of various analytes are achieved not only by finding suitable additives, which suppress non-selective adsorption of the detection probe in the incubation step of the solid carrier with the detection probe, but particularly by successful preparation of tightly binding to detection probes. In many cases, we surprisingly succeeded to prepare detection probes binding equally tightly, or even more tightly than the parent compound for selective binding to the active site of the analyte, despite major intervention into the structure of the compound by covalently attaching a chemical linker for conjugation to an oligonucleotide tag. For example, the inhibitory constant was 200 pmol·l$^{-1}$ for the PSMA parent compound without a linker, whereas 3.3 nmol·l$^{-1}$ for the compound with a linker and 140 pmol·l$^{-1}$ after conjugation to an oligonucleotide tag (Example 1c). While connecting a linker worsened the affinity of the compound as expected, attaching an oligonucleotide tag surprisingly improved the affinity even above the level of the parent compound. A similar effect was achieved in the preparation of detection probes for other analytes, too; e.g. HIV protease ($K_i$ of original substance ritonavir was 15 pmol·l$^{-1}$, a substance with a linker 2.3 nmol·l$^{-1}$, detection probe 0.23 nmol·l$^{-1}$) and influenza neuraminidase ($K_i$ of original substance oseltamivir was 24 nmol·l$^{-1}$, a substance with a linker 24 nmol·l$^{-1}$, detection probe 0.79 nmol·l$^{-1}$) wherein the detection probe was binding to neuraminidase active site by more than one order of magnitude more tightly than the parent compound oseltamivir. High-affinity probe for dimeric CA-IX protein was prepared by connecting two molecules of the compound to one oligonucleotide tag, and due to the avidity, affinity was increased by more than an order of magnitude ($K_d$ of bivalent detection probe was 2.1 nmol·l$^{-1}$ compared to $K_d$ of monovalent probe 70 nmol·l$^{-1}$), which was possible, inter alia, because even in this case, connecting oligonucleotide tag did not decrease the affinity, as the $K_d$ of the compound with a linker itself (Compound 14) was 300 nmol·l$^{-1}$.

BRIEF DESCRIPTION OF THE DRAWINGS

FIG. 3A illustrates a situation where the solid carrier with bound enzyme is incubated only with a detection probe; signal measured in qPCR is then proportional to the amount of bound enzyme (bottom).

FIG. 5 shows the structure of a detection probe for selectively binding PSMA (ssPSMA). The nucleotides within the oligonucleotide tag sequence are listed using the single letter code.

FIG. 6 shows a mass spectrum (mass over charge is plotted on x-axis) measured in LC/ESI-MS analysis of the detection probe selective for PSMA (ssPSMA). The calculated mass determined from the described peaks is 17426.84.

EXAMPLES

Figure 1:
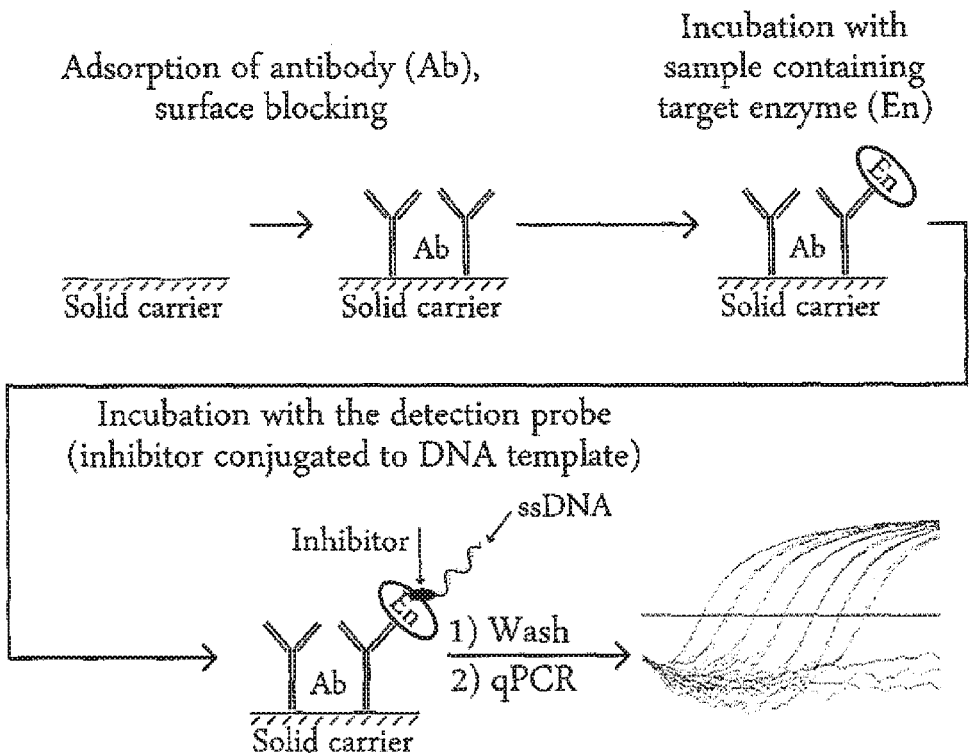
FIG. 1 shows the principle of the method for selective quantification of enzyme. Ab is an antibody immobilized on a solid carrier, En is an enzyme contained in the sample recognized by the antibody.
Figure 2:
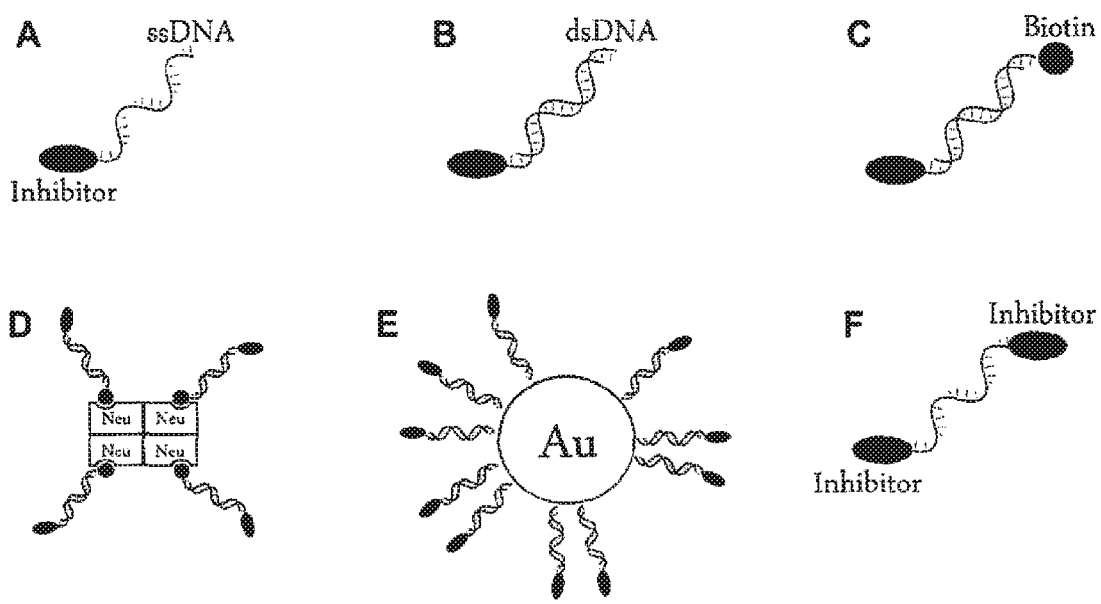
FIG. 2A-F shows a possible composition of a detection probe consisting of a compound for selective binding to the active site of the analyte (here inhibitor), covalently linked to an oligonucleotide tag that is detected by qPCR. Oligonucleotide tag may be single-stranded DNA (ssDNA; A), double-stranded DNA (dsDNA; B), optionally contains fluorophores or biotin (C). Biotin on the detection probe can be used to form tetravalent particles after binding to a tetrameric biotin-binding protein, such as neutravidin (Neu), (D), optionally with covalently bound fluorophores or enzymes for alternative detection. The detection probe can also be bound to the surface of gold nanoparticles (Au), (E). To achieve higher avidity, two or more molecules of the same compound for selective binding of the analyte can be individually covalently linked into different positions of the oligonucleotide tag (F).
Figure 3:
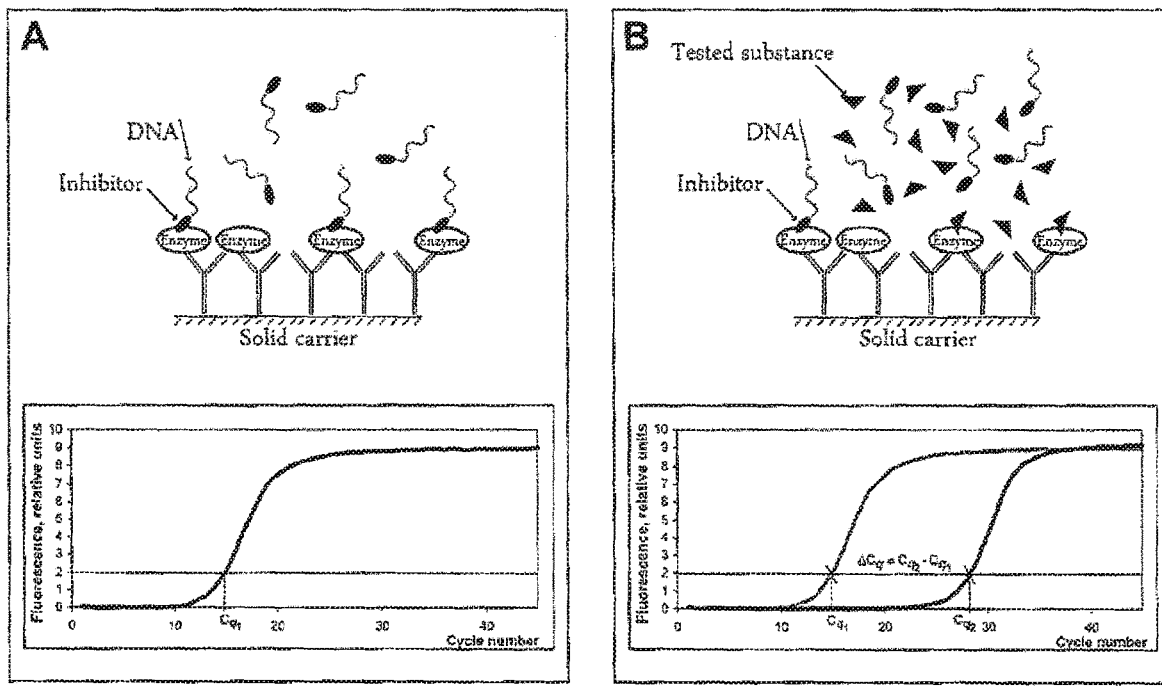
FIG. 3A,B shows the principle of determining the binding potency of the tested substances to bind to the active sites of analytes.
FIG. 3B shows a situation where the solid carrier with bound enzyme is incubated with a mixture of the detection probe and a tested substance. If the tested substance binds to the active site, the amount of bound detection probe proportionally decreases, which results in higher $C_q$ measured by qPCR, and the ratio of the remaining free enzyme to the total amount of the enzyme is proportional to the difference of $C_q$ values during incubation with the tested substance and without it.
Figure 4:
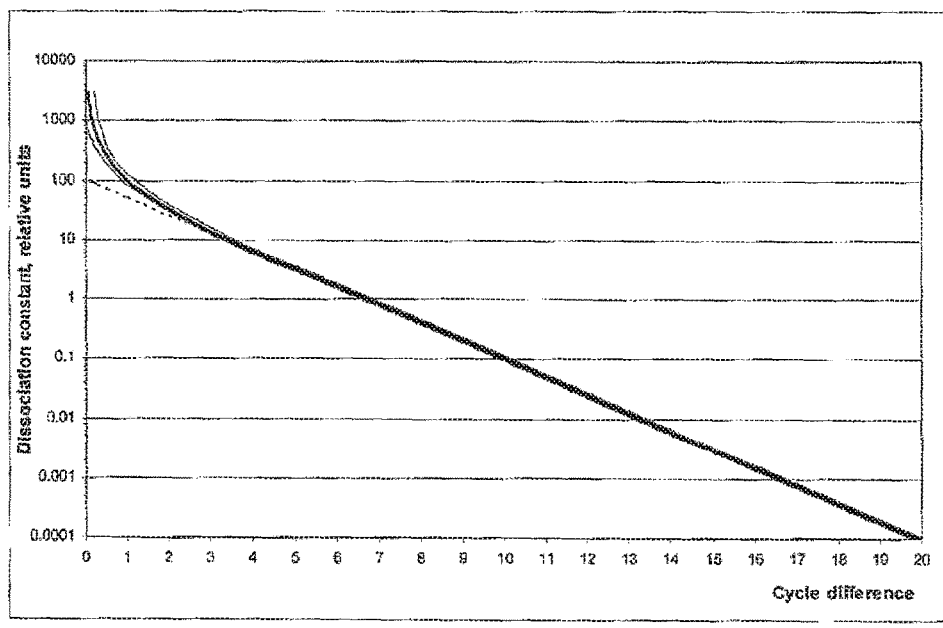
FIG. 4 shows the accuracy of the determined dissociation constant of the tested substance (y-axis) in dependence on the measured difference between the number of cycles after incubation of the analyte with the detection probe with the tested substance and without it ($\Delta C_q$, x-axis), bold line plots the determined dissociation constant of the tested substance as a function of the measured $\Delta C_q$. Logarithm of the dissociation constant for large $\Delta C_q$ values is directly proportional to that $\Delta C_q$. For small $\Delta C_q$ values, dependence deviates from linearity; significant deviation is observed for $\Delta C_q$ lower than one; thin dashed line then shows a direct correlation. Thin grey lines show the value of the dissociation constant +− standard deviation of its determination.

Composition of Solutions
Modification buffer 100 mmol·l$^{-1}$ phosphate buffer; 150 mmol·l$^{-1}$ NaCl; pH=7.8
TBS 20 mmol·l$^{-1}$ Tris; 150 mmol·l$^{-1}$ NaCl; pH=7.4
TBST 20 mmol·l$^{-1}$ Tris; 150 mmol·l$^{-1}$ NaCl; pH=7.4; 0.05% Tween20 (vol./vol.)
TBST200 20 mmol·l$^{-1}$ Tris; 200 mmol·l$^{-1}$ NaCl; pH=7.4; 0.05% Tween20 (vol./vol.)
TSBT' 20 mmol·l$^{-1}$ Tris; 150 mmol·l$^{-1}$ NaCl; pH=7.4; 0.1% Tween20 (vol./vol.)
CaSDS 20 mmol·l$^{-1}$ Tris; 150 mmol·l$^{-1}$ NaCl; pH=7.4; 0.1% Tween20 (vol./vol.); 0.005% SDS (hm./obj.); 500-fold diluted casein blocker (SDT; cat. no. CBC1)
TBSE 20 mmol·l$^{-1}$ Tris; 150 mmol·l$^{-1}$ NaCl; pH=7.4; 5 mmol·l$^{-1}$ EDTA
MEST 20 mmol·l$^{-1}$ MES; 750 mmol·l$^{-1}$ NaCl; pH 6.0; 0.05% Tween20 (vol./vol.)
CLP 50 mmol·l$^{-1}$ Tris; 100 mmol·l$^{-1}$ NaCl; pH 7.4
HEPESTC 100 mmol·l$^{-1}$ HEPES; 400 mmol·l$^{-1}$ NaCl; pH=7.5; 0.01% Tween20 (vol./vol.); 2000-fold diluted casein blocker (SDT; cat. no. CBC1)
HEPESTC' 100 mmol·l$^{-1}$ HEPES; 400 mmol·l$^{-1}$ NaCl; pH=7.5; 0.1% Tween20 (vol./vol.); 500-fold diluted casein blocker (SDT; cat. no. CBC1)

Explanation of Terms and Abbreviations

GCPII glutamate carboxypeptidase II
PSMA prostate specific membrane antigen
Avi-PSMA protein consisting of extracellular part of prostate specific membrane antigen with N-terminally attached Avi-tag
rhPSMA recombinant human prostate specific membrane antigen
GCPIII glutamate carboxypeptidase III
Avi-GCPIII protein consisting of extracellular part of glutamate carboxypeptidase III with N-terminally attached Avi-tag
ssPSMA designation of detection probe for the detection of PSMA (containing single stranded oligonucleotide tag)
dsPSMA designation of detection probe for the detection of PSMA (containing double stranded oligonucleotide tag)
dsA3PSMA designation of detection probe for the detection of PSMA (containing double stranded oligonucleotide tag)
dsbiotPSMA designation of detection probe for the detection of PSMA (containing biotinylated double stranded oligonucleotide tag)
Neu_dsbiotPSMA designation of detection probe for the detection of PSMA (containing biotinylated double stranded oligonucleotide tag bound to neutravidin)
NeuHRP_dsbiotPSMA designation of detection probe for the detection of PSMA (containing biotinylated double stranded oligonucleotide tag bound to neutravidin conjugated with peroxidase)
ssHIV designation of detection probe for the detection of HIV protease (containing single stranded oligonucleotide tag)

CA-II carbonic anhydrase II
CA-IX carbonic anhydrase IX
ssCA designation of detection probe for the detection of carbonic anhydrases (containing single stranded oligonucleotide tag)
ssCAbis designation of bivalent detection probe for the detection of carbonic anhydrases
Neu_dsbiotCA designation of detection probe for the detection of carbonic anhydrases (containing biotinylated double stranded oligonucleotide tag bound to neutravidin)
ssAP designation of detection probe for the detection of aspartic proteases (containing single stranded oligonucleotide tag)
ssAD designation of oligonucleotide with bound DBCO
ssAD_NA designation of detection probe for the detection of influenza neuraminidases
eq equivalent
RT retention time
Tween 20 polyoxyethylene (20) sorbitanmonolaurate (USB, cat. no. 20605)
DIAD diisopropyl azodicarboxylate
DBCO dibenzyl cyclooctyne
HEPES N-2-hydroxyethylpiperazine-N'-2-ethanesulfonic acid
SDS sodium dodecyl sulfate
SDS-PAGE polyacrylamide gel with sodium dodecyl sulfate for electrophoresis
LC-MS liquid chromatography-mass spectrometry
ESI electrospray ionisation
FBS fetal bovine serum
THF tetrahydrofuran
DMF dimethylformamide
DIEA diisopropylethylamine
ACN acetonitrile
TFA trifluoroacetic acid
DPPA diphenylphosphorylazide
TEA triethylamine
PEG5 5 linked ethylene glycol units
HOBT/DIC hydroxybenzotriazole/diisopropylcarbodiimide
AAZ acetazolamide
DCC dicyclohexylcarbodiimide
DCU dicyclohexylurea
TBTU O-(Benzotriazol-1-yl)-N,N,N',N'-tetramethyluronium tetrafluoroborate
HRMS high resolution mass spectrometry

Example 1: Quantification of PSMA, Testing of PSMA Inhibitors Potency

1a: Preparation of PSMA Inhibitor with a Linker and an Activated NHS Ester

The detection probe for PSMA was prepared by linking of an urea based PSMA inhibitor S,S-2-[3-[5-amino-1-carboxypentyl]-ureido]-pentanedioic acid to the DNA. Following derivatives of the inhibitor were prepared: inhibitor with linker with terminal NHS-ester (Compound 3) for linking to the amino group of the DNA oligonucleotide and this compound reacted with ethanolamine (Compound 4) for determination of the impact of linking of the DNA oligonucleotide on the inhibition potency.

All chemicals were purchased from Sigma-Aldrich, unless stated otherwise. The purity of compounds was tested on analytical Jasco PU-1580 HPLC (flow rate 1 ml/min, invariable gradient 2-100% (vol./vol.) ACN in 30 minutes, RT shown for each compound) with column Watrex C18 Analytical Column, 5 μm, 250×5 mm. All final products were purified using preparative scale HPLC Waters Delta 600 (flow rate 7 ml/min, gradient and RT shown for each compound) with column Waters SunFire C18 OBD Prep Column, 5 μm, 19×150 mm. All final products were of at least 99% purity. Structure of the final products was further confirmed by HRMS at LTQ Orbitrap XL (Thermo Fisher Scientific) and by NMR (Bruker Avance I™ 500 MHz equipped with Cryoprobe or Bruker Avance I™ 400 MHz).

Preparation of 3,3'-oxydipropanoic acid (Compound 1): 2.38 ml (20 mmol) of 3,3'-oxydipropanenitrile was dissolved in 7 ml of concentrated HCl and was heated to 50° C. for 24 hours. The reaction mixture was then left to cool down overnight and the hydrochloric acid was removed by flow of nitrogen. The resulting slurry was dissolved in water and lyophilized; 2.25 g of white product was obtained (yield=70%). The spectral analysis of this product was identical to that described in (White et al. 2003, Tetrahedron-Asymmetry, p. 3633).

Preparation of bis(2,5-dioxopyrrolidin-1-yl) 3,3'-oxydipropanoate (Compound 2): To a solution of Compound 1 (260 mg, 1.6 mmol, 1 eq) and N-hydroxy succinimide (660 mg, 3.2 mmol, 2 eq) in 10 ml of THF, solid DCC (368 mg, 3.2 mmol, 2 eq) was added in one portion. The reaction was left overnight, after which the DCU was filtered of and the volatiles rotary evaporated. The crude product was further purified by chromatography (He:EtOAc 1:2); 338 mg of pure product obtained (isolated yield=60%). Analytical HPLC RT=16.2 min.

Result of analysis by $^1$H NMR (400 MHz, CDCl$_3$): δ 3.85 (t, J=6.4 Hz, 4H), 2.90 (t, J=6.4 Hz, 4H), 2.83 (bs, 8H).

Result of analysis by $^{13}$C NMR (101 MHz, CDCl$_3$): δ 169.07, 166.77, 65.78, 32.20, 25.73.

Result of analysis by HRMS (ESI+): calculated mass of $C_{14}H_{16}O_9N_2$ [MNa]$^+$ 379.07480, detected mass 379.07469.

Preparation of 19-((2,5-dioxopyrrolidin-1-yl)oxy)-5,13,19-trioxo-16-oxa-4,6,12-triazanonadecane-1,3,7-tricarboxylic acid (Compound 3): To a stirring solution of Compound 2 (69 mg, 193 μmol, 1.2 eq) dissolved in 1 ml of DMF, a solution of di-tert-butyl 2-(3-(6-amino-1-(tert-butoxy)-1-oxohexan-2-yl)ureido)pentanedioate (100 mg, 161 μmol, 1.0 eq, prepared as described in (Murelli et al. 2009, Journal of the American Chemical Society, str. 17090)) and DIEA (34 μl, 193 μmol, 1.2 eq) in 1 ml of DMF was added dropwise during 1 hour. The reaction mixture was left stirring for 2 hours after which an HPLC analysis proved total disappearance of reactants. The solvents were then removed by rotary vacuo and the compound was fully dried. 1 ml of TFA was then added into the crude mixture to yield title compound, after 1 hour incubation at room temperature the trifluoracetic acid was removed by flow of nitrogen. The crude product was purified using preparative HPLC (gradient 5-50% (vol./vol.) ACN in 40 minutes, RT 18 minutes); 20 mg of the product was obtained (isolated yield=22%). Analytical HPLC RT=13.7 min.

Result of analysis by $^1$H NMR (500 MHz, DMSO-d6): δ 7.80 (t, J=5.6, 1H, NH-Lys-6), 6.32 (d, J=8.3, 1H, NH-Glu-2), 6.29 (d, J=8.2, 1H, NH-Lys-2), 4.09 (m, 1H, Glu-2), 4.03 (m, 1H, Lys-2), 3.55 (m, 4H, O—CH$_2$—CH$_2$—COO, Lys-CO—CH$_2$—CH$_2$—O), 3.00 (m, 2H, Lys-6), 2.80 (bs, 4H, CO—CH$_2$—CH$_2$—CO), 2.41 (t, J=6.3, 2H, O—CH$_2$—CH$_2$—COO), 2.31-2.20 (m, 4H, Lys-CO—CH$_2$—CH$_2$, Glu-4), 1.91 (m, 1H, Glu-3b), 1.71 (m, 1H, Glu-3a), 1.63 (m, 1H, Lys-3b), 1.51 (m, 1H, Lys-3a), 1.37 (m, 2H, Lys-5), 1.26 (m, 2H, Lys-4).

Result of analysis by $^{13}$C NMR (125.7 MHz, DMSO-d6): δ 174.77 (Lys-1), 174.40 (GLu-1), 173.95 (Glu-5), 172.89 (O—CH$_2$—CH$_2$—COO), 170.39 (CO—NH—CO), 170.00

(lys-CO—CH$_2$—CH$_2$—O), 157.52 (NH—CO—NH), 66.87 (lys-CO—CH$_2$—CH$_2$—O), 66.07 (O—CH$_2$—CH$_2$-000), 52.46 (Lys-2), 51.85 (Glu-2), 38.54 (Lys-6), 36.25 (Lys-CO—CH$_2$—CH$_2$—O), 34.84 (O—CH$_2$—CH$_2$-000), 31.97 (Lys-3), 30.09 (Glu-4), 29.00 (Lys-5), 27.71 (Glu-3), 25.66 (CO—CH$_2$—CH$_2$-00), 22.82 (Lys-4).

Result of analysis by HRMS (ESI+): calculated mass of C$_{22}$H$_{32}$O$_{13}$N$_4$ [MNa]$^+$ 583.18581; detected mass 583.18596.

Preparation of 1-hydroxy-4,10,18-trioxo-7-oxa-3,11,17,19-tetraazadocosane-16,20,22-tricarboxylic acid, Compound 4: 5 mg (9.87 µmol, 1 eq) of Compound 3 were dissolved in 200 µl of DMF and 6 µl (99 µmol, 10 eq) of ethanolamine was added into the mixture along with 14 µl (80.4 µmol, 8 eq) of DIEA and the mixture was left stirring overnight. The solvent was rotary evaporated and the mixture was dissolved in ACN/water and lyophilized three times (to evaporate the remaining ethanolamine). The compound was used in biochemical studies without further purification (the only contaminant is NHS, otherwise purity was higher than 95%). Analytical HPLC RT=11.3 min.

Result of analysis by HRMS (ESI+): calculated mass of C$_{20}$H$_{33}$O$_{11}$N$_4$ [M]$^+$ 505.21513, detected mass 505.21515.

1b: Preparation of a Detection Probe for Selective Binding to PSMA

Detection probe for selective binding to PSMA was prepared by reacting of Compound 3 and single-stranded DNA with the 3'-terminal 6-amino-2-(hydroxymethyl)hexyl phosphate modification and the sequence CCT GCC AGT TGA GCA TTT TTA TCT GCC ACC TTC TCC ACC AGA CAA AAG CTG GAA A (SEQ ID NO: 1) (custom synthesis Generi-Biotech, OPC purification).

Oligonucleotide (hereinafter referred to as iqPCR_amino) was dissolved in double distilled water at a concentration of 1 mmol·l$^{-1}$, and subsequently, for part of the solution, water was replaced with 100 mmol·l$^{-1}$ phosphate buffer solution with 150 mmol·l$^{-1}$ NaCl (p.a.; Penta), at pH 7.8 (hereinafter "modification buffer") by repeated ultrafiltration on Amicon Ultra 0.5 ml 3K column (Millipore, cat. no. UFC500396). The rest of the solution was treated the same, but after each step of ultrafiltration, it was diluted with solution of double distilled water. In both cases, the total dilution of the original solvent was 10$^5$ fold. The concentration of oligonucleotide in the resulting solution was calculated from the measured absorbance at 260 nm (Nanodrop ND-1000, Thermo Scientific) and the estimated optical density of oligonucleotide solution 1 OD=1744 pmol.

To verify the identity and purity, the solution of iqPCR_amino in distilled water was analyzed with LC/ESI-MS method in the Agilent 6230 TOF LC/MS device (Agilent Technologies) equipped with dual AJS ESI source in the settings for detecting negative ions (4 GHz, HiRes). Separation was carried out at room temperature on Agilent Zorbax Extend-C18 1.8 µm (2.1×50 mm) column by gradient elution in changing ratio of HFIP solution (200 mmol·l$^{-1}$ aqueous solution of 1,1,1,3,3,3-hexafluoro-2-propanol, pH adjusted to 7.0 by addition of triethylamine) and acetonitrile, at a flow rate of 0.3 ml·min$^{-1}$ (2-45% (vol./vol.) ACN in 6 minutes). The result of the analysis of 5 pmol iqPCR_amino was a single absorption peak at 260 nm and a retention time of 4.84 min and the measured mass (calculated from the most intense peaks for each of the charge z) 16981.87; the most abundant mass predicted with ChemBioDraw Ultra 13.0.0.3015 program (CambridgeSoft) is 16979.91 for the molecular weight of 16983.09.

Preparation of a conjugate of the oligonucleotide (iqPCR_amino) with PSMA inhibitor (Compound 3): 6.9 µl of 1 mol·l$^{-1}$ HEPES buffer, pH=8.0, was added to 10 µl of the oligonucleotide in the modification buffer (10.2 nmol, 1 eq) and after stirring, 3.1 µl of a solution of compound 3 at a concentration of 100 mmol·l$^{-1}$ in anhydrous DMSO (307 nmol, 30 eq) was added. Anhydrous DMSO was prepared by several hours incubating of DMSO (Sigma, A.C.S. spectrophotometric grade) with activated molecular sieves (Sigma, cat. No. 688363) at continuous shaking. The molecular sieves were then removed by a brief centrifugation at 16000 g.

The resulting mixture was incubated at room temperature for 24 hours, diluted to 500 µl with distilled water and then applied to Amicon Ultra 0.5 ml 10K column (Millipore, cat. No. UFC501096) for purification from the hydrolysis products of Compound 3. Through repeated concentrating by ultrafiltration on the column and repeated dilutions, the original solvent (together with the hydrolysis reaction products) was diluted 10$^{10}$-fold with double distilled water. This way we obtained 43 µl of solution with oligonucleotide concentration of 215 pmol·µl$^{-1}$ determined by absorbance at 260 nm (9.2 nmol, 90% yield); the resulting product is hereinafter called ssPSMA, and its predicted structure is shown in FIG. 5.

To verify the efficiency of conjugation, ssPSMA was analyzed by LC-MS, the procedure was identical to the original iqPCR_amino (described above in this section), and the result was a single peak with absorbance at 260 nm, retention time 4.85 min (i.e. the same retention time as the original iqPCR_amino) and the measured mass (calculated from the most intense peaks for each of the charges z) was 17426.84 (FIG. 6); while the most abundant mass predicted is 17425.08 for the molecular weight of 17428.52. The difference between the measured mass of conjugate ssPSMA and the original oligonucleotide iqPCR_amino is 444.97 compared to the expected difference 445.17. Ratio of mass over charge corresponding to the original iqPCR_amino were not detectable in the spectra, which means that converting significantly exceeded 90%.

The ssPSMA solution was also analyzed for the presence of residual products of hydrolysis of Compound 3, in particular 6,14-dioxo-3-oxa-7,13,15-triazaoctadecan-1,12,16,18-tetracarboxylic acid. This compound obviously binds to the active site of PSMA and if it occurred in the sample in a similar or greater amount than the actual probe, it might compete with the probe for binding and thus reduce the sensitivity of the PSMA assay. The analysis itself was performed by LC-MS in the same manner as described above, with the use of Waters Acquity C18 BEH column 1.8 µm (100×2.1 mm), mobile phase 0.1% (vol./vol.) formic acid and acetonitrile. Elution gradient was 2-100% (vol./vol.) ACN in 6 minutes, and during the whole elution, no signal was detected corresponding at least approximately (±0.2) to the estimated mass 463.18 (m/z=462.18).

The ssPSMA conjugate, as well as the original oligonucleotide iqPCR_amino, was diluted prior to use in bioassays to a final concentration of 5 nmol·l$^{-1}$ in water and 10× concentrated TBS buffer (final concentration 1×TBS: 20 mmol·l$^{-1}$ Tris, 150 mmol·l$^{-1}$ NaCl, pH=7.4). In a volume of 50 µl in a thin-wall polypropylene eppendorf PCR tube the (Biotix, cat. No. 3423.AS) it was exposed to to the following temperature cycle (hereinafter thermal annealing) in a Tgradient Biometra thermocycler (Labrepco): rapid heating to 98° C., followed by repeated cooling by increments of 1° C. (0.2° C./s) and remaining for 5 min in each step; after reaching a temperature of 60° C., repeated cooling by increments of 5° C. (0.2° C./s) followed and remaining for 5 min in each step until reaching 20° C.; the temperature of the lid was set to 99° C. during the entire procedure.

Figure 7:
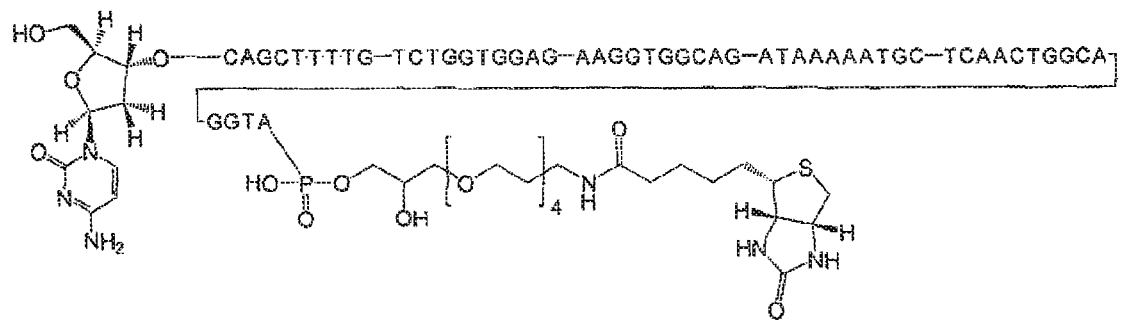
FIG. 7 shows a 3'-terminally modified oligonucleotide complementary to iqPCR_amino. At the 3' terminus of single-stranded DNA, biotin (2-hydroxy-18-oxo-22-((3aS, 4S,6aR)-2-oxohexahydro-1H-thieno[3,4-d]imidazole-4-yl)-4,7,10,13-tetraoxa-17-azadocosyl phosphate) is bound via a chemical linker.

Detection probes with double-stranded oligonucleotide tags were prepared in a similar manner: before thermal annealing, the ssPSMA conjugate was mixed in approximately equimolar ratio successively with several different complementary oligonucleotides. The dsPSMA detection probe was formed by mixing ssPSMA with single-stranded DNA sequence TTT CCA GCT TTT GTC TGG TGG AGA AGG TGG CAG ATA AAA ATG CTC AAC TGG CAG G (SEQ ID NO: 2)(optical density of the complementary strand solution used for calculation of its concentration: 1 OD=1649 pmol); the dsA3PSMA detection probe was formed by mixing ssPSMA with single-stranded DNA sequence CCA GCT TTT GTC TGG TGG AGA AGG TGG CAG ATA AAA ATG CTC AAC TGG CAG G (SEQ ID NO: 3) (1 OD=1721 pmol); whereas the detection probe dsbiotPSMA probe was formed by mixing ssPSMA with single-stranded DNA (hereinafter iqPCR_biotin) sequence CCA GCT TTT GTC TGG TGG AGA AGG TGG CAG ATA AAA ATG CTC AAC TGG CAG GTA (SEQ ID NO: 4) (1 OD=1639 pmol), 3'-terminally biotinylated; the structure of this modification is shown in FIG. 7.

1c: Determination of the Inhibition Constants of the Compounds Prepared and the Detection Probes Biotinylated extracellular portion of PSMA (hereinafter called Avi-PSMA) used in the enzyme assay was prepared and purified according to (Tykvart et al. 2012, Protein Expression and Purification, p. 106); the concentration of pure recombinant protein was determined by amino acid analysis on the Biochrom30 device (Biochrom) according to the manufacturer's instructions. The enzyme was then stored frozen in aliquots at −80° C. The concentration of oligonucleotides was determined spectrophotometrically (see above), the concentration of Compound 4 was derived from the weight on an analytical balance (dissolved in distilled water).

$IC_{50}$ values of all compounds were determined using a method based on HPLC. In a 96 well plate, 0.2 ng Avi-PSMA in 25 mmol·l$^{-1}$ Bis-Tris propane, 150 mmol·l$^{-1}$ NaCl, 0.001% (wt./vol.) octaethyleneglycol monododecyl ether ($C_{12}E_8$), pH 7.4 (hereinafter referred to as a reaction buffer) were mixed together with the tested inhibitor in a total volume of 180 µl. Ten different inhibitor concentrations in a quad dilution series were used to determine the inhibition curve. Reactions were preincubated at 37° C. for 5 min and then started by adding 20 µl 4 µmol·l$^{-1}$ pteroyl-bis-L-glutamate (Schircks Laboratories) and incubated at 37° C. for an additional 20 min. The enzymatic reaction was stopped by adding 20 µl of 25 µmol·l$^{-1}$ inhibitor 2-PMPA (2-(phosphonomethyl) pentanedioic acid (Jackson et al., 1996, Journal of Medicinal Chemistry, p. 619)).

Subsequently, 100 µl of the reaction mixture was analyzed by HPLC on an Agilent 1200 Series device equipped with UPLC HSS T3 column 1.8 µm (2.1×100 mm, Waters). Elution itself was isocratic in 2.7% (vol./vol.) acetonitrile and 97.3% (vol./vol.) 20 mmol·l$^{-1}$ phosphate, pH=6.0 at a flow rate of 0.4 ml·min'. Substrate and product absorbances were detected at 281 nm, their amounts were determined by automatic integration. The obtained data were evaluated in GraFit v.5.0.11 program (Erithacus Software) and thus the $IC_{50}$ values were obtained.

The kinetic parameters ($K_M$ and $k_{cat}$) of pteroyl-bis(L-glutamate) Avi-PSMA cleavage in the reaction buffer were determined according to the procedure described above without the added inhibitor, with various substrate concentrations ranging from 15 nmol·l$^{-1}$ to 400 nmol·l$^{-1}$, wherein the conversion of all reactions was 13±2%. These parameters were then used, assuming competitive inhibition, to convert values of measured $IC_{50}$ to values of the inhibition constants ($K_i$) according to the Cheng-Prusoff equation (Cheng et al., 1973, Biochemical Pharmacology, p. 3099).

The resulting $K_i$ value of the Compound 4 was 3.3 nmol·l$^{-1}$, $K_i$ of the original iqPCR_amino oligonucleotide was not determined (even at the highest concentration used, 0.5 µmol·l$^{-1}$, there was no inhibition observed), $K_i$ of the ssPSMA detection probe was 0.14 nmol·l$^{-1}$, $K_i$ of the dsbiotPSMA probe was 0.16 nmol·l$^{-1}$ and $K_i$ of the dsPSMA probe was 0.28 nmol·l$^{-1}$. From these data it is clear that the connection of single-stranded oligonucleotide tag not only doesn't worsen the inhibition constant, but actually it improved it by more than an order of magnitude. Furthermore, it was determined that addition of the second strand didn't influence the inhibitory constant and thereby the ability of the detection probe to bind to the active site of PSMA, which means that various modifications can be deliberately added to the original single-stranded detection probe ssPSMA by pairing with a modified complementary strand.

1d: Determination of Detection Probes Using qPCR

The designed sequence of single-stranded DNA contained in ssPSMA was optimized in the Vector NTI 10.3 (Invitrogen) so that it should not form strong secondary structure. At the margins were used sequences complementary to primers, for which it was previously verified that they allow the amplification of template DNA with high efficiency and that they don not form primer dimers at a given PCR conditions, thus ensuring the sensitivity of determination of the oligonucleotide tag in the ssPSMA probe in the order of single molecules. The sequence of primers used was CCA GCT TTT GTC TGG TGG AG (SEQ ID NO: 5) and CCT GCA GCC AGT TGA TTT TT (SEQ ID NO: 6) (Generi-Biotech; desalting 35 purification); and a hydrolysis probe #87 from Roche "Universal Probe Library" (LNA octamer sequence CTG CCA CC, cat. no. 04689127001) was chosen to detect amplified template DNA during qPCR.

To test the effectiveness of the determination, we prepared a decimal dilution series of the ssPSMA detection probe in double-distilled water in a concentration range of 10 nmol·l$^{-1}$ to 10 mol·l$^{-1}$, corresponding to a concentration of 6 to 6×10$^9$ copies per µl of solution. The dilution series was then used for qPCR calibration: 10 µl of a reaction mixture consisted of LC 480 Probes Master (Roche, cat. no. 04707494001; diluted to the final concentration recommended by the manufacturer), both primers (final conc. of each of them 1 nmol·l$^{-1}$), fluorescent hydrolysis probe #87 (final conc. 50 nmol·l$^{-1}$) and 1 µl of template DNA or 1 µl of distilled water in the no template control; each concentration and no template control was measured in triplicates. 96 well plates FrameStar 480/96 (4titude, cat. no. 4ti-0951) were used and after pipetting the reaction mixture into the wells they were sealed with adhesive optical films (Roche, cat. no. 4729692001). The time course of the PCR included successively 3 min at 95° C.; then 45 repetitions consisting of three steps: 10 s at 95° C., 30 sec at 66° C. and 30 sec at 72° C.; and finally 2 min at 37° C. We used the Light Cycler 480 II (Roche) with the excitation and emission filter adjusted to the FAM fluorophore. Threshold cycles ($C_q$) were obtained from the measured fluorescence curves using the method of maxima of the second derivative in the Light Cycler 480 II Software (Roche).

The obtained $C_q$ values plotted against the decimal logarithm of the concentration of template showed that the linear range of the assay was in the range of 6 to 6×10⁸ copies at over 90% efficiency of amplification, and 6 copies ($C_q$ 37 cycles) differed significantly from the no template control, which had no measurable signal. The data are listed in Table 1.

TABLE 1

$C_q$ values measured depending on the number of copies of the ssPSMA detection probe

| number of ssPSMA copies | $C_q$ |
|---|---|
| 6000000000 | 9.22 |
| 600000000 | 10.13 |
| 60000000 | 12.72 |
| 6000000 | 15.87 |
| 600000 | 19.10 |
| 60000 | 22.44 |
| 6000 | 26.17 |
| 600 | 29.96 |
| 60 | 33.47 |
| 6 | 37.39 |
| 0 | >45.00 |

1e: Determination of the Optimal Working Concentration and Optimal Diluent for the Detection Probe for Determining the Amount of PSMA In individual tests to determine the dissociation constant of the detection probe towards PSMA, 10 μl of a solution of various antibodies recognizing the native form of PSMA (2G7, J415, J591, D2B, 107-1A4; described in Tykvart et al. 2014, Prostate, p. 1674) at a concentration of 10 ng·μl⁻¹ in TBS buffer were loaded to the bottom of wells of a 96 well plate FrameStar 480/96 (4titude, cat. No. 4ti-0951) and incubated at room temperature for 30-120 minutes. The content of wells was then tapped out and the wells were washed three times with 200 μl of TBS. Then, 100 μl of casein blocking agent five times diluted in TBS (casein blocker biotin free 5.5% w/v"; SDT; cat. no. CBC1) was applied to the bottom of the wells and incubated for 1-15 hours at room temperature. Then content of the wells was tapped out again and the wells were washed three times with 200 μl of TBST (TBS with 0.05% (vol./vol.) Tween 20). Thereafter, either 10 μl of pure TBST' buffer (TBS with 0.1% (vol./vol.) Tween 20) or 10 μl of TBST' solution with purified recombinantly prepared extracellular portion of human PSMA (hereinafter rhPSMA) at a concentration of 1 μg·μl⁻¹ i.e. approximately 10 pmol·l⁻¹ was applied to the bottom of the wells. rhPSMA was prepared and purified as described in (Barinka et al., 2002, Journal of Neurochemistry, p. 477), purity was checked by SDS-PAGE and the concentration determined by amino acid analysis on Biochrom30 (Biochrom) according to the manufacturer's instructions; aliquots of protein stock solution were stored at −80° C. After 60 to 120 minutes incubation at room temperature, the content of the wells was tapped out and the wells were washed five times with 200 μl TBST. Finally, 10 μl of TBST' solution with the ssPSMA detection probe of several different concentrations in tenfold dilution series from 0.1 pmol·l⁻¹ to 10 nmol·l⁻¹ was added to the bottom of wells and incubated for 15-75 minutes at room temperature. Then content of the wells was tapped out again and the wells were washed ten times with 200 μl of TBST. Subsequently, 10 μl of a qPCR mixture of the same composition as in the case of no template control in the previous example 1d was added to the bottom of the wells and the amount of bound detection probe was than determined using qPCR as described in the example 1 d.

By the described procedure, the amount of the non-selectively adsorbed probe depending on its used concentration (dilution series of detection probe in wells with no added rhPSMA) was measured as well as the amount of the probe selectively bound to the active site of PSMA depending on its used concentration (dilution series of detection probe in wells with added rhPSMA). Dependence of selectively bound probe on its concentration was fitted by the function described by equation (3) using the "Solver" in Microsoft Office Excel 2003, where the variables solved were $E_{tot}$ (the maximum amount of selectively bound probe) and $K_d$ (dissociation constant of the probe), with minimizing the sum of squared relative deviations between the measured values and values calculated from the fitted function.

The whole assay was successively repeated with all the above mentioned antibodies and it was shown that the value of $K_d$ of the ssPSMA probe binding into the active site of the immobilized enzyme was always in the range of 100-200 pmol·l⁻¹, which corresponds very well to the inhibition constant of 140 pmol·l⁻¹, measured in the enzyme assay Immobilization of the enzyme on any of these antibodies therefore does not affect the binding affinity of the detection probe to the active site of the enzyme. The maximum amount of selectively bound probe for each antibody provided the $C_q$ read from qPCR of between 15 and 16; thus, there was not any significant difference among the antibodies in the efficiency of immobilization of the enzyme from the solution. The amount of non-selectively adsorbed detection probe was also similar for all antibodies and it was directly proportional to the concentration of the probe in the entire concentration range used. Subtracting the measured $C_q$ in the well without the enzyme (corresponding to a non-selective binding of the probe) from $C_q$ in a well with the enzyme (corresponding to selective binding of the probe) with the same antibody used and the same concentration of the probe, the signal/background ratio was determined. This was the highest for the probe concentration less than or equal to $K_d$ of its binding to the active site of PSMA and depending on the antibody ranged from 8 to 12 qPCR cycles, which corresponds to a hundred-fold to thousand-fold difference for the used amount of 10 pg rhPSMA.

The whole experiment was repeated with the 2G7 antibody wherein different concentrations of the ssPSMA detection probe were applied after dilution in TBST' or in TBST' with the addition of SDS in a concentration range of 0.005% to 0.02% (wt./vol.) or with the addition of a casein blocker diluted in the range of hundred to thousand fold, or in TBST' with both additives within the same concentration range. TBST' with 0.005% (wt./vol.) SDS and 500-fold diluted casein blocking agent (hereinafter "buffer CaSDS") was determined as the optimal; in which dissociation constant for the selective binding of the detection probe only slightly increased and selective binding thus remained almost unchanged and at the same time, non-selective adsorption was reduced, which showed as an increase of the measured $C_q$ by 5-6 cycles and thus increasing the signal/background ratio by a corresponding extent. Further experiments showed that the same effect is also achieved when using the other antibodies recognizing native form of PSMA.

Using the 2G7 antibody, the dissociation constant of not only the ssPSMA probe, but also dsPSMA, dsA3PSMA and dsbiotPSMA, was measured more accurately by the same procedure in further experiments. Unlike previous procedures, the applied concentration of rhPSMA was 0.1 pg·μl$^{-1}$ and each probe was applied usually in twelve different concentrations ranging from 3 to 1600 pmol·l$^{-1}$. For some probes, the determination of the dissociation constant was repeated several times, and the resulting $K_d$ values determined from individual measurements were almost identical to each other. It was found that $K_d$ of the ssPSMA, dsA3PSMA a dsbiotPSMA probes in TBST' is approximately 60 pmol·l$^{-1}$, whereas $K_d$ of the dsPSMA probe was about 100 pmol·l$^{-1}$. In the CaSDS buffer, the dissociation constant of all these probes was very similar, approximately 100 pmol·l$^{-1}$. Given that for each concentration of each probe, control wells without added antigen were also included, it was found that non-selective binding of single-stranded and double-stranded probes differ from each other. While the concentration of 1000 pmol·l$^{-1}$ of the ssPSMA probe in TBST' results in non-selective binding of the probe amount corresponding to $C_q$ equal to 24 and the same concentration of the same probe in CaSDS results in $C_q$ equal to 30, the concentration of 1000 pmol·l$^{-1}$ of the dsbiotPSMA probe (or other double-stranded probes) in TBST' results in non-selective binding of the probe amount corresponding to $C_q$ equal to 28 and the same concentration of the same probe in CaSDS results in k $C_q$ equal to 33. Dissociation constant for the ssPSMA probe and other forms of PSMA was determined in both buffers by the same procedure; this time, either lysate of human cell line expressing PSMA containing PSMA at a concentration of approximately 0.1 pg·μl$^{-1}$ (1 ng of total protein; the HEK line 1-750 is described in (Mlcochova et al. 2009, Prostate, p. 471), or tenfold diluted human citrate blood plasma containing endogenous PSMA at concentration of approximately 0.1 pg·μl$^{-1}$ was applied into the wells. The determined dissociation constant of the probe towards PSMA present in the cell lysate was approximately 140 pmol·l$^{-1}$ in TBST', while approximately 250 pmol·l$^{-1}$ in CaSDS; dissociation constant of the probe towards the endogenous PSMA contained in plasma was approximately 280 pmol·l$^{-1}$ in TBST', whereas 450 pmol·l$^{-1}$ in CaSDS. $C_q$ values obtained for the dilution series of the ssPSMA probe with various antigens are summarized in Table 2.

Dissociation constant of the ssPSMA probe towards purified recombinantly prepared biotinylated Avi-tagged proteins (Avi-PSMA and Avi-GCPIII) was determined in a similar manner. Purified Avi-GCPIII was prepared according to the procedure described in (Tykvart et al. 2014, Prostate, in press), the concentration of purified protein was determined by amino acid analysis on Biochrom30 (Biochrom) according to the manufacturer's instructions, aliquots of protein stock solution were stored at −80° C. GCPIII is a close human homologue of PSMA having very similar enzyme activity and is therefore another suitable target for quantification. The procedure was identical to the procedure described at the beginning of this paragraph; only in the first step, a solution of neutravidin (Pierce, cat. no. 31000) in TBS at concentration of 10 ng·μl$^{-1}$ was applied to the wells instead of the antibody. Following steps were the same, only instead of rhPSMA, aforementioned Avi-PSMA diluted in TBST' to a concentration of 0.24 pg·μl$^{-1}$ or Avi-GCPIII diluted in TBST' to a concentration of 100 pg·μl$^{-1}$ were applied. The determined dissociation constant of the ssPSMA probe was 160 pmol·l$^{-1}$ towards Avi-PSMA (140 pmol·l$^{-1}$ by enzyme kinetics) and 1700 pmol·l$^{-1}$ towards Avi-GCPIII, meaning that the probe effectively binds also into the active site of Avi-GCPIII.

1f: Determination of Concentrations of PSMA and its GCPIII Homologue in a Solution In individual tests to determine PSMA concentrations, either 10 μl of the 2G7 antibody solution or 10 μl of neutravidin solution, both at the concentration of 10 ng·μl$^{-1}$ in TBS, were applied to the bottom of wells in a 96-well plate FrameStar 480/96 and incubated at room temperature for 30 to 120 minutes. Content of the wells was then tapped out and the wells were washed three times with 200 μl of TBS. 100 μl of casein blocking agent five times diluted in TBS was then applied to the bottom of the wells and incubated 1-15 hours at room temperature. Content of the wells was tapped out again and the wells were washed three times with 200 μl of TBST. 10 μl of TBST' solution with variously concentrated proteins to be determined was then added to the bottom of the wells. After 60 to 120 minutes of incubation at room temperature, the content of the wells was tapped out and the wells were washed five times with 200 μl of TBST. Finally, 10 μl of TBST' solution of the detection probe was added to the bottom of wells and incubated for 15-75 minutes at room temperature. Content of the wells was tapped out and the wells were washed ten times with 200 μl of TBST. 10 μl of a qPCR mixture of the same composition as in the case of no template control in Example 1d was then added to the bottom of the wells and subse-

TABLE 2

$C_q$ values obtained for the dilution series of the ssPSMA probe with various antigens

| concentration of ssPSMA, pmol · l$^{-1}$ | TBST' buffer | | | CaSDS buffer | | |
|---|---|---|---|---|---|---|
| | 2 pg rhPSMA | 1 ng HEK1-750 | 1 μl plasma | 2 pg rhPSMA | 1 ng HEK1-750 | 1 μl plasma |
| 1600 | 15.86 | 16.36 | 16.96 | 15.81 | 16.43 | 17.03 |
| 800 | 15.95 | 16.48 | 17.19 | 15.85 | 16.64 | 17.39 |
| 400 | 16.04 | 16.66 | 16.86 | 16.29 | 17.02 | 17.98 |
| 200 | 16.26 | 17.07 | 18.01 | 16.47 | 17.63 | 18.57 |
| 150 | 16.49 | 17.30 | 18.03 | 16.84 | 17.72 | 18.95 |
| 100 | 16.60 | 17.63 | 18.66 | 17.04 | 18.39 | 19.60 |
| 75 | 16.85 | 18.22 | 19.22 | 18.19 | 18.70 | 19.93 |
| 50 | 16.85 | 18.46 | 19.63 | 17.59 | 18.98 | 20.29 |
| 25 | 17.67 | 19.13 | 20.50 | 18.15 | 19.91 | 21.13 |
| 12.5 | 18.67 | 19.98 | 21.21 | 19.17 | 20.78 | 22.06 |
| 6.25 | 19.40 | 20.96 | 22.28 | 20.16 | 21.85 | 22.99 |
| 3.125 | 20.35 | 22.02 | 23.55 | 21.14 | 22.79 | 24.24 | quently the amount of bound detection probe was determined by qPCR the same way as described in Example 1d.

In the first embodiment, the 2G7 antibody was applied to the wells, and after blocking the surface, 10 μl of rhPSMA solution in a concentration range of 1 ng·μl$^{-1}$ to 0.1 fg·μl$^{-1}$ (prepared by a dilution series of the purified rhPSMA of known concentration in TBST' buffer) was added. For the detection, 100 pmol·l$^{-1}$ solution of ssPSMA in CaSDS, 1000 pmol·l$^{-1}$ solution of dsbiotPSMA in CaSDS and 60 pmol·l$^{-1}$ solution of Neu_dsbiotPSMA in CaSDS were successively tested. The Neu_dsbiotPSMA detection probe was prepared by mixing 3 μl of a neutravidin solution at a concentration of 1 mg·ml$^{-1}$ with 20 μl of a solution of biotinylated dsbiotPSMA detection probe at a concentration of 10 μmol·l$^{-1}$ (corresponding to a fourfold molar excess compared to neutravidin) in TBS buffer. After overnight incubation on ice, the resulting complex was purified from any excess free dsbiotPSMA probe by ultrafiltration on Amicon Ultra 0.5 ml 100K; the retentate volume was diluted tenfold in TBS, twice consecutively. The final concentration of the detection probe in the complex was determined by qPCR by comparison with a standard dilution series of ssPSMA as described in Example 1d.

Figure 8:
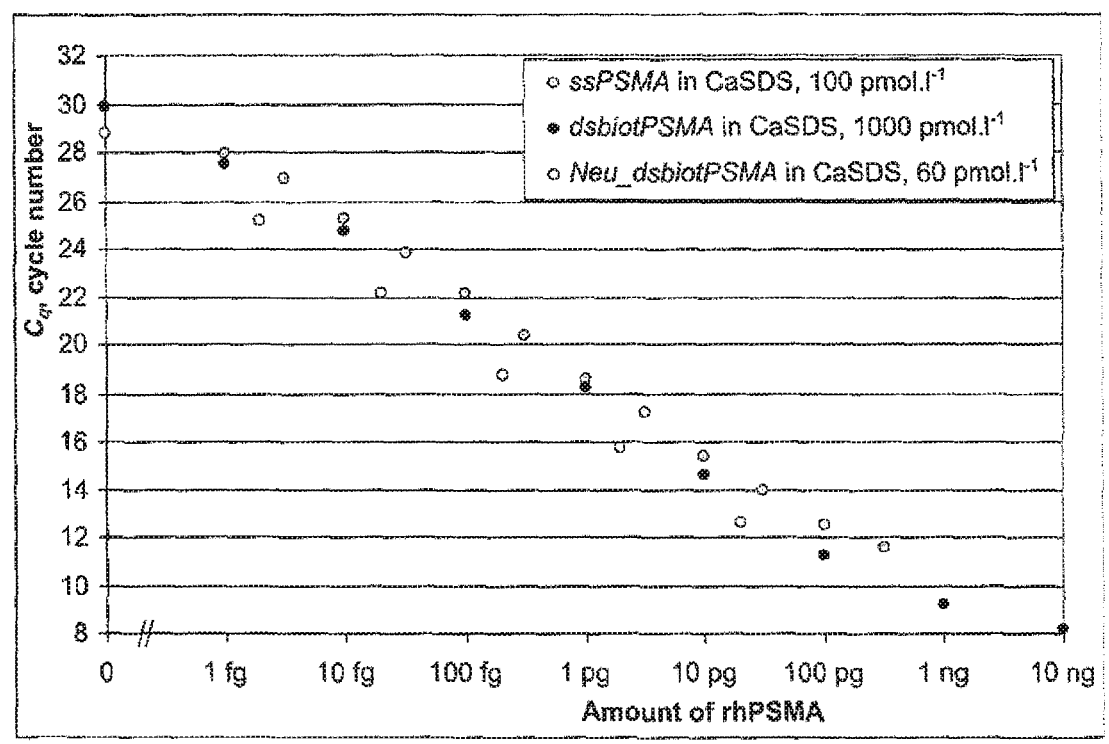
FIG. 8 shows the dependence of the measured $C_q$ values (y-axis) on the amount of PSMA protein in the wells (x-axis) for various concentrations of various detection probes.

It was found that using the solution of dsbiotPSMA detection probe in CaSDS at a concentration of 1000 pmol·l$^{-1}$, concentration of rhPSMA can be determined throughout the test range, i.e. from 10 ng to 1 fg with linear range of the determination being approximately six orders of magnitude (from 1 ng to 1 fg; the value of $R^2$ of reliability of logarithmic fitting of the results from 7 concentrations in this range was 1.00, as calculated in Microsoft Office Excel 2003, see FIG. 8). Logarithmic fit was used because the linear correlation is valid for $C_q$ dependence on the logarithm of analyte concentration. Using the ssPSMA detection probe at concentration of 100 pmol·l$^{-1}$ in CaSDS, the linear range was approximately in the range of hundreds pg to units of fg of rhPSMA ($R^2$ value of the logarithmic fit of the results from 12 concentrations ranging from 316 pg to 1 fg was 0.99; see FIG. 8). It was also found that using the complex detection probe Neu_dsbiotPSMA retains all the preferable features of the original probe concerning sensitivity and dynamic range, i.e. the detection limit significantly below 1 fg rhPSMA and linear range of rhPSMA determination of at least five orders of magnitude ($R^2$ of logarithmic fit of the results of five concentrations in the range of 20 pg to 2 fg was 1.00; see FIG. 8). The $R^2$ values demonstrate excellent accuracy of the determination of the concentration, because such values were achieved from a single well for each concentration only, i.e. without replicates. Similar results were obtained when detection probes were diluted in TBST' buffer, only the dynamic range was approximately an order of magnitude narrower due to higher non-specific adsorption of the detection probes in this buffer and the resulting lower sensitivity. Measured $C_q$ values using single- and double-stranded probes (ssPSMA and dsbiotPSMA) depending on the amount of rhPSMA are summarized in Table 3.

TABLE 3

$C_q$ Values measured with single- and double-stranded probes (ssPSMA and dsbiotPSMA) depending on the amount of rhPSMA

| amount of rhPSMA, pg | ssPSMA in CaSDS, 100 pmol · l$^{-1}$ | dsbiotPSMA in CaSDS, 1000 pmol · l$^{-1}$ |
|---|---|---|
| 10000 | N/A | 8.20 |
| 1000 | N/A | 9.22 |
| 316 | 11.55 | N/A |
| 100 | 12.47 | 11.23 |
| 32 | 13.97 | N/A |

TABLE 3-continued $C_q$ Values measured with single- and double-stranded probes (ssPSMA and dsbiotPSMA) depending on the amount of rhPSMA

| amount of rhPSMA, pg | ssPSMA in CaSDS, 100 pmol · l$^{-1}$ | dsbiotPSMA in CaSDS, 1000 pmol · l$^{-1}$ |
|---|---|---|
| 10 | 15.40 | 14.66 |
| 3.2 | 17.15 | N/A |
| 1.0 | 18.58 | 18.18 |
| 0.32 | 20.34 | N/A |
| 0.10 | 22.14 | 21.21 |
| 0.032 | 23.87 | N/A |
| 0.010 | 25.26 | 24.78 |
| 0.0032 | 26.92 | N/A |
| 0.0010 | 27.88 | 27.47 |
| 0 | 29.91 | 29.84 |

As demonstrated in the previous example 1e, the detection probe for PSMA binds also into the active site of its close homologue GCPIII. Selectivity of the determination was therefore tested by the same procedure as above; besides the 10 μl of rhPSMA solution, 10 μl of a solution of purified tagged and biotinylated Avi-GCPIII, or 10 μl of solution of purified extracellular portion of the human GCPIII prepared by recombinant expression (hereinafter rhGCPIII, prepared according to the procedure in (Hlouchová et al. 2007, Journal of Neurochemistry, p. 682)), were applied to the other wells, both at various concentrations ranging from 1 ng·μl$^{-1}$ to 0.1 fg·μl$^{-1}$. A solution of ssPSMA probe in CaSDS at a concentration of 1000 pmol·l$^{-1}$ was used for the detection. While rhPSMA was detectable even at the lowest application quantity of 1 fg, with all applied quantities of Avi-GCPIII or rhGCPIII except the two highest (1 and 10 ng), there was no detectable difference from the wells without any analyte. The amount of bound detection probe in the wells with 10 ng of said proteins approximately corresponded to the amount of bound probe in the well with 10 fg of PSMA; that means that the determination of PSMA would lead to false positive results only in case that the concentration of GCPIII in the analysed sample would be at least about six orders of magnitude higher than the concentration of PSMA. Moreover, further order increase in the selectivity can be achieved with a tenfold reduction in the concentration of detection probe down to the $K_d$ of the probe towards PSMA, as the $K_d$ of the probe towards GCPIII is nearly twenty times higher. This example shows that in combination with a selective antibody, extraordinary high selectivity can be achieved even with a probe binding to more analytes.

In another embodiment, neutravidin solution was applied into the wells in the first step and after blocking the surface, 10 μl solution of purified tagged and biotinylated Avi-PSMA, or purified tagged and biotinylated Avi-GCPIII diluted in TBST' was applied into the wells in various concentrations. The ssPSMA probe solution at a concentration of 1000 pmol·l$^{-1}$ in CaSDS was used for detection of Avi-PSMA, and at a concentration of 10000 pmol·l$^{-1}$ in CaSDS for detection of Avi-GCPIII. Linear range of Avi-PSMA determination was in the range of 10 ng to 100 fg, while linear range of Avi-GCPIII determination was in the range of 10 ng to 10 pg. Measured values of $C_q$ depending on the amount of Avi-PSMA or Avi-GCPIII are summarized in Table 4.

TABLE 4

Measured values of $C_q$ depending on the amount of Avi-PSMA or Avi-GCPIII:

| Quantity, pg | Avi-PSMA | Avi-GCPIII |
|---|---|---|
| 10000 | 9.65 | 11.71 |
| 1000 | 13.02 | 15.37 |
| 100 | 16.72 | 19.11 |
| 10 | 19.88 | 21.77 |
| 1 | 23.26 | 23.59 |
| 0.1 | 26.20 | 23.95 |
| 0.01 | 25.81 | 23.98 |
| 0.001 | 28.04 | 24.00 |
| 0 | 27.24 | 22.13 |

Controls confirming the selectivity of the analyte determination were included in all assays; in the control wells, no antibody or no neutravidin for the selective immobilization of the test protein were applied to the wells and the surface was only blocked, in which cases the amount of bound probe corresponding to wells without the analyte was observed. Alternatively, detection probe was added to the wells in a solution containing a known competitive inhibitor of PSMA or GCPIII at concentrations significantly higher than their inhibition constants, leading to a strong decline in bound probe compared to wells without the inhibitor.

In another embodiment, elution of probe selectively bound to the active site of PSMA was tested; procedure was the same as described at the beginning of the example. 2G7 antibody was first immobilized on the surface of the wells, and after blocking the surface, besides TBST' buffer alone, decimal dilution series of rhPSMA in TBST' from 2 pg to 2 fg of rhPSMA was applied to the wells. Solution of ssPSMA in CaSDS at a concentration of 100 pmol·l$^{-1}$ was added to the wells for the detection. Finally, after washing the unbound probe away, 10 μl of TBST' buffer was added in some wells. After 1 hour at room temperature, the solution was collected from these wells (hereinafter "elution") and wells were washed again ten times with 200 μl of TBST. Only then, 10 μl of a qPCR mixture of the same composition as in the case of no template control in Example 1d were added to the wells, and subsequently the amount of bound probe was determined by qPCR by the same procedure as described in Example 1d. In addition, the amount of probe in 1 μl of collected elution was determined in the same manner (10 μl of the qPCR mixture of the same composition as above was applied to a clean well, 1 μl of the elution was added and the amount of detection probe was determined by qPCR as above). Comparing the amount of bound detection probe in the wells eluted with TBST' and in the non-eluted wells showed that approximately 50% of the detection probe was released from the surface within one hour, which was in accordance with the measured concentration of the probe in the elution. $C_q$ measured depending on the PSMA concentration and the determination process are summarized in Table 5.

TABLE 5

$C_q$ measured depending on the PSMA concentration and the determination process

| Quantity of rhPSMA, fg | non-eluted | eluted | elution |
|---|---|---|---|
| 2000 | 18.88 | 19.60 | 23.88 |
| 200 | 22.35 | 23.50 | 27.45 |
| 20 | 25.73 | 26.68 | 30.61 |
| 2 | 28.85 | 29.76 | 32.85 |
| 0 | 29.96 | 31.91 | 34.79 |

It is clear that the linear range and detection limit are the same when determining the eluted probe as when determining the probe bound to a solid carrier. This procedure can thus be used to release the bound probe to a solution allowing determination in other types of solid carriers than the one to which the immobilization was done.

1g: Determination of the Limit of Detection of PSMA in a Solution

Figure 9:
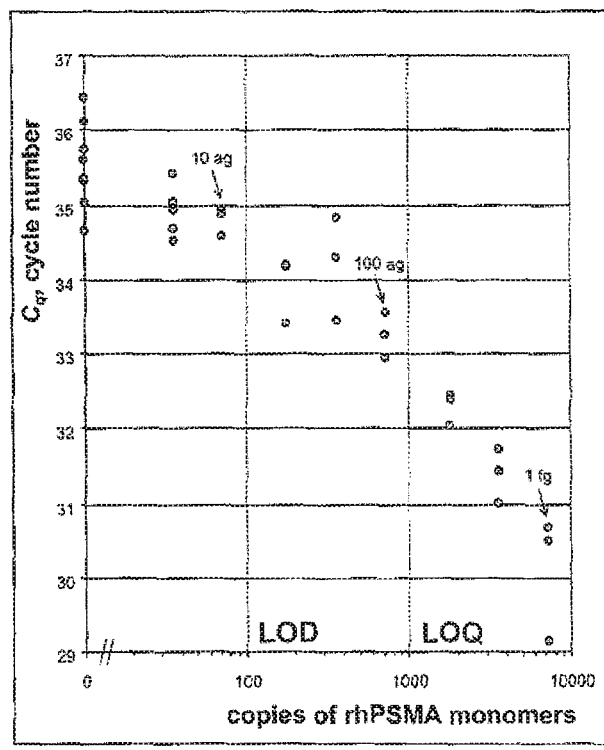
FIG. 9 shows the dependence of the measured $C_q$ values (y-axis) on the number of PSMA molecules (x-axis). Limit of detection (LOD) and limit of quantification (LOQ) are shown by dashed vertical lines.

10 μl of 2G7 antibody solution at a concentration of 2.5 ng·μl$^{-1}$ in TBSE buffer (TBS with EDTA at a concentration of 5 mmol·l$^{-1}$) was applied to the bottom of the wells of a 96-well plate FrameStar 480/96 and incubated at room temperature for 6 hours. Content of the wells was then tapped out and the wells were washed three times with 200 μl of TBS. 200 μl of casein blocking agent five times diluted in TBSE was then applied to the bottom of the wells and incubated for 18 hours at room temperature. Content of the wells was tapped out and the wells were washed five times with 200 μl of TBST. Thereafter, either 10 μl of TBST' buffer or 10 μl of rhPSMA solution in TBST' of known concentration of rhPSMA in the range of 0.1 fg·μl$^{-1}$ to 0.5 ag·μl$^{-1}$, i.e. in a total amount of rhPSMA between 1 fg to 5 ag, were applied to the bottom of wells wherein each concentration was applied at least in triplicate. After 3 hours incubation at room temperature the content of the wells was tapped out and the wells were washed three times with 200 μl TBST. Finally, 10 μl of solution of detection probe dsA3PSMA(1:1.2) in CaSDS buffer at the probe concentration of 75 pmol·l$^{-1}$ was applied to the bottom of wells and incubated for 1 hour at room temperature. The dsA3PSMA(1:1.2) probe was prepared by the same procedure as the dsA3PSMA probe with the difference that the ssPSMA probe was paired with a 1.2 molar excess of the complementary strand, at a concentration of ssPSMA 1 nmol·l$^{-1}$. Contents of the wells was subsequently tapped out and the wells were washed ten times with 200 μl TBST. 10 μl of a qPCR mixture of the same composition as in the case of no template control in Example 1d was then applied to the bottom of the well and the quantity of bound detection probe was subsequently determined by qPCR in the same way as described in Example 1d. Measured $C_q$ values depending on the amount of applied rhPSMA are summarized in Table 6 and FIG. 9. It is evident that the linear range of rhPSMA quantification extends down to 0.1 fg (which at the molecular weight of the rhPSMA monomer determined by MALDI-TOF as 88.7 kDa corresponds to approximately 680 molecules rhPSMA i.e. to 340 dimers). The limit of detection was at least between 10 and 25 ag, i.e. between 34 and 85 dimers, because the difference between the average $C_q$ of wells without rhPSMA and with 25 ag rhPSMA was more than one cycle.

TABLE 6

Measured $C_q$ values depending on the amount of applied rhPSMA

| quantity of rhPSMA, fg | $C_q$ (1) | $C_q$ (2) | $C_q$ (3) |
|---|---|---|---|
| 0 | 35.74 | 36.44 | 35.60 |
| 0 | 36.10 | 35.32 | 34.65 |
| 0 | 34.64 | 35.03 | 35.36 |
| 0.005 | 34.52 | 34.68 | 35.01 |
| 0.005 | 35.41 | 34.92 | 35.06 |
| 0.010 | 34.93 | 34.86 | 34.58 |
| 0.025 | 34.17 | 34.19 | 33.41 |
| 0.050 | 33.45 | 34.30 | 34.83 |
| 0.10 | 33.55 | 33.25 | 32.94 |
| 0.25 | 32.44 | 32.02 | 32.38 |
| 0.50 | 31.72 | 31.44 | 31.01 |
| 1.00 | 30.51 | 30.68 | 29.15 |

Each tested sample was measured in triplicate, 5 ag sample in six copies and zero sample in nine copies, so these samples have more rows in the table.

1h: Determination of PSMA Concentration in Complex Biological Matrices

10 µl of 2G7 antibody solution at 5 ng·µl$^{-1}$ in TBS was loaded to the bottom of the wells of a 96-well plate Frame-Star 480/96 and incubated at room temperature for 1 to 1.5 hours. Content of the wells was then tapped out and the wells were washed three times with 200 µl of TBS. then 100 µl of casein blocking agent five times diluted in TBS was applied to the bottom of the wells and incubated for 24 hours at room temperature. Content of the wells was tapped out and the wells were washed three times with 200 µl TBST. Thereafter, either 10 µl of rhPSMA standard solution at 12 different concentrations in TBST' (range 32 pg·µl$^{-1}$ to 0.1 fg·µl$^{-1}$), or analysed samples of cell lysate, urine and blood plasma in various dilutions in TBST' buffer, were added to the bottom of the wells. After 1.5 hours incubation at determining PSMA in urine and cell lysate or after 18 hours incubation at the determining PSMA in blood plasma, always at room temperature, the content of the wells was tapped out and the wells were washed five times with 200 µl TBST. Finally, 10 µl solution of ssPSMA detection probe in CaSDS buffer at the probe concentration of 1000 pmol·l$^{-1}$ was added to the bottom of wells and incubated for 1 hour at room temperature. Content of the wells was subsequently tapped out and the wells were washed ten times with 200 µl of TBST. 10 µl of a qPCR mixture of the same composition as in the case of no template control in Example 1d was then added to the bottom of the wells and subsequently the amount of bound detection probe was determined using qPCR as described in Example 1d.

Figure 10:
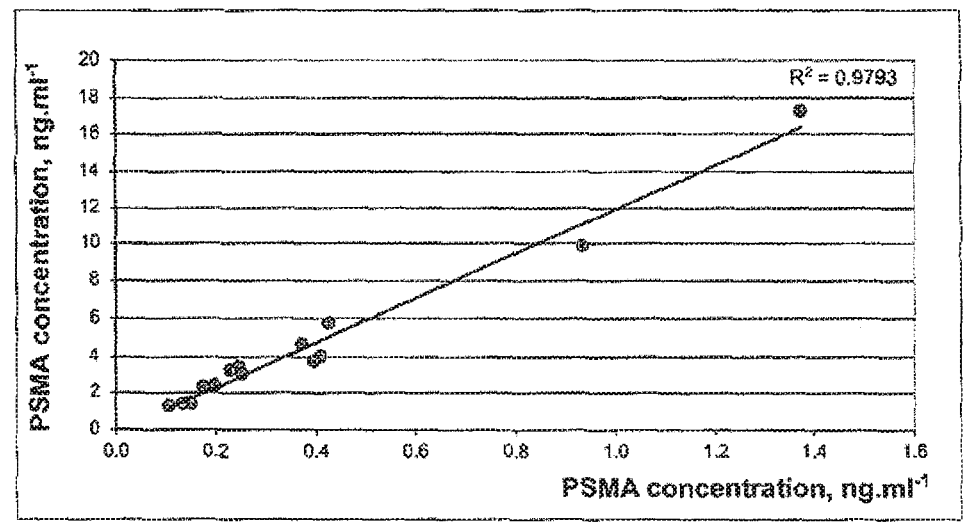
FIG. 10 shows the correlation of PSMA concentrations in samples of human citrated plasma from a total of 15 healthy donors measured by the method disclosed herein (x-axis) and radio-enzymatic assay (y-axis).

The linear range of the detection was according to the standard dilution series of the rhPSMA the same as in the previous example. The concentration of PSMA in the biological samples was then calculated from the obtained calibration curves (dependence of $C_q$ on the logarithm of rhPSMA concentration fitted with linear function) and from knowledge of dilution of the analysed biological samples. First, the PSMA concentrations in 15 samples of citrate plasma of healthy donors was determined; wherein the final value was the average of concentrations determined in a ten-, hundred- a thousand-fold diluted plasma samples of individual donors. PSMA concentrations determined from various dilutions were identical to each other (except for minor variations); moreover, the determined amount of PSMA were always well above the limit of detection ($C_q$ difference of at least three cycles compared to null controls), even for the most diluted samples with the lowest concentrations of PSMA. This means that plasma volume of no more than 10 nl is sufficient for the described determination of PSMA. Furthermore, the selectivity of binding of the detection probe via its ligand portion was verified both by a suppressed binding to the surface of the wells with analysed samples when a competitive inhibitor of PSMA was added to the applied probe solution; and further by the fact that binding of oligonucleotide iqPCR_amino without the ligand portion to the surface of the wells with analysed samples did not exceed non-selective binding to the surface without a sample. The measured concentrations were then compared with the concentrations measured in the same samples using radio-enzymatic assay (procedure of collecting and processing citrate plasmas and determination of the PSMA concentration in these samples by means of a radio-enzymatic assay are described in (Knedlík et al. 2014, Prostate, p. 768). Although the absolute values determined by the method disclosed herein were approximately ten times smaller compared to the radio-enzymatic determination (Table 7), values from the two methods are very well correlated. This can be seen from the graphical plot comparing the results of both methods in FIG. 10 and from the value of reliability $R^2$ of direct correlation between the results of both methods, which was equal to 0.98. The difference in the measured absolute concentrations of PSMA can be caused by the imprecise radio-enzymatic determination due to differences in the rate of substrate cleavage between rhPSMA, which was used as a standard, and the endogenous PSMA to be determined in plasma. The rate of substrate cleavage by endogenous PSMA under given conditions of radio-enzymatic assay has not been determined; it was assumed to be the same as for rhPMSA. In contrast, when determining by the method disclosed herein, the affinity of the probe both towards the rhPSMA standard and towards endogenous PSMA was measured and such probe concentrations were used (well above the $K_d$ of the probe towards both proteins) as to avoid distortion of the results due to differences in bond strength of the probe to the individual proteins.

TABLE 7

Comparison of PSMA concentration measured by a reference method and by our method

| | concentrations of PSMA (ng · ml$^{-1}$) measured by: | |
|---|---|---|
| | a method according to the invention | radio-enzymatically |
| sample 1 | 0.43 | 5.7 |
| sample 2 | 0.40 | 3.7 |
| sample 3 | 0.14 | 1.4 |
| sample 4 | 0.11 | 1.3 |
| sample 5 | 0.26 | 3.0 |
| sample 6 | 0.23 | 3.2 |
| sample 7 | 0.94 | 9.9 |
| sample 8 | 0.37 | 4.6 |
| sample 9 | 0.41 | 4.0 |
| sample 10 | 1.37 | 17 |
| sample 11 | 0.25 | 3.4 |
| sample 12 | 0.15 | 1.4 |
| sample 13 | 0.18 | 2.3 |
| sample 14 | 0.15 | 1.5 |
| sample 15 | 0.20 | 2.4 |

The concentration of PSMA in urine samples ten- and a hundred-fold diluted in TBST' was also determined with the described method; variation between measured concentrations were very small, typically ten percent. In two samples of urine from patients suffering from prostate cancer, the measured concentrations of PSMA were 33 and 192 pg·ml$^{-1}$; in urine of a healthy male, the concentration was 15 pg·ml$^{-1}$, while in the urine of healthy female, it was just 8 pg·ml$^{-1}$. Although 1 µl of urine was sufficient for the determination of PSMA with our method, there is currently no available reference method sensitive enough, with which the measured concentrations could be compared. However, as well as in the blood plasma, binding of the detection probe was suppressed by addition a competitive inhibitor of PSMA, which demonstrates selective binding of the detection probe to the active site of PSMA via its ligand portion.

Described method was also used to determine concentrations in lysates of cultures of cell lines derived from prostate cancer, particularly from metastatic cells LNCaP, DU-145 and PC-3. Cells grown at 37° C. in an atmosphere of 5% (vol./vol.) $CO_2$ in RPMI medium (Sigma, cell line LNCaP) or IMDM medium (Invitrogen) supplemented with 10% (vol./vol.) FBS (Sigma) in Petri dishes of 100 mm diameter, designed for tissue cultures (SPL Life Sciences) were after reaching approximately 90% confluence resuspended in this medium, transferred to a microtube and centrifuged for 5 min at 250 g at room temperature. The medium was then removed and the cells were washed with 50 mmol·l$^{-1}$ Tris with 100 mmol·l$^{-1}$ NaCl at pH 7.4 (hereinafter referred to as CLP). Approximately 20 million cells were then suspended in 300 µl of CLP and transferred into 2 ml microtube with round bottom; and a steel ball with a diameter of approximately 3 mm was added to them. Cells were subsequently lysed and homogenized in a Tissue Lyzer (Qiagen; three minutes at maximum power). Solution was then transferred to a new tube, ⅒ volume of 10% (wt./vol.) octaethylengly-colmonododecyl ether (Affymetrix, cat. No. 0330; $C_{12}E_8$) was added and after mixing, the solution was sonicated for 1 min in ice-cold sonication bath Elmasonic S30. The resulting solution was centrifuged for 15 min/600 g/4° C. and supernatant was collected, which represents the lysate. The total protein concentration in the lysate was determined using the Biorad Protein Assay reagent. PSMA concentration was determined at various lysate dilutions in TBST'; applied amount of total protein ranged from 100 ng to 100 pg. Measured concentration of PSMA in LNCaP line was 0.27 ng/µg total protein, whereas in lines DU-145 and PC-3, PSMA was not detectable, which represented a concentration of less than 0.1 pg/ng of total protein under the given conditions of determination. Binding of the detection probe was also suppressed by adding a competitive inhibitor of PSMA to the solution of the detection probe, and the measured concentrations were also in accordance with the determination by Western blotting.

1i: Testing the Inhibitory Potency of Compounds Towards Various Forms of PSMA and Towards its Homologue GCPIII 10 µl of a neutravidin solution at 10 ng·µl$^{-1}$ in TBS buffer was applied to the bottom of the wells of a 96-well plate FrameStar 480/96 and incubated at room temperature for 1.5 hours. Contents of the wells was then tapped out and the wells were washed three times with 200 µl of TBS. 200 µl of casein blocking agent five times diluted in TBS was then applied to the bottom of the wells and incubated for 24 hours at room temperature. Content of the wells was tapped out and the wells were washed three times with 200 µl TBST. Thereafter, 10 µl of the standard solutions with known concentrations of Avi-PSMA (50 pg·µl$^{-1}$) or Avi GCPPIII (2 ng·µl$^{-1}$) in TBST' were added to the bottom of wells; zero controls with buffer alone were also included. After 2 hours incubation at room temperature the contents of the wells was tapped out and the wells were washed five times with 200 µl TBST. Then, 10 µl of ssPSMA detection probe solution in TBST' buffer was applied to the bottom of the wells, at the concentration of the probe 200 pmol·l$^{-1}$ for Avi-PSMA wells, or the concentration of 1000 pmol·l$^{-1}$ to the Avi-GCPIII wells. Subsequent incubation was carried out for 1 hour at room temperature. Contents of the wells was subsequently tapped out and the wells were washed ten times with 200 µl of TBST. 10 µl of a qPCR mixture of the same composition as in the case of no template control in Example 1d was then added to bottom of the wells and the quantity of bound detection probe was determined by qPCR as described in Example 1d.

Adding a certain concentration of a tested substance to the detection probe allowed deriving the inhibition constant of the substance from the decrease in bound detection probe amount. The tested substance was always added in one concentration only, and the assay was performed in duplicate. 15 substances have been selected for testing; their inhibitory constant towards Avi-PSMA was also measured by enzymatic assay described in Example 1c. Their inhibition constants were in the range of tens pmol·l$^{-1}$ to hundreds µmol·l$^{-1}$. Subtracting $C_q$ measured in the wells with enzyme and pure detection probe from $C_q$ measured in the wells with the same enzyme and the detection probe, accompanied by the tested substance, ΔCq was calculated from which the percentage of the active sites of enzyme occupied with the tested substance was derived, using the formulas (9) and (14); qPCR efficiency has been replaced by the value of one. ΔCq obtained by subtracting $C_q$ measured in the wells with enzyme from $C_q$ measured in zero controls (wells without enzyme) was used to determine the maximum extent of determining the percentage quantity of occupied active sites of the enzyme.

Figure 11:
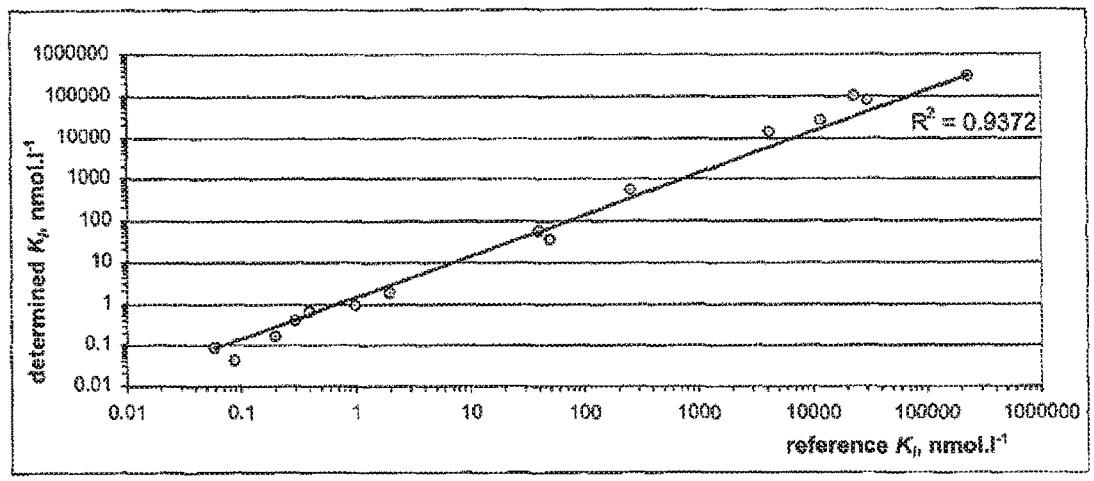
FIG. 11 shows a correlation of the inhibition constants $K_i$ of various substances towards Avi-PSMA measured with the method disclosed herein (y-axis) and the reference enzyme kinetics (x-axis). For better clarity, both graph axes are shown in a logarithmic scale.

By substituting the concentration of tested substance, $\Delta C_q$, $K_d$ of the detection probe identified in Example 1e (160 pmol·l$^{-1}$ for ssPSMA and Avi-PSMA in TBST'; 1700 pmol·l$^{-1}$ for ssPSMA and Avi-GCPIII in TBST') and the concentration of the detection probe into the equation (15), the value of the inhibition constant of the substance was determined. Table 8 summarizes the concentrations of the tested substances used in the determination, the percentage of active sites of the enzyme occupied by them, measured inhibition constants towards the given enzyme and reference values of inhibition constants measured with enzyme kinetics described in Example 1c. Reference values for the Avi-GCPIII enzyme are not known because greater amount of the enzyme would be necessary for measuring $K_i$ of several substances, than was available. The table shows that for Avi-PSMA, deviation between the two methods is at most tens of percent for the highly-binding inhibitors; and for the six weakest-binding inhibitors, the constants determined by the method disclosed herein are two to four times higher. Excellent agreement between the two methods is evident from a graphical comparison of the results of both methods shown in FIG. 11; the reliability value $R^2$ of the linear correlation between $K_i$ determined by our method and $K_i$ determined by reference enzyme kinetics was 0.94 for Avi-PSMA.

Minor differences between the two methods can be due to inaccuracy in our determination or inaccuracies in the determination of enzyme kinetics. Our determination could be refined by measuring multiple replicates, either with the same or different concentrations of the tested substances, and averaging the resulting values. Errors in the determination by enzyme kinetics arise mainly from inaccurate determination of substrate $K_M$ (systematic shift in all $K_i$) and incorrect fitting of the reaction rate dependence on the inhibitor concentration. At this point it should be stressed that even a properly measured $K_i$ value cannot be considered as a proper physical constant, since the properties of enzymes, in our context particularly the affinity of the enzyme to the substrate and the rate of the enzyme catalysed reaction, is fundamentally dependent on the composition of the solution. Measured $K_i$ thus generally strongly depends on the particular pH, temperature, buffer substance used, the ionic strength of the solution, the nature of the ions in the solution, various additives (e.g. detergents), and other influences. Even if $K_i$ is determined by enzyme kinetics at very similar conditions, results are quite often different, for example as seen in the $K_i$ determination of a known inhibitor of 2-PMPA. In the work described in (Jackson et al. 1996, Journal of Medicinal Chemistry, p. 619) $K_i$ of 2-PMPA was determined as 0.3 nmol·l$^{-1}$, whereas in (Kozikowski et al. 2004, Journal of Medicinal Chemistry, p. 1729) it was determined as 1.4 nmol·l$^{-1}$. In our assay, another buffering agent and another detergent were used compared to the enzyme kinetics, and they were also in higher concentrations, which might contribute to the observed small differences in the results.

In a similar manner, with very similar results, inhibitory potency of substances was tested for unpurified recombinant PSMA with N-terminally attached His-tag. The procedure was identical to the procedure described above for Avi-PSMA, but after the immobilization of neutravidin, there was one additional step of one hour incubation of the wells with 10 μl tris-nitrilotriacetic acid with covalently attached biotin (biotin-tris-NTA) at a concentration of 10 nmol·l$^{-1}$ in the presence of NiCl$_2$ at a concentration of 1 mmol·l$^{-1}$ in TBST' buffer, and only after washing, the step of incubation with His-tagged PSMA followed.

the inhibitory potency of tested substance 4 towards Avi-GCPIII was verified by enzyme kinetics (measured $K_i$=140 nmol·l$^{-1}$).

The fact that the tested substances are usually dissolved in various organic solvents, has led to testing the reliability of our method in the presence of acetonitrile, methanol, dimethyl sulfoxide (DMSO) and the detergent Tween 20. The procedure was identical to those described above, only at the beginning, instead of the solution of neutravidin, 2G7 antibody solution at a concentration of 5 ng·μl$^{-1}$ in TBS was applied to the wells. Instead Avi-tagged proteins, rhPSMA solution of known concentration 2 pg·μl$^{-1}$ in TBST' was then applied. The ssPSMA probe solution at a concentration of 60 pmol·l$^{-1}$ in TBST', or in TBST' with variously concentrated organic solvent, or in TBS with varying concentrations of Tween 20 was used for the detection. Zero controls without antigen were included for each detection probe solution used, and everything was measured in duplicates. Possible influence of the composition of probe diluent on the assay was determined by comparing the measured $C_q$ in wells with and without antigen. It was found that DMSO, acetonitrile or methanol did not influence the measured results at concentrations of 0.1%, 1% or 10% (vol./vol.). Similarly, various concentrations of Tween 20 in the range of 0% to 1% (vol./vol.) in the diluent had no effect on the determination. At said concentrations of DMSO, Tween 20, optionally with addition of 500-fold to 2000-fold diluted casein blocker, a set of inhibitors with respective $K_i$ values ranging from 100 pmol·l$^{-1}$ to 100 nmol·l$^{-1}$ was tested and it was found, that the additives had no effect on accuracy of the determination of respective $K_i$ values. Addition of three inhibiting substances in various concentrations was also tested; with inhibition constants of hundreds pmol·l$^{-1}$, tens nmol·l$^{-1}$ and tens nmol·l$^{-1}$, and it was found that within the linear range of the

TABLE 8

Comparison of $K_i$ values and the percentage of occupied active sites identified by the method according to the invention and a reference method measuring enzyme kinetics

| Designation | Concentration of the substance, μmol · l$^{-1}$ | Avi-PSMA | | | Avi-GCPIII | |
|---|---|---|---|---|---|---|
| | | Percentage of occupied active sites | $K_i$ determined, nmol · l$^{-1}$ | $K_i$ (enzyme kinetics), nmol · l$^{-1}$ | Percentage of occupied active sites | $K_i$ determined, nmol.l$^{-1}$ |
| Substance 1 | 1 | 99.86 | 0.7 | 0.4 | 96.4 | 24 |
| Substance 2 | 1 | 99.964 | 0.2 | 0.2 | 99.18 | 5 |
| Substance 3 | 1 | 89 | 56 | 40 | 54 | 570 |
| Substance 4 | 1 | 99.982 | 0.09 | 0.06 | 86 | 110 |
| Substance 5 | 1 | 99.991 | 0.04 | 0.09 | 95.0 | 35 |
| Substance 6 | 1 | 92.9 | 36 | 50 | 40 | 1 000 |
| Substance 7 | 1 | 99.915 | 0.4 | 0.3 | 95.5 | 31 |
| Substance 8 | 1 | 99.63 | 2 | 2 | 87 | 96 |
| Substance 9 | 1 | 99.81 | 1 | 1 | 96.3 | 26 |
| Substance 10 | 113 | 99.0 | 550 | 260 | 88 | 10 000 |
| Substance 11 | 85 | 75 | 13 000 | 4 200 | 85 | 9 900 |
| Substance 12 | 1 000 | 60 | 310 000 | 230 000 | 22 | ~2 400 000 |
| Substance 13 | 1 000 | 86 | 76 000 | 31 000 | 60 | 440 000 |
| Substance 14 | 1 000 | 94.9 | 25 000 | 12 000 | 38 | ~1 100 000 |
| Substance 15 | 1 000 | 82 | 100 000 | 23 000 | 64 | 380 000 |

The different number of digits for the percentage of occupied active sites by the tested substance corresponds to different measurement accuracies at different occupancy percentage. $K_i$ derived from occupancy percentage less than 50 percent are considered as less reliable. Important is also that by means of said testing, first inhibitors selective for Avi-PSMA compared to Avi-GCPIII were found, wherein determination, very similar $K_i$ values are obtained, irrespective of the concentration of the tested substances.

Figure 12:
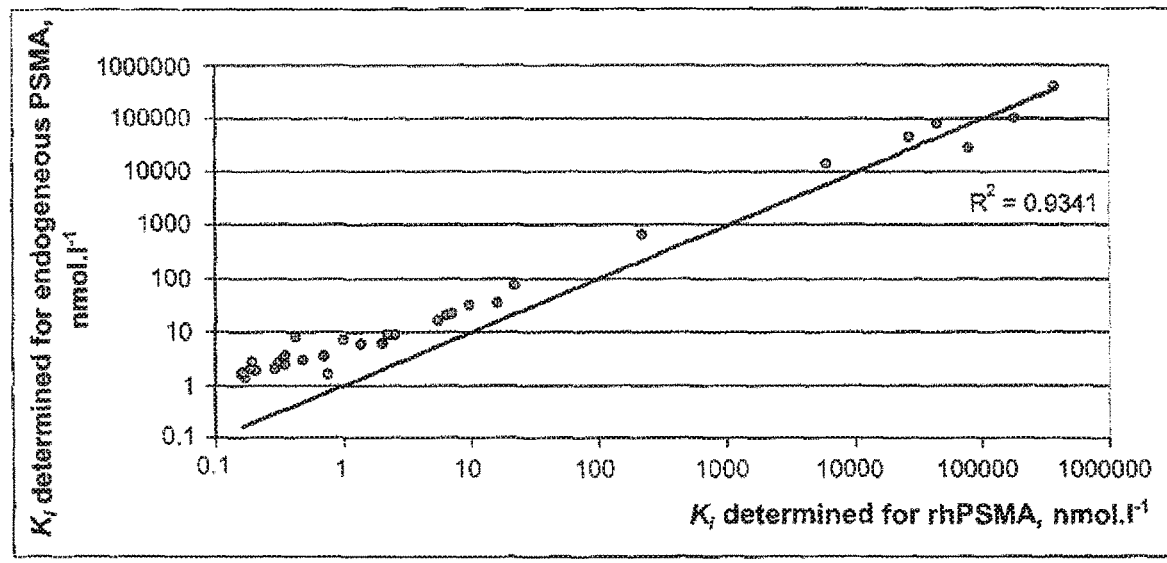
FIG. 12 shows the correlation of the inhibition constants $K_i$ of various substances measured with the method disclosed herein for rhPSMA (x-axis) and endogenous PSMA from plasma (y-axis).

The procedure described in the preceding paragraph allows testing of the inhibitory potency of substances also against an endogenous enzyme; and therefore inhibitory constants of set of 36 substances against not only rhPSMA but also endogenous PSMA contained in human blood plasma were determined with the same method as in the preceding paragraph. To determine the inhibitory potency towards rhPSMA, solution of rhPSMA at a concentration of 2 pg·μl$^{-1}$ in TBST' was applied to the wells and the ssPSMA detection probe was used at a concentration of 60 pmol·l$^{-1}$ in TBST', while for determination of inhibitory potency towards endogenous PSMA, citrate blood plasma tenfold diluted in TBST' was applied to the wells and the ssPSMA detection probe was used at a concentration of 300 pmol·l$^{-1}$ in TBST'. Decrease in amount of bound detection probe was measured again at a single concentration for each tested substance only. From the measured data, we calculated $\Delta C_q$, the percentage of active site of the enzyme occupied with tested substances and the $K_i$ of the tested substances by the same procedure as previously described ($K_d$=60 pmol·l$^{-1}$ for ssPSMA and rhPSMA in TBST; $K_d$=300 pmol·l$^{-1}$ for ssPSMA and endogenous PSMA in TBST', both determined in Example 1e). Concentration of the tested substance, the percentage of active sites of the enzymes occupied with them and their measured inhibition constants towards rhPSMA or endogenous PSMA are summarized in Table 9; comparison of the inhibition constants measured for rhPSMA and endogenous PSMA is plotted graphically in FIG. 12. Very similar results were obtained by a procedure wherein the solution of rhPSMA was first mixed with the tested substance and then with the detection probe and the resulting mixture was added to the multiwell plate with immobilized antibody 2G7. The range of the measured $K_i$ was in the range of tens pmol·l$^{-1}$ to hundreds nmol·l$^{-1}$; two of tested substances did not inhibit at all. The graph clearly documents a very good correlation between the inhibition constants for both proteins; the value of reliability $R^2$ for direct correlation between the $K_i$ determined for both forms of PSMA was 0.93. Yet $K_i$ values measured for endogenous PSMA were on average five times higher than for rhPSMA, but this is probably due to the fact that it is a slightly different form of the protein that is produced in insect cells which lacks the transmembrane and intracellular part. Differences in $K_i$ are in line with the fact that the $K_d$ of detection probe for endogenous PSMA was approximately five times higher than for rhPSMA. Larger differences observed for subnanomolar inhibitors are given by exceeding the linear range of the determination of endogenous PSMA, which is smaller due to the very small amount of PSMA in blood plasma. More accurate results for endogenous PSMA would be achieved using lower concentration of these inhibitors or larger quantities of blood plasma.

Even wider range of inhibition constants of tested substances was quantitatively determined from their single tested concentration by a procedure, wherein 250 pg rhPSMA was immobilized via antibody 2G7 onto the bottom of wells in a multiwell plate and washed afterwards; the particular wells were then incubated with the mixture of particular tested substance at concentration of 100 μmol·l$^{-1}$ and of detection probe dsA3PSMA at concentration of 125 pmol·l$^{-1}$ in TBST' buffer with addition of 500-fold diluted casein blocker. After subsequent wash, the amount of bound detection probe was determined via qPCR and respective $K_i$ values of the substances were calculated from the difference of bound probe in wells incubated with the detection probe alone and of bound probe in wells incubated with the mixture of the detection probe and particular tested substance according to formula 15 described in the description of the invention. In this manner, inhibition constants of 40 substances were determined. As determined by enzyme kinetics described in example 1c, the inhibitory potencies of the substances were approximately evenly distributed in the range of $K_i$ values ranging from 19 pmol·l$^{-1}$ to 250 μmol·l$^{-1}$ and it was found that $K_i$ values of all substances were determined very accurately by the procedure described here: the determined values corresponded on the average to 85% of the values from enzyme kinetics and they did not differ in any case more than twofold from the values from enzyme kinetics ($R^2$=0.991). These results show, that it is possible to accurately determine the $K_i$ value of the tested substances in the range of seven logs (range of 19 pmol·l$^{-1}$ to 250 μmol·l$^{-1}$) from single tested concentration of the substances (100 μmol·l$^{-1}$) by the here described procedure.

TABLE 9

Inhibition constants of substances measured towards rhPSMA or endogenous PSMA

| Designation | Concentration of the substance, nmol · l$^{-1}$ | rhPSMA | | endogenous PSMA | |
| --- | --- | --- | --- | --- | --- |
| | | Percentage of occupied active sites | $K_i$ determined, nmol · l$^{-1}$ | Percentage of occupied active sites | $K_i$ determined, nmol · l$^{-1}$ |
| Substance 1 | 1000 | 99.959 | 0.21 | 99.65 | 1.8 |
| Substance 2 | 1000 | 99.966 | 0.17 | 99.73 | 1.3 |
| Substance 3 | 1000 | 95.9 | 22 | 88 | 70 |
| Substance 4 | 1000 | 99.968 | 0.16 | 99.70 | 1.5 |
| Substance 5 | 1000 | 99.932 | 0.34 | 99.36 | 3.2 |
| Substance 6 | 1000 | 96.9 | 16 | 94.0 | 32 |
| Substance 7 | 1000 | 99.915 | 0.43 | 98.5 | 7.9 |
| Substance 8 | 1000 | 99.84 | 0.81 | N/A | N/A |
| Substance 9 | 1000 | 99.928 | 0.36 | 99.55 | 2.3 |
| Substance 10 | 100000 | 99.57 | 220 | 98.7 | 650 |
| Substance 11 | 100000 | 89 | 6100 | 78 | 14000 |
| Substance 12 | 1000000 | 57 | 380000 | 55 | 410000 |
| Substance 13 | 1000000 | 73 | 180000 | 83 | 100000 |
| Substance 14 | 1000000 | 86 | 80000 | 94.8 | 28000 |
| Substance 15 | 1000000 | 91.7 | 45000 | 87 | 78000 |
| Substance 16 | 1000 | 99.961 | 0.19 | 99.48 | 2.6 |
| Substance 17 | 1000 | 99.49 | 2.5 | 98.3 | 8.7 |
| Substance 18 | 1000 | 98.7 | 6.4 | 96.3 | 19 |
| Substance 19 | 1000 | 98.6 | 7.0 | 95.9 | 21 |
| Substance 20 | 1000 | 99.56 | 2.2 | 98.3 | 8.4 |
| Substance 21 | 1000 | 99.938 | 0.31 | 99.52 | 2.4 |
| Substance 22 | 1000 | 99.962 | 0.19 | 99.60 | 2.0 |

TABLE 9-continued

Inhibition constants of substances measured towards rhPSMA or endogenous PSMA

| | Concentration | rhPSMA | | endogenous PSMA | |
|---|---|---|---|---|---|
| Designation | of the substance, nmol·l$^{-1}$ | Percentage of occupied active sites | $K_i$ determined, nmol·l$^{-1}$ | Percentage of occupied active sites | $K_i$ determined, nmol·l$^{-1}$ |
| Substance 23 | 1000 | 99.86 | 0.72 | 99.31 | 3.5 |
| Substance 24 | 1000 | 98.1 | 9.4 | 94.1 | 31 |
| Substance 25 | 1000 | 98.9 | 5.5 | 97.1 | 15 |
| Substance 26 | 1000 | 99.903 | 0.48 | 99.45 | 2.8 |
| Substance 27 | 1000 | 99.930 | 0.35 | 99.35 | 3.3 |
| Substance 28 | 1000 | 99.73 | 1.37 | 98.8 | 5.9 |
| Substance 29 | 1000 | 99.967 | 0.16 | 99.67 | 1.7 |
| Substance 30 | 1000 | 99.85 | 0.75 | 99.69 | 1.6 |
| Substance 31 | 1000 | 99.60 | 2.0 | 98.9 | 5.7 |
| Substance 32 | 1000 | 99.80 | 1.0 | 98.7 | 6.7 |
| Substance 33 | 1000 | 99.941 | 0.30 | 99.60 | 2.0 |
| Substance 34 | 1000000 | 94.9 | 27000 | 91.7 | 45000 |
| Substance 35 | 100000 | 0 | does not inhibit | 0 | does not inhibit |
| Substance 36 | 100000 | 0 | does not inhibit | 0 | does not inhibit |

Designation of the substances meets the description in the preceding table. The different number of digits for the percentage of occupied active sites (with the tested substance) corresponds to different determination accuracies at different percentage of occupancy.

1j: Determination of PSMA in Solution Using Chemiluminescent Detection

100 µl of the 2G7 antibody solution at a concentration of 2.5 ng·µl$^{-1}$ in TBS was applied to the wells of 96-well Nunc Maxisorb microplates (cat. no. 437111) and incubated at room temperature for 1 hour. Content of the wells was then tapped out and the wells were washed three times with 200 µl of TBS. 200 µl of casein blocking agent five times diluted in TBS was then applied to the wells and incubated for 18 hours and 30 minutes at room temperature. Content of the wells was then tapped out and the wells were washed three times with 200 µl TBST. 100 µl of rhPSMA standard solution of various known concentrations in TBST', the resulting applied amount in the range of 1 ng to 1 pg, was then added to the wells. Zero controls without rhPSMA were also included, all in two replicates. After 2 hours and 45 minutes incubation at room temperature, the content of the wells was tapped out and the wells were washed three times with 200 µl TBST. Finally, 100 µl of a solution of the NeuHRP_dsbiotPSMA detection probe at a concentration of 600 pmol·l$^{-1}$ in CaSDS was added to the wells. NeuHRP_dsbiotPSMA detection probe was prepared by mixing 6.1 µl of neutravidin-HRP conjugate solution (Pierce, cat. no. 31001) at a concentration of 1 mg·ml$^{-1}$ with 10 µl solution of biotinylated detection probe dsbiotPSMA at 10 nmol·l$^{-1}$ (corresponding fourfold molar excess compared to neutravidin-HRP conjugate) in TBS buffer. After overnight incubation on ice, the resulting complex was purified from the remaining free dsbiotPSMA probe by ultrafiltration on a membrane with a permeability cutoff of 100 kDa; the original solution was diluted hundredfold in sum. The final concentration of the detection probe in the complex was determined by qPCR by comparison with a standard dilution series of ssPSMA as described in Example 1d. After incubation for 1 hour at room temperature, the content of the wells was tapped out and the wells were washed ten times with 200 µl of TBST. 160 µl of chemiluminescent substrate was then added to the wells (aqueous solution of 4-iodophenol (Acros Organics, cat. no. 122390100) at a concentration of 2 mmol·l$^{-1}$, luminol (5-amino-2,3-dihydro-1,4-phthalazinedion, Sigma Aldrich, cat. no. A8511) at a concentration of 2.5 mmol·l$^{-1}$; 3.2% DMSO (vol./vol.), 0.02% (wt./vol.) of hydrogen peroxide and 0.1 mol·l$^{-1}$ Tris-HCl, pH 8.0) and the luminescence was measured in each well using a Tecan reader Infinite M1000.

The dynamic range of detection was observed in the range of the applied amount of rhPSMA 1 ng to 1 pg. Detection limit of 1 pg indicates that it is a more sensitive determination than nowadays the most sensitive available determination of PSMA by ELISA (Sokoloff et al. 2000, Prostate, p. 150). Measured values of the luminescence duplicate measurements are summarized in Table 10.

TABLE 10

Determination of rhPSMA in a using chemiluminescent detection

| amount of rhPSMA, pg | luminescence (1), relative units | luminescence (2), relative units |
|---|---|---|
| 0 | 2071 | 2011 |
| 1 | 2455 | 2477 |
| 10 | 17055 | 16840 |
| 100 | 308210 | 320440 |
| 1000 | 4059300 | 4351800 |

1k: Determination of PSMA Catalytic Activity for Substrate Hydrolysis

Following the procedure described in section 1i, 20 pg of Avi-PSMA was immobilized to the bottom of the wells via immobilized neutravidin and subsequently incubated with the dsA3PSMA detection probe at a concentration of 35 pmol·l$^{-1}$ and simultaneously with various concentrations of the folyl-γ-L-glutamate substrate in the range of 10 nmol·l$^{-1}$ to 100 µmol·l$^{-1}$ for 40 minutes, and after washing, the amount of bound probe was determined with qPCR. $K_M$ of the substrate (corresponding to IQ was calculated from the $\Delta C_q$ difference between wells with the highest concentration of the substrate and the wells with only the detection probe according to the equation (15). Based on the this calculated $K_i$ and the $\Delta C_q$ difference measured for each initial concentration of the substrate, final substrate concentrations at the end of incubation, $S_f$, were then calculated according to the same formula, and according to equation (17) described above in the description of the invention, catalytic efficiency $k_{cat}$ was calculated. At an initial concentration of folyl-γ-L-glutamate 107 nmol·l$^{-1}$, 80% is cleaved during incubation, which corresponds to a $k_{cat}$ of 1.2 s$^{-1}$. At a concentration of 336 nmol·l$^{-1}$, 43% was cleaved, corresponding to $k_{cat}$ of 2.3 s$^{-1}$ and at a concentration of 1049 nmol·l$^{-1}$, 16% was cleaved, corresponding to $k_{cat}$ of 2.6 s$^{-1}$. Obtained $k_{cat}$ values are in conformity with the $k_{cat}$ value of 5 s$^{-1}$ obtained from enzyme kinetics as described in Section 1c.

Example 2: Detection of HIV-1 Protease, Testing Potency of HIV-1 Protease Inhibitors 2a: Preparation of an HIV-1 Protease Inhibitor with a Linker and an Activated NHS Ester The detection probe for HIV-1 protease was prepared by linking of a HIV-1 protease inhibitor with linker with terminal NHS-ester (Compound 7) with the amino group of the DNA oligonucleotide. Compound 8, prepared by reaction of Compound 7 with ethanolamine was used for determination of the impact of linking of the DNA oligonucleotide on the inhibition potency. All compounds were purified and characterized as described in example 1a.

Ritonavir (RTV, available under the brand name Norvir from Abbott Laboratories) was isolated from commercially available capsules in which RTV is suspended in an oily mixture of rather nonpolar compounds. 50 tablets (100 mg RTV each) were cut open and the oily substance was squeezed out into a bottom round shaped 2l flask. 200 ml of hexane was added along with 500 ml of diethylether. The resulting suspension was triturated and sonicated for 3 hours until all oil turned into a white precipitate or was dissolved in solvents. This precipitate was filtered and again triturated/sonicated in pure diethylether, after which the pure RTV was filtered. 3.6 g of RTV was obtained (yield 72%). The purity of RTV was determined by HPLC and was well above 99%.

Preparation of thiazol-5-ylmethyl ((2S,3S,5S)-5-amino-3-hydroxy-1,6-diphenylhexan-2-yl)carbamate (Compound 5) by partial hydrolysis of ritonavir (RTV): 1.00 g of RTV was dissolved in 50 ml of dioxane in a bottom round flask. 50 ml of concentrated hydrochloric acid was added and the resulting mixture was stirred at 65° C. for 20 hours (note that different temperature and/or time lead to different cleavage products). After 20 hours the mixture was let to cool down to RT. The mixture was neutralized by addition of $K_2CO_3$ until the resulting mixture showed basic pH. The solvents were concentrated using rotary evaporater to roughly 50 ml and the slurry was diluted by 150 ml of water and washed 3 times by 100 ml of EtOAc. The water phase was discarded and organic phase was dried and evaporated. 885 mg of crude mixture was obtained and was used in the next reaction without further purification (purity approx. 80% as determined by analytical HPLC).

For spectral determination, 50 mg were purified using preparative HPLC (gradient: 20-50% (vol./vol.) ACN in 40 minutes, RT 15 minutes). Analytical HPLC RT=17.3 min.

Result of analysis by NMR (500 MHz, DMSO-d6): δ 9.06 (d, $^4$J=0.8, 1H, N—CH—S), 7.84 (q, $^4$J=0.8, 1H, S—C—CH—N), 7.81 (bs, 3H, NH$_3$+), 7.32-7.15 (m, 10H, 2×Ph-), 7.20 (bs, 1H, NH), 5.50 (bs, 1H, OH), 5.15 (dd, $J_{gem}$=13.2, $^4$J=0.8, O—CH$_2$), 5.11 (dd, 1H, $J_{gem}$=13.2, $^4$J=0.8, COO—CH$_2$), 3.69 (m, 1H, HO—CH), 3.67 (m, 1H, HO—CH—CH—NH), 3.50 (bm, 1H, NH$_3$+—CH), 2.87 (dd, 1H, $J_{gem}$=14.0, J=6.4, NH$_3$+—CH—CH$_2$-Ph), 2.80 (dd, 1H, $J_{gem}$=14.0, J=7.3, 1H, NH$_3$+—CH—CH$_2$-Ph), 2.79 (dd, 1H, $J_{gem}$=13.7, J=3.7, 1H, NH—CH—CH$_2$-Ph), 2.79 (dd, $J_{gem}$=13.7, J=10.5, 1H, NH—CH—CH$_2$-Ph), 1.58 (bs, 2H, OH—CH—CH$_2$—CH).

Result of analysis by $^{13}$C NMR (125.7 MHz, DMSO-d6): δ 155.39 (O—C—N), 155.77 (N—CH—S), 143.23 (S—C—CH—N), 139.52 (Ph), 136.37 (Ph), 134.14 (S—C—CH—N), 129.61 (Ph), 129.18 (Ph), 128.81 (Ph), 128.23 (Ph), 127.07 (Ph), 126.12 (Ph), 69.81 (HO—CH), 57.49 (COO—CH$_2$), 56.94 (HO—CH—CH—NH), 50.87 (NH$_3$+—CH), 38.71 (NH$_3$+—CH—CH$_2$-Ph), 35.69 (NH—CH—CH$_2$-Ph), 34.66 (CH—CH$_2$—CH).

Result of analysis by HRMS (ESI+): calculated mass of $C_{23}H_{28}O_3N_3S$ [M]$^+$ 426.18459; detected mass 426.18454.

Preparation of (S)-1-(((2S,4S,5S)-4-hydroxy-1,6-diphenyl-5-(((thiazol-5-ylmethoxy)carbonyl)amino) hexan-2-yl) amino)-3-methyl-1-oxobutan-2-aminium 2,2,2-trifluoroacetate (compound 6): 526 mg (1.64 mmol, 1 eq) of TBTU was added to 356 mg (1.64 mmol, 1 eq) BOC-Val, dissolved in 1.5 ml of DMF along with 690 µl of DIEA (3.94 mmol, 2.4 eq). The crude hydrolysate of RTV (700 mg, 1.64 mmol, 1 eq), dissolved in 1 ml of DMF, was added after 5 minutes of stirring in one portion. The reaction was left overnight and the DMF was rotary evaporated. The reaction mixture was dissolved in 50 ml of EtOAc and washed two times by saturated NaHCO$_3$, two times by 10% KHSO$_4$ (wt./vol.) and once with brine. The organic mixture was dried, evaporated and the product was purified using Flash chromatography (TLC analysis: EtOAc, Rf=0.65). Product was further dissolved in 5 ml of hot EtOAc and 5 ml of diethyl ether were added. The resulting gel was filtrated and dried to give very pure (>99%, HPLC) 250 mg of product. The BOC protected compound was dissolved in pure TFA and sonicated for 10 minutes. The TFA was removed by flow of nitrogen and the resulting oil was dissolved in water/ACN and lyophilized to remove residual TFA. Overall yield: 25% (the low yield was due to discarded fractions with impurities from TLC).

Analytical HPLC RT=17.4 min.

Result of analysis by $^1$H NMR (500 MHz, DMSO-d6): δ 9.06 (d, $^4$J=0.8, 1H, N—CH—S), 8.24 (d, J=8.2, 1H, —NH—CO), 8.00 (bd, J=5.2, 3H, —NH$_3$+), 7.85 (q, $^4$J=0.8, 1H, S—C—CH—N), 7.28-7.13 (m, 10H, 2×Ph-), 6.94 (d, J=9.4, 1H, NH—CO—O), 5.12 (d, $^4$J=0.8, 2H, O—CH$_2$), 4.16 (m, 1H, CH—NH—CO), 3.78 (m, 1H, CH—NH$_3$+, partial overlap with water residual peak), 3.58 (td, J=6.8, J=2.0, 1H, CH—OH), 3.48 (m, 1H, Ph-CH$_2$—CH—NH), 2.72-2.67 (m, 4H, 2×CH—CH$_2$-Ph), 2.00 (m, 1H, CH—(CH$_3$)$_2$), 1.50 (m, 1H, OH—CH—CH$_2$), 1.43 (m, 1H, OH—CH—CH$_2$), 0.89 (d, J=6.8, 3H, —CH$_3$), 0.84 (d, J=6.8, 3H, —CH$_3$).

Result of analysis by $^{13}$C NMR (125.7 MHz, DMSO-d6): δ 167.33 (CO Val), 158.33 (q, $J_{C,F}$=34.4, CF$_3$COO—), 155.79 (O—C—N), 155.71 (N—CH—S), 143.23 (S—C—CH—N), 139.50 (Ph), 138.55 (Ph), 134.23 (S—C—CH—N), 129.56 (Ph), 129.17 (Ph), 128.30 (Ph), 128.25 (Ph), 126.26 (Ph), 126.09 (Ph), 116.44 (q, $J_{C,F}$=294.8, CF$_3$—COO$^-$), 68.90 (HO—CH), 57.56 (CO—CH—NH$_3$), 57.44 (COO—CH$_2$), 55.74 (HO—CH—CH—NH), 47.98 (CONH—CH), 39.75 (NH—CH—CH$_2$-Ph), 37.77 (—CH$_2$—CH—CH—), 37.33 (Ph-CH$_2$—CH—NH), 30.04 (CH(CH$_3$)$_2$), 17.26 and 18.69 (2×CH$_3$).

Result of analysis by HRMS (ESI+): calculated mass of $C_{28}H_{37}O_4N_4S$ [M]$^+$ 525.25300, detected mass 525.25292.

Preparation of (5S,6S,8S,11S)-2,5-dioxopyrrolidin-1-yl 5,8-dibenzyl-6-hydroxy-11-isopropyl-3,10,13-trioxo-1-(thiazol-5-yl)-2,16,19,22,25,28-hexaoxa-4,9,12-triazahentriacontan-31-oate (compound 7): 50 mg (78.3 nmol, 1 eq) of NHS-PEG5-NHS (Broadpharm) was dissolved in 0.5 ml of DMF along with 30 µl (172 nmol, 2.2 eq) of DIEA and 46 mg (86.1 nmol, 1 eq) of compound 6 dissolved in 0.5 ml of DMF was added dropwise during 30 minutes. The reaction was left to react overnight, the reaction mixture was then rotary evaporated and the crude product was purified using preparative HPLC (gradient: 20-50% (vol./vol.) ACN in 40 minutes, RT 32 minutes). 30 mg were isolated after lyophilization with purity well above 99% as determined by analytical HPLC (yield 40%). Analytical HPLC RT=21.2 min.

Result of analysis by HRMS (ESI+): calculated mass of $C_{46}H_{63}O_{14}N_5S$ $[MNa]^+$964.39844, detected mass 964.39922.

Preparation of thiazol-5-ylmethyl ((24S,27S,29S,30S)-27-benzyl-1,29-dihydroxy-24-isopropyl-4,22,25-trioxo-31-phenyl-7,10,13,16,19-pentaoxa-3,23,26-triazahentriacontan-30-yl)carbamate (compound 8): 4 mg (4.25 µmol, 1 eq) of compound 7 were dissolved in 200 µl of DMF and 3 µl (49.7 µmol, 12 eq) of ethanolamine were added into the mixture along with 7 µl (42.5 µmol, 10 eq) of DIEA and the whole reaction mixture was left stirring overnight. The solvent was rotary evaporated and the mixture was dissolved in ACN/water and lyophilized 3 times (to remove ethanolamine). The compound was used in biochemical studies without further purification (the only contaminant is NHS, otherwise purity was higher than 98%). Analytical HPLC RT=19.0 min.

Result of analysis by HRMS (ESI+): calculated mass of $C_{44}H_{65}O_{12}N_5S$ $[MNa]^+$910.42426, detected mass 910.42479.

2b: Preparation of a Detection Probe for Selective Binding of the HIV-1 Protease Detection probe for quantification of HIV-1 protease was prepared by reacting the iqPCR_amino oligonucleotide with Compound 7 in the modification buffer: 8 µl of DMSO was added to 10 µl of the oligonucleotide in the modification buffer (10.2 nmol; 1 eq), and after mixing, the resulting solution was added to 2 µl of a solution of Compound 7 (205 nmol; 20 eq) in anhydrous DMSO. This mixture was incubated for 4.5 hours at room temperature, then 480 µl of TBS was added and incubation continued at the same temperature overnight.

The resulting detection probe (shown in FIG. 13) was purified from the hydrolysis products of compound 7 by ultrafiltration on Amicon Ultra 0.5 ml 3K column, the retentate volume was nine times consecutively tenfold diluted in TBS, and the concentration of the detection probe measured spectrophotometrically. The probe prepared this way was used to determine the inhibition constant in an enzyme assay (hereinafter ssHIV1/TBS); for characterization by LC-MS, the probe was re-purified on Amicon Ultra 0.5 ml 3K column and the volume of the retentate was again five times consecutively tenfold diluted in distilled water (hereinafter ssHIV1). For determination of the concentration of HIV-1 protease and for testing of HIV-1 protease inhibitors, the probe was once again purified by ultrafiltration on Amicon Ultra 0.5 ml 10K column so that the volume of the retentate was first seven times consecutively tenfold diluted in double distilled water and then five times consecutively tenfold in TBS buffer and the concentration of the detection probe was measured Spectrophotometrically (OD 1=1744 pmol). Finally, the probe was diluted to a concentration of 5 nmol·l$^{-1}$ in TBS and exposed to thermal pairing in a volume of 50 µl, according to the procedure described in Example 1b. To verify the efficiency of conjugation, the ssHIV1 sample was analysed by LC/ESI-MS, the procedure was identical to that of the original iqPCR_amino oligonucleotide and the ssPSMA detection probe (described in Example 1b). The result was one intense absorption peak at 260 nm with retention time 5.18 minutes and two associated low intensity peaks with retention times of 4.94 and 4.99 min and the corresponding masses of 17035.34 and 17085.99 (mass difference from original oligonucleotide 53.47 and 104.12). The initial mass of around 16981.87 was not represented in the m/z spectra of these peaks. These two new masses were represented in a small intensity also at the beginning and at the end (time 4.92 and 5.00 min) of the peak in the analysis of ssPSMA, but not in the peak of the original iqPCR_amino. It is therefore likely a salt or an adduct formed with an impurity in DMSO, since this solvent is the only common feature of both modified oligonucleotides and was not used to dissolve the original oligonucleotide. The mass of 17809.07 was unambiguously assigned to the intense peak and the mass difference compared to the original iqPCR_amino was 827.20. The most abundant mass predicted for the detection probe is 17806.29 at molecular weight of 17810.29 and the expected difference in mass of the ssHIV1 conjugate and the original iqPCR_amino is 826.38 (according to the ChemBioDraw program). Purity of the ssHIV1 detection probe (reaction conversion) was about 80% according to an integration of the absorbances of peaks at 260 nm from the LC-MS analysis. Such conversion is fully sufficient for further utilization, and the sample was not further purified.

2c: Determination of Inhibition Constants of the Prepared Compounds and the Detection Probe HIV-1 protease enzyme used in the assay was expressed, refolded and purified as described in (Kozisek et al. 2008, Journal of Virology, p. 5869; Weber et al. 2002, Journal of Molecular Biology, p. 739). The concentration of HIV-1 protease in the final composition was determined by titration of the active site with brecanavir inhibitor; the enzyme was stored frozen in aliquots at −20° C. before use. Concentration of ssHIV1/TBS was determined spectrophotometrically, the concentration of compound 8 was derived from its weight on an analytical balance.

Inhibition analyses were performed using a chromogenic peptide substrate KARVNle*NphEANle-NH$_2$ as described in (Weber et al. 2002, Journal of Molecular Biology, p. 739). Reactions were carried out in 100 mmol·l$^{-1}$ sodium acetate and 300 mmol·l$^{-1}$ NaCl at pH 4.7 in a total volume of 1 ml. The final substrate concentration was maintained near $K_M$ (i.e. 16 nmol·l$^{-1}$), the total amount of the protease in the reaction was from 6 to 8 pmol. Various concentrations of Compound 8 (dissolved in DMSO) or ssHIV1/TBS were added to the mixture. Final DMSO concentration was always lower than 2.5% (vol./vol.). Substrate hydrolysis was monitored by the decrease in absorbance at 305 nm in a UV-Vis spectrometer UNICAM UV500 (Thermo Scientific). Data were subsequently analysed using the equation for competitive inhibition by Williams and Morrison in the GraFit program. $K_i$=2.3±0.1 nmol·l$^{-1}$ was thus measured for compound 8, while $K_i$ was 0.23±0.03 nmol·l$^{-1}$ for ssHIV1/TBS.

2d: Detection of HIV-1 Protease and Testing of HIV-1 Protease Inhibitors by Direct Adsorption on a Solid Carrier In this embodiment, the stock solution of purified HIV-1 protease at a concentration of 244 ng·μl$^{-1}$ in 10% glycerol (vol./vol.) was diluted to 10 ng·μl$^{-1}$ of the protease in TBS and 10 μl was applied to the bottom of the wells of 96-well plates FrameStar 480/96; the same volume of only pure TBS was applied to wells of the zero controls. After 15 minutes incubation at room temperature, the content of the wells was tapped out and the wells were washed three times with 200 μl of TBS. 200 μl of casein blocking agent five times diluted in TBS was then applied to the bottom of the wells and incubated for 1 hour at room temperature. The content of the wells was tapped out and the wells were washed three times with 200 μl of TBS. 10 μl of ssHIV1 detection probe was added in an aqueous solution of 20 mmol·l$^{-1}$ MES with 750 mmol·l$^{-1}$ NaCl and 0.05% Tween 20 (vol./vol.) at pH 6.0 (hereinafter "MEST"). After 45 minutes incubation at room temperature, the content of the wells was tapped out and the wells were washed eight times with 200 μl of TBST. 10 μl of qPCR mixture of the same composition as in the case of no template control in Example 1d was then added to the bottom of the wells and the amount of bound detection probe was determined by qPCR as described in Example 1d.

With the method described, the amount of bound detection probe was measured depending on the concentration in which it was applied, and it was found that the dissociation constant of the probe for the immobilized HIV protease is higher than the highest used concentration of the probe, i.e. 32 nmol·l$^{-1}$. At the detection probe concentration of 3.2 nmol·l$^{-1}$, the difference in the measured $C_q$ in the wells of zero control and in the wells with 100 ng of sorbed HIV protease was approximately eight cycles, which corresponds to two orders of magnitude difference in the amount of bound probe. Under the same conditions, it was verified that the addition of DMSO at 0.1%, 1% or 10% (vol./vol.) to the solution of the probe did not affect selective or non-selective binding of the probe.

Figure 14:
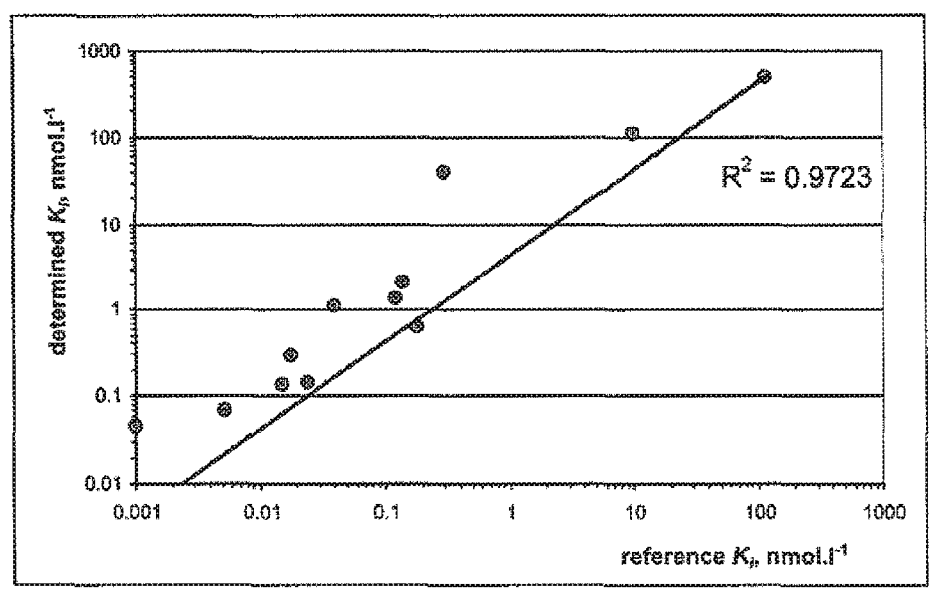
FIG. 14 shows a correlation of the inhibition constants $K_i$ of various substances towards HIV protease measured with the method disclosed herein employing direct antigen sorption at pH 6.0 (average of two independent measurements, y-axis) and with reference enzyme kinetics at pH 4.7 (x-axis). For greater clarity, both axes are in a logarithmic scale.

Finally, various concentrations of 12 different HIV-1 protease inhibitors were added to the detection probe solutions applied into the wells and their inhibition constants were determined by the procedure described in Example 1i. For calculations, only the values of occupancy of active sites in the range from 50 to 99% were used and the corresponding concentrations of the inhibitor. Only a single high concentration of the substance was sufficient for qualitative information about the ability of the tested substances to inhibit HIV protease, however, for a quantitative information, due to the dynamic range of two orders of magnitude, it was necessary to test a series of tenfold diluted concentrations. Obtained $K_i$ values were then compared with reference values $K_i$ref obtained from enzyme kinetics method described in example 2c, whereby it was found that the values of both methods correlate very well with each other, as seen from a graphical comparison of the results of both methods in FIG. 14; the reliability value $R^2$ of the linear correlation between $K_i$ determined with our method and $K_i$ determined with reference enzyme kinetics was 0.97. Nevertheless, the average $K_i$ measured by the method of the invention is considerably higher than $K_i$ref (on average more than tenfold), which is probably due to the different pH used in both methods, as it is known that also determining $K_i$ref with enzyme kinetics at pH 4.7 (reference values determined at this pH) and at pH 6.0 (our method performed at this pH) leads to different results. $K_i$ref determined at pH 6.0 are considerably higher than at pH 4.7 exactly as are values determined by our method. $K_i$ref values and the measured $K_i$ values from two independent experiments are summarized in table 11.

TABLE 11

Comparison of $K_i$ values of inhibitors, measured in two independent experiments, and the respective $K_i$ref

| Inhibitors of HIV PR | $K_i$ (1), nmol·l$^{-1}$ | $K_i$ (2), nmol·l$^{-1}$ | $K_i$ref, nmol·l$^{-1}$ |
|---|---|---|---|
| saquinavir | 0.61 | 1.7 | 0.04 |
| ritonavir | 0.16 | 0.11 | 0.015 |
| indinavir | 1.3 | 1.5 | 0.12 |
| amprenavir | 0.80 | 0.44 | 0.184 |
| lopinavir | 0.18 | 0.41 | 0.018 |
| atazanavir | 0.11 | 0.18 | 0.024 |
| tipranavir | 1.3 | 2.9 | 0.14 |
| darunavir | 0.03 | 0.11 | 0.0053 |
| brecanavir | 0.04 | 0.05 | 0.001 |
| Substance 37 | 600 | 380 | 116 |
| Substance 38 | N/A | 110 | 10 |
| Substance 39 | 40 | N/A | 0.3 |

$K_i$(1) and $K_i$(2) indicate inhibitory constants determined sequentially in two independent experiments (pH 6.0), $K_i$ref is the reference value obtained by enzyme kinetics (pH 4.7).

2e: Detection of HIV-1 Protease and Testing its Inhibitors by Binding to an Immobilized Antibody In another embodiment, 10 μl of a solution of a polyclonal antibody binding the HIV-1 protease (MyBiosource, MBS536030) at 5 ng·μl$^{-1}$ in TBS was applied to the bottom of wells of a 96 well plate FrameStar 480/96 and incubated at room temperature for 45 minutes. Content of the wells was then tapped out and the wells were washed three times with 200 μl of TBS. 200 μl of casein blocking agent five times diluted in TBS was then applied to the bottom of the wells and incubated for 3 hours at room temperature, then the content of the wells was tapped out and the wells were washed three times with 200 μl TBST. Subsequently, 10 μl of purified HIV-1 protease solution at different concentrations in TBST was applied to the bottom of wells. After incubation for 1 hour at room temperature, the content of the wells was tapped out and the wells were washed three times with 200 μl TBST. Then, 10 μl of ssHIV1 solution detection probe in TBST was added. Further procedure was the same as in Example 2d.

Figure 15:
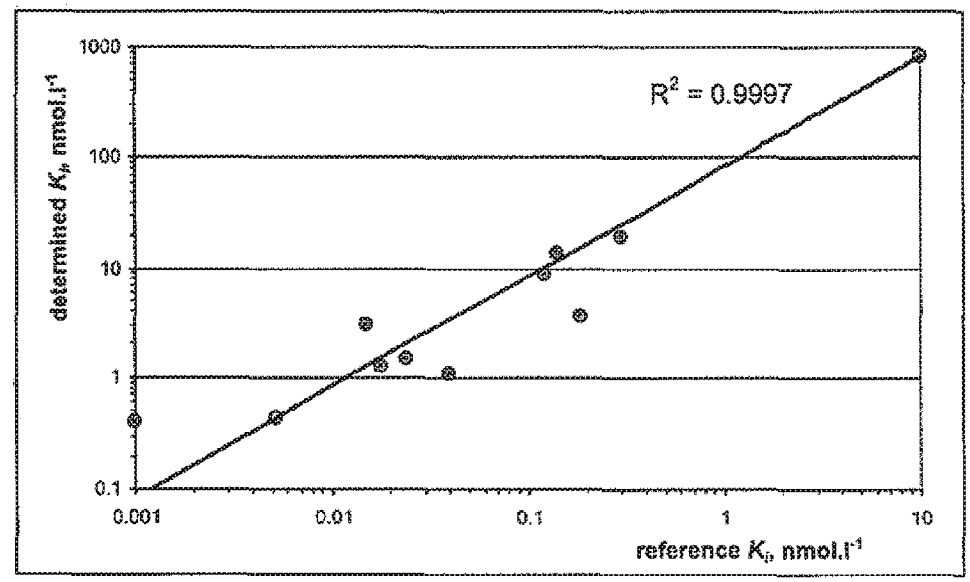
FIG. 15 shows a correlation of the inhibition constants $K_i$ of various substances towards HIV protease measured with the method disclosed herein at pH 7.4 (y-axis) and with reference enzyme kinetics at pH 4.7 (x-axis). For greater clarity, both axes are in a logarithmic scale.

This procedure showed that the range of detection reached from 100 ng to 1 ng of HIV-1 protease, when detection probe was applied at a concentration of 10 nmol·l$^{-1}$, and $\Delta C_q$ between wells with 100 ng of the protease and without it was nine cycles. It was also found that the addition of casein blocking agent to the detection probe solution in a final twothousand-fold dilution increased the $\Delta C_q$ between wells with 100 ng of the protease and without it to twelve cycles, corresponding to thousand-fold difference in binding of the probe; therefore the probe was diluted in TBST buffer containing casein blocking agent for further determinations. In the case that instead of the detection probe solution, a solution of the original oligonucleotide without the iqPCR_amino ligand portion was used, no binding was observed, even when applying an amount of 100 ng of HIV-1 protease, confirming the selectivity of the detection probes binding via the ligand portion. The procedure was also tested for the influence of solvents added to the solution of the detection probe; at final concentrations of 0.1%, 1% and 10% (vol./vol.) of DMSO, acetonitrile or methanol had no effect on binding of detection probe, either selective to the protease or the non-selective to the surface without the protease. Finally, various concentrations of 12 different inhibitors of HIV-1 protease were added to the detection probe solutions applied to the wells and their inhibition constants were determined by the procedure described in Example 1i, only the values of occupancy of active sites in the range from 50 to 99% were used and the corresponding concentrations of the inhibitor. A number of substances that do not inhibit the HIV-1 protease were gradually added at high concentration (1 mmol·l$^{-1}$) to check the correctness of the determination (substances), and none of them lead to decrease in the amount of bound detection probe, i.e. no false positive results were observed. For qualitative information about the ability of tested substances to inhibit HIV protease, a single high concentration of the substance is sufficient; however, for a quantitative information, due to the dynamic range of two to three orders of magnitude, it was necessary to test a series of tenfold diluted concentrations. $K_i$ values obtained were compared to reference $K_i$ref values obtained by enzyme kinetic method described in example 2c, and it was found that the values from both methods correlate very well, as is apparent from the graphical comparison of the results of both methods in FIG. 15; the value of reliability $R^2$ of direct correlation between $K_i$ determined with our method and $K_i$ determined with reference enzyme kinetics was 1.00. Nevertheless, the average $K_i$ measured by the method of the invention is considerably higher than $K_i$ref (on average more than a hundred-fold), which is probably due to the different pH used in both methods, as discussed in Example 2d. In this case, the difference in pH in the enzyme kinetics (4.7) and in our process (7.4) is substantial; the corresponding difference in the concentration of $H_3O^+$ ions is almost three orders of magnitude. This difference may cause hundredfold differences in measured values. There is a practical reason to use pH 4.7 in enzyme kinetics, since HIV protease is most active at such pH, whereas at pH 7.4, its activity is too small for practical measurement and is thus difficult to determine the $K_i$ref value at pH 7.4. In this regard, our method provides improvement, since the measurement at physiological pH is apparently closer to the biological context of the clinical use of HIV protease inhibitors. $K_i$ref values and $K_i$ values measured are summarized in Table 12.

TABLE 12

Comparison of the measured values of inhibitors' $K_i$ and the respective $K_i$ref

| Inhibitors of HIV-1 PR | $K_i$, nmol · l$^{-1}$ | $K_i$ref, nmol · l$^{-1}$ |
|---|---|---|
| saquinavir | 1.1 | 0.04 |
| ritonavir | 3.0 | 0.015 |
| indinavir | 8.7 | 0.12 |
| amprenavir | 3.5 | 0.184 |
| lopinavir | 1.3 | 0.018 |
| atazanavir | 1.4 | 0.024 |
| tipranavir | 14 | 0.14 |
| darunavir | 0.44 | 0.0053 |
| brecanavir | 0.41 | 0.001 |
| Substance 37 | N/A | 116 |
| Substance 38 | 830 | 10 |
| Substance 39 | 19 | 0.3 |

$K_i$ refers to determined inhibition constants (pH 7.4), $K_i$ref to the reference value obtained from enzyme kinetics (pH 4.7).

Example 3: Detection of Carbonic Anhydrases II and IX and Testing of their Inhibitors 3a: Preparation of a Common Inhibitor of Carbonic Anhydrases II and IX, and its NHS Ester All compounds were purified and characterized as described in example 1a.

Preparation of methyl 4-(4-((tert-butoxycarbonyl)amino) butoxy)benzoate (compound 9): To a solution of 161 mg (1 eq, 1.06 mmol) of methyl 4-hydroxybenzoate, 300 mg (1.5 eq, 1.59 mmol) of tert-butyl (4-hydroxybutyl)carbamate and 400 mg (1.5 eq, 1.59 mmol) of triphenylphosphine in 10 ml of THF was added 312 µl (1.5 eq, 1.59 mmol) of DIAD in one portion and the reaction was left stirring overnight. The reaction mixture was then evaporated and the crude product was purified by column chromatography (He:EtOAc 4:1, RF=0.25; note: the methyl 4-hydroxybenzoate has identical RF with the product, therefore 1.5 eq of other reactants was used) 260 mg of white powder was obtained (yield 75%).

Result of analysis by $^1$H NMR (400 MHz, CDCl$_3$) δ 7.95 (d, J=8.9 Hz, 2H), 6.87 (d, J=8.9 Hz, 2H), 4.71 (s, 1H), 3.99 (t, J=6.2 Hz, 2H), 3.85 (s, 3H), 3.17 (dd, J=12.8, 6.3 Hz, 2H), 1.86-1.75 (m, 2H), 1.69-1.61 (m, 2H), 1.42 (s, 9H).

Result of analysis by $^{13}$C NMR (101 MHz, CDCl$_3$) δ 166.92 (s), 162.78 (s), 156.10 (s), 131.64 (s), 122.57 (s), 114.12 (s), 79.20 (s), 67.73 (s), 51.89 (s), 40.29 (s), 28.49 (s), 26.86 (s), 26.49 (s).

Result of analysis by MS (ESI+): calculated mass of $C_{17}H_{25}O_5N$ [MNa]$^+$346.17; detected mass 346.2. Preparation of 4-(4-((tert-butoxycarbonyl)amino)butoxy)benzoic acid (compound 10): 270 mg of compound 9 were dissolved in 5 ml of methanol and 5 ml of 5 mol·l$^{-1}$ NaOH was added. The mixture was refluxed until TLC analysis showed complete disappearance of compound 9 (6 hours). The reaction mixture was diluted by EtOAc (20 ml), the water phase was acidified by 10% KHSO$_4$ (wt./vol.) to acidic pH and extracted 2 more times by 20 ml of EtOAc. 240 mg of oily product which turned to crystalline white after removal of solvent traces was obtained (yield 95%).

Result of analysis by $^1$H NMR (400 MHz, CDCl$_3$) δ 8.03 (d, J=8.9 Hz, 2H), 6.91 (d, J=9.0 Hz, 2H), 4.65 (s, 1H), 4.04 (t, J=6.2 Hz, 2H), 3.27-3.20 (m, 2H), 1.91-1.78 (m, 2H), 1.69 (dd, J=14.8, 7.2 Hz, 2H), 1.44 (s, 9H).

Result of analysis by $^{13}$C NMR (101 MHz, CDCl$_3$) δ 171.51 (s), 163.46 (s), 156.20 (s), 132.42 (s), 121.92 (s), 114.28 (s), 79.42 (s), 67.86 (s), 40.36 (s), 28.56 (s), 26.89 (s), 26.53 (s).

Result of analysis by MS (ESI−): calculated mass of $C_{16}H_{22}O_5N$ [M]$^-$ 308.16; detected mass 308.2.

Preparation of tert-butyl (4-(4-(3-(4-sulfamoylphenyl) ureido)phenoxy)butyl)carbamate (compound 11): 720 mg (1 eq, 2.33 mmol) of compound 10 was dissolved in 15 ml of dry toluene and 810 µl (2 eq, 4.65 mmol) of DIEA was added. DPPA (552 µl, 1.1 eq, 2.56 mmol) was added to the reaction mixture in one portion and the reaction mixture's temperature was raised to 90° C. for 2 hours. The reaction mixture was then evaporated and dissolved in dry ACN; 601 mg (1.5 eq, 3.49 mmol) of sulfanilamide was added in one portion and reaction mixture was heated up to 60° C. overnight while stirring. All volatiles were evaporated after 12 hours and the crude product was purified by column chromatography on silica (He:EtOAc, 2:5, RF=0.25). 340 mg of product was obtained (isolated yield 30%).

Result of analysis by $^1$H NMR (400 MHz, DMSO) δ 8.98 (s, 1H), 8.59 (s, 1H), 7.71 (d, J=8.8 Hz, 2H), 7.59 (d, J=8.9 Hz, 2H), 7.34 (d, J=9.0 Hz, 2H), 7.20 (s, 2H), 6.91-6.81 (m, 3H), 3.91 (t, J=6.4 Hz, 2H), 2.96 (dd, J=12.9, 6.7 Hz, 2H), 1.71-1.61 (m, 2H), 1.51 (dt, J=13.1, 6.5 Hz, 2H), 1.37 (s, 9H).

Result of analysis by $^{13}C$ NMR (101 MHz, DMSO) δ 155.37 (s), 154.02 (s), 152.16 (s), 142.99 (s), 136.40 (s), 132.04 (s), 126.61 (s), 120.14 (s), 117.12 (s), 114.50 (s), 77.06 (s), 67.05 (s), 40.35 (overlap with solvent peak) 27.77 (s), 26.85 (s), 25.73 (s).

Result of analysis by MS (ESI+): calculated mass of $C_{22}H_3O_6N_4S$ [MNa]$^+$501.17; detected mass 501.2.

Preparation of 4-(4-(3-(4-sulfamoylphenyl)ureido)phenoxy)butan-1-aminium 2,2,2-trifluoroacetate, (compound 12): 500 mg of compound 11 was dissolved in 1 ml of TFA and was sonicated and stirred alternately for 15 minutes. TFA was then removed by flow of nitrogen and the product was used in further steps without any characterization or purification.

Preparation of 2,5-dioxopyrrolidin-1-yl 19-oxo-24-(4-(3-(4-sulfamoylphenyl)ureido)phenoxy)-4,7,10,13,16-pentaoxa-20-azatetracosan-1-oate (compound 13): 33 mg (1 eq, 67 μmot) of compound 12 was added slowly (during 1 hour) into a solution of bisNHS-PEG5 (36 mg, 1 eq, 67 μmob Broadpharm) and DIEA (22 μl, 2.5 eq, 168 μmot) in DMF (1 ml). The reaction mixture was left for 3 hours stirring and then the volatiles were evaporated. The final product was purified by preparative HPLC (gradient: 15-50% (vol./vol.) ACN in 40 minutes, RT 30 minutes). 15 mg of product were isolated with purity well above 99% (yield 28%). Analytical HPLC RT=18.7 min.

Result of analysis by HRMS (ESI+): calculated mass of $C_{35}H_{50}O_{14}N_5S$ [MH]+795.30695, detected mass 796.30678.

Preparation of 18-oxo-23-(4-(3-(4-sulfamoylphenyl)ureido)phenoxy)-3,6,9,12,15-pentaoxa-19-azatri-cosan-1-aminium 2,2,2-trifluoroacetate (compound 14): 46 mg (1 eq, 112 μmot) of Boc-PEG5-COOH was dissolved in 0.5 ml of DMF along with 36 mg (1 eq, 112 μmot) of TBTU and 49 μl (2.5 eq, 279 μmot) of DIEA. To this solution 55 mg (1 eq, 112 μmot) of compound 12 was added and the mixture was stirred overnight. The solvent was then evaporated and the crude product dissolved in 10 ml of EtOAc. The organic phase was washed two times by saturated bicarbonate, two times by 10% (wt./vol.) KHSO$_4$, dried and evaporated; 53 mg of product were isolated. 1 ml of TFA was added and the mixture was alternately sonicated and stirred for 15 minutes. The TFA was then removed by flow of nitrogen and the product was purified by preparative HPLC (gradient: 10-50% ACN in 40 minutes, RT=22 minutes). 17 mg of product were isolated (yield 31%). Analytical HPLC RT=16.5 min. Result of analysis by HRMS (ESI+): calculated mass of $C_{30}H_{48}O_{10}N_5S$ [MH]$^+$670.31164; detected mass 670.31164.

3b: Preparation of Detection Probe for Selective Binding of Carbonic Anhydrases Detection probe for selectively binding of carbonic anhydrases was prepared by reacting the iqPCR_amino oligonucleotide and Compound 13 in the modification buffer: 2 μl of 1 mol·l$^{-1}$ HEPES aqueous solution at pH 8.0 were first added to 10 μl of the oligonucleotide in the modification buffer (8.2 nmol, 1 eq.). After stirring, 8.2 μl of a solution of Compound 13 at a concentration of 50 mmol·l$^{-1}$ in anhydrous DMSO (410 mmol, 50 eq.) was added and stirred again. Finally, 5 μl of anhydrous DMSO was added to the mixture and after stirring incubated overnight at room temperature. The mixture was then diluted in 900 μl of an aqueous solution of 0.1 mol·l$^{-1}$ HEPES, pH 8.0, and incubated another day at room temperature. The resulting detection probe (hereinafter ssCA, FIG. 13) was purified from the hydrolysis products of Compound 13 by ultrafiltration on Amicon Ultra 0.5 ml 10K, the volume of the retentate containing the probe was five times consecutively diluted tenfold in double distilled water and then five times consecutively diluted tenfold in TBS. The concentration of ssCA probe was then determined spectrophotometrically (OD 1=1744 pmol).

The ssCA sample was analysed with LC/ESI-MS on Agilent 6230 TOF LC/MS in the same manner as described in Example 1b, only 0.05% (wt./vol.) aqueous ammonium acetate solution was used as the mobile phase instead of HFIP with TEA. The result of the analysis was a major absorption peak at 260 nm with retention time 5.14 min and the corresponding weight of 17663.28, whereas the predicted molecular weight was 17663.86. The difference between measured masses of ssCA and the original iqP-CR_amino is 681.40 compared to the expected difference 680.30. The product purity was about 80%.

A complex of neutravidin with a detection probe, Neu_dsbiotCA, was prepared for use in detection of carbonic anhydrases and testing their inhibitors. First, 750 pmol of ssCA probe together with 500 pmol iqPCR_biotin was diluted in 50 μl TBS and thermally paired by the procedure described in Example 1b; 10 μl of the resulting solution was mixed with 3 μl neutravidin at a concentration of 1 mg·ml$^{-1}$ and, after mixing, incubated first for 3 hours at room temperature and then overnight on ice. Resulting Neu_dsbiotCA complex was purified by ultrafiltration on Amicon Ultra 0.5 ml 100K, the volume of the retentate containing the complex was twice consecutively tenfold diluted in TBS. The final concentration of the detection probe in the complex was determined by qPCR by comparison with a dilution series of ssPSMA standard as described in Example 1d.

3c: Detection of CA-II and Testing Inhibitors of CA-II

The purified standard of human carbonic anhydrase II was ordered from Sigma-Aldrich (cat. no. C6165). After dissolving the lyophilized protein in double-distilled water, the protein was diluted in TBS to a final concentrations of 10 ng·μl$^{-1}$ to 10 pg·μl$^{-1}$ and 10 μl of these solutions was applied to the bottom wells of a 96-well plate FrameStar 480/96; 10 μl of pure TBS was applied for controls. After incubation for 40 minutes at room temperature, the content of the wells was tapped out and the wells were washed three times with 200 μl of TBS. Then, 100 μl of casein blocking agent five times diluted in TBS was applied to the bottom of the wells and incubated for 2 hours at room temperature. Content of the wells was subsequently tapped out and the wells were washed three times with 200 μl TBST. 10 μl of a solution of the detection Neu_dsbiotCA probe at a concentration 1 nmol·l$^{-1}$ of was added in a solution of 20 mmol·l$^{-1}$ Tris, 200 mmol·l$^{-1}$ NaCl and 0.05% Tween 20 (vol./vol.) pH=7.4 (hereinafter TBST200 buffer) with the addition of casein blocker diluted thousand fold in sum. Further procedure was the same as in Example 2d.

The procedure described could detect both 100 ng of protein CA-II ($\Delta C_q$ compared to zero control=9 cycles) and 10 ng ($\Delta C_q$ compared to zero control=5 cycles). It was also found that the addition of DMSO to a final concentration of 1% (vol./vol.) in the solution of the applied detection probe did not alter the selective binding of the probe to the immobilized protein CA-II, or non-selective binding to the surface in the zero control. Finally, 12 different known inhibitors of CA-II at a final concentration of 100 nmol·l$^{-1}$ were individually added to the solution of detection probe applied to the wells. This qualitatively verified that all 12 substances inhibit CA-II, i.e. that for all inhibitors tested, there was an observable decrease in bound detection probe.

3d: Detection of CA-IX and Testing CA-IX Inhibitors

10 µl of a solution of purified antibody M75 (Zavada et al. 2000, British Journal of Cancer, p. 1808) was applied to the bottom of the wells of a 96-well plate FrameStar 480/96 at a concentration of 10 ng·µl$^{-1}$ in TBS and incubated at room temperature for 75 minutes. Content of the wells was then tapped out and the wells were washed three times with 200 µl of TBS. 100 µl of casein blocking agent five times diluted in TBS was then applied to the bottom of the wells and incubated for 2 hours at room temperature, then the content of the wells was tapped out and the wells were washed three times with 200 µl of TBST. Subsequently, 10 µl of a solution of purified carbonic anhydrase IX in various concentrations in TBST200 was added to the bottom of the wells. The construct containing the catalytic domain and the PG domain of carbonic anhydrase IX (amino acids 55 to 390, further referred to as CA-IX PG) was prepared by recombinant expression in insect S2 cells and purified as described in (Mader, 2010 Doctoral Thesis, Charles University Prague). After two hours incubation at room temperature, the content of the wells was tapped out and the wells were washed three times with 200 µl TBST. Then 10 µl of a solution of Neu_dsbiotCA detection probe at various concentrations in TBST200 was added with casein blocker at a resulting two thousand fold dilution. Further procedure was the same as in Example 2d.

With the described procedure, after application of 1 ng CA-IX PG into the well, the amount of bound detection probe depending on its concentration was measured, and it was found that the dissociation constant of the probe is significantly higher than the highest used concentration of the probe, i.e. 50 nmol·l$^{-1}$. Further, at the concentrations of the detection probe 5 nmol·l$^{-1}$, the difference in the measured $C_q$ in wells with zero control and in the wells with 1 ng CA IX PG was approximately ten cycles, which corresponds to a difference of more than two orders of magnitude in the amount of bound probe. Dynamic range of the determination of CA-IX PG was 50 pg to 1 ng under the same conditions, see Table 13. In the same manner, it was verified that the addition of DMSO to the solution of detection probe at concentrations of 0.1% to 10% (vol./vol.) does not affect the selective or non-selective binding of the probe.

TABLE 13

| Dynamic range of CA-IX PG determination | | |
|---|---|---|
| Amount in ng | $C_q$ (1) | $C_q$ (2) |
| 10 | 10.32 | 10.21 |
| 3.2 | 9.95 | 10.03 |
| 1.0 | 10.61 | 10.33 |
| 0.50 | 11.40 | 11.25 |
| 0.25 | 12.31 | 12.26 |
| 0.10 | 15.69 | 15.51 |
| 0.05 | 18.71 | 18.24 |
| 0.025 | 18.10 | 19.74 |

TABLE 13-continued

| Dynamic range of CA-IX PG determination | | |
|---|---|---|
| Amount in ng | $C_q$ (1) | $C_q$ (2) |
| 0.010 | 20.35 | 19.86 |
| 0.005 | 20.55 | 20.36 |
| 0 | 20.92 | 20.70 |

Figure 16:
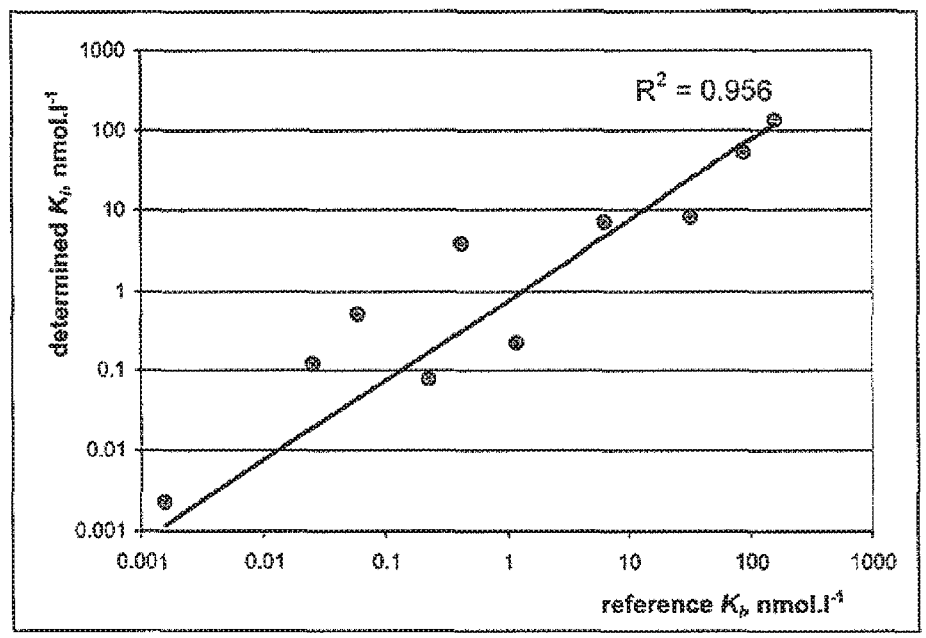
FIG. 16 shows a correlation of the inhibition constants $K_i$ of various substances towards carbonic anhydrase IX measured according to the invention (y-axis) and with reference enzyme kinetics (x-axis). For greater clarity, both axes are in a logarithmic scale.

Finally, various concentrations of a total of 12 different CA-IX inhibitors (the same substances as tested for CA-II above) were added to the solution of the detection probe applied to the wells and with the procedure described in Example 1i, their inhibition constants were determined. Only values of active sites occupancy in the range of 40 to 99.5% and the corresponding concentrations of inhibitor were used for calculations. For qualitative information about the ability of the tested substances to inhibit CA-IX, testing a single high concentration of the substance (100 nmol·l$^{-1}$) was sufficient. For quantitative information, due to the dynamic range of the setting (two to three orders of magnitude), it was necessary to test a tenfold dilution series of concentrations, whereby the measured $K_i$ value was practically identical always in two to three consecutive dilutions of the inhibitor. Obtained $K_i$ values were then compared with reference $K_i$ref values obtained from enzyme kinetics. The values obtained by the two methods are summarized in Table 14; enzyme kinetics also determined the $K_i$ref compound 13, i.e. the ligand part of the detection probe alone, to be approximately 400 nmol·l$^{-1}$. As evident from the table and a graphic comparison of the results of both methods in FIG. 16, the values determined by both methods correlated very well and even agreed in absolute values; the reliability value $R^2$ of the linear correlation between the $K_i$ determined by the method disclosed herein and $K_i$ref determined with the reference enzyme kinetics was 0.96. Only for a few substances, there was more significant difference observed between $K_i$ and $K_i$ref (five to tenfold); the exact reason for these differences is not clear. It could be caused both by errors in the determination of one or the other method, but also by major differences of the two determinations. First, the enzyme kinetics were measured with a CA-IX construct without PG domain that contains a large number of charged amino acids, and containing a point mutation N346D preventing N-glycosylation at that site; preparation and purification of the construct as well as the determination of $K_i$ref is described in (Brynda et al., 2013, Angewandte Chemie-International Edition, pp. 13760-13763). It can be assumed that the absence of structural domains, as well as point mutations may influence properties of carbonic anhydrase and thus lead to different results. Moreover, determination with enzyme kinetics is based on the measurement of pH changes of the reaction solution as a result of CA-IX catalysis, from the initial ten to seven, with a pH indicator. However, the pH change occurs also due to $CO_2$ saturation without any enzyme activity, so the affinity of the inhibitor at a defined pH is not measured, but rather the average affinity over the pH range of 10 to 7. By contrast, in our method, the affinity of the inhibitor (tested substance) is measured at a defined pH 7.4, which does not change during the measurement, which is very likely to be the reason for differing $K_i$ values determined.

TABLE 14

Comparison of $K_i$ of CA-IX inhibitors with the appropriate values of $K_i$ref

| Designation | $K_i$ determined, µmol·l⁻¹ | $K_i$ref, µmol·l⁻¹ |
|---|---|---|
| CB4 | 0.50 | 0.06 |
| CB5 | 0.12 | 0.026 |
| CB7 | 130 | 161 |
| CB8 | 3.6 | 0.43 |
| CB10 | 50 | 90.7 |
| CB12 | 8.1 | 32.7 |
| CB19 | 0.22 | 1.2 |
| CB20 | 0.077 | 0.23 |
| CB21 | 6.8 | 6.5 |
| CB31 | 0.0022 | 0.0016 |

3e: Detection of CA-IX and Testing of CA-IX Inhibitors Using Tight Binding Bivalent Probes Bivalent probe for CA-IX detection was prepared by reacting Compound 13 with an oligonucleotide with the sequence AAA CCT GCC AGT TGA GCA TTT TT A TCT GCC ACC TTC TCC ACC AGA CAA AAG CTG GAA A (SEQ ID NO: 7) containing the 3'-terminal 6-amino-2-(hydroxymethyl) hexyl phosphate modification and the 5'-terminal 6-aminohexyl phosphate modification (custom synthesis Generi-Biotech, OPC purification). The preparation, purification and LC/MS analysis was identical to the procedure described in Example 3b. The measured weight of the original oligonucleotide was 18100.85, while the weight of the oligonucleotide after reaction with Compound 13 (hereinafter ssCAbis) was 19462.36, corresponding weight difference of 1361.50 which corresponds to twice the mass of the attached Compound 13 (680.30).

Following the procedure described in the preceding examples, approximately 80 pg of CA-IX contained in a cell lysate of line HT-29 (used amount of total protein determined by Bradford assay was 1 µg) was immobilized using the M75 antibody. The immobilized CA-IX was subsequently incubated with various concentrations of ssCAbis detection probe diluted in HEPESTC' buffer (concentration range 10 pmol·l⁻¹ to 100 nmol·l⁻¹) and $K_d$ of the probe was determined as 2.1 nmol·l⁻¹ (+−0.3 nmol·l⁻¹) which is more than twenty times improvement compared to the affinity of monovalent probe (a probe containing only one molecule of Compound 13). The same procedure was repeated with the CA-IX immobilized from 1 µl of blood serum, and the $K_d$ measured was almost identical (2.2 nmol·l⁻¹+−0.3 nmol·l⁻¹).

Figure 17:
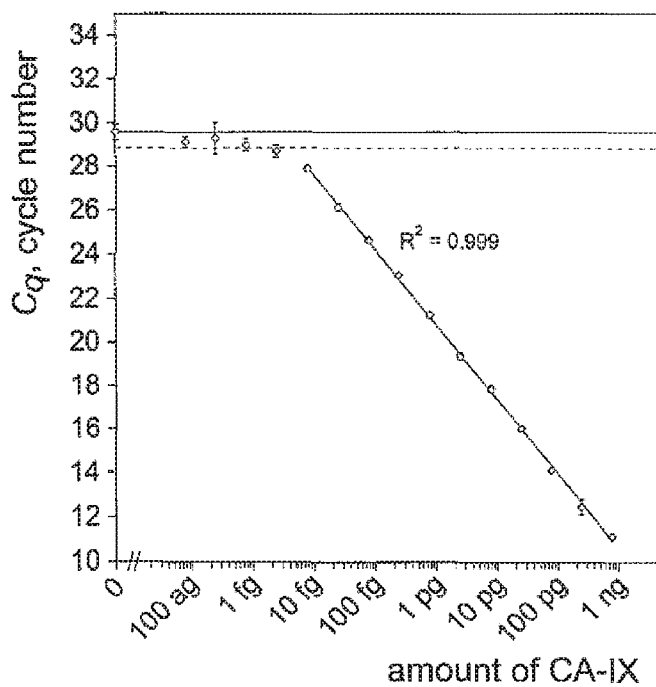
FIG. 17 shows the dependence of the measured $C_q$ values (y-axis) on the amount of CA-IX in cell lysate (line HT-29, x-axis) using a bivalent probe ssCAbis. The horizontal line shows the signal corresponding to the zero concentration of CA-IX, while the dashed line shows the signal at zero CA-IX concentration with two standard deviations of the measurement signal added, which corresponds to the limit of CA-IX detection (the lowest detected amount of CA-IX was 2.5 fg at $C_q$ 28.70).

To determine the detection limit and dynamic range of the assay, a standard was prepared (cell lysate of line HT-29) in which the concentration of CA-IX was determined using a commercial ELISA kit from RnD Systems. The dilution series of this standard was then incubated for 3 hours in wells with immobilized M75 antibody and after washing, ssCAbis detection probe diluted to a concentration of 200 pmol·l⁻¹ in HEPESTC' buffer was added to the wells for 1 hour, and after subsequent washing, the quantity of bound probe was determined using qPCR. As shown in FIG. 17, the linear range of the assay was between 8 fg and 800 pg of CA-IX, and the lowest detected amount was 2.5 fg.

Figure 18:
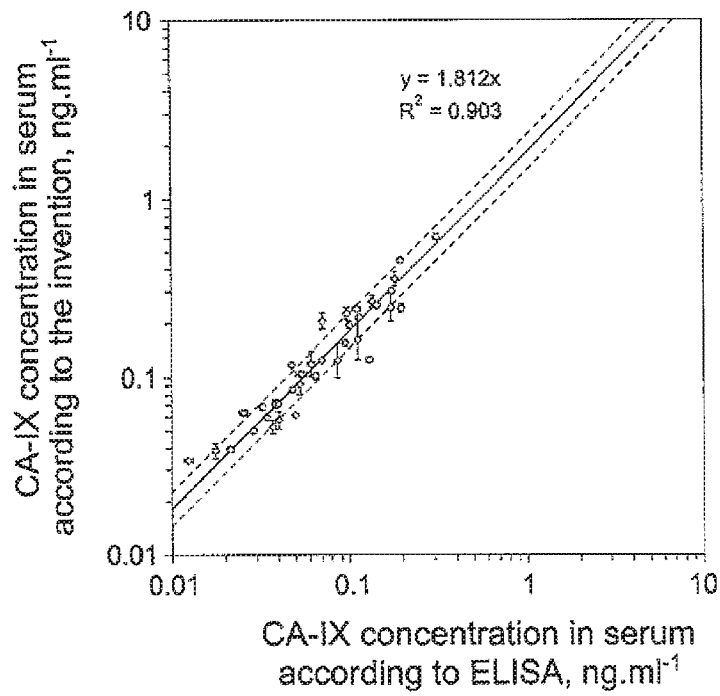
FIG. 18 shows comparison of concentrations of CA-IX measured in the blood of 36 volunteers by a method according to the invention, using the bivalent probes ssCAbis (y-axis), or by a commercial ELISA kit (RnD Systems, x-axis). The solid line represents a linear regression of logarithmically transformed concentrations; dashed lines show the values 1.25 times higher or lower than the linear regression. Error bars correspond to the standard deviation of duplicates.

The concentration of CA-IX in blood serum samples taken from 36 subjects: 12 healthy males; 10 males and 2 females with histologically confirmed renal clear cell carcinoma; and 12 males with histologically confirmed prostate cancer, was determined with the same procedure. Amount of CA-IX was determined in 10 µl of undiluted serum, which was incubated in wells with immobilized M75 antibody for 21 hours. The concentrations of CA-IX in the samples were determined by comparing the amount of bound probe with a dilution series of the standard as described in the previous paragraph, and ranged from 0.1 to 1.5 ng·ml⁻¹. To verify the obtained data, all samples were incubated with the probe also in the presence of a competitive CA-IX inhibitor acetazolamide (AAZ); it was confirmed that the binding of the probe is suppressed by adding AAZ, and the strength of inhibition of the probe binding corresponded to the $K_i$ of acetazolamide. Adding acetazolamide suppressed probe binding to an amount corresponding to the concentration of CA-IX less than 1 pg·ml⁻¹ showing that the limit of detection is approximately 1 pg·ml⁻¹ with a consumption of 10 µl of serum (10 fg in total). For further validation of the values obtained, the concentration of CA-IX in all samples was measured also with commercially available ELISA kit from RnD Systems, and as shown in FIG. 18, the results of both methods correlated very well, only the concentrations measured our way were in absolute value by approximately 80% higher than the concentrations from the ELISA kit. Compared to the ELISA kit, our way offers several advantages: the same sensitivity at tenfold lower consumption of blood serum, about two to three orders of magnitude larger linear range and most of all the opportunity to verify the accuracy of the results by incubating CA-IX with the probe in the presence of free inhibitor.

Figure 19:
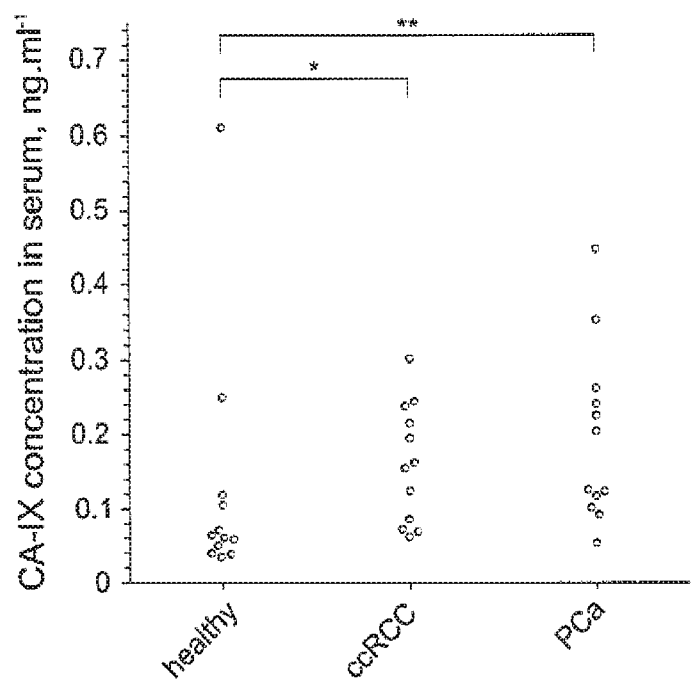
FIG. 19 shows the measured concentrations of CA-IX in the blood serum by the method according to the invention using the bivalent probe ssCAbis categorized by diagnosis of individual donors: 12 healthy males (healthy), 10 males and 2 females with histologically confirmed clear cell renal carcinoma (ccRCC) and 12 males with histologically confirmed prostate cancer (PCa). Designation * and ** shows that the measured concentrations were significantly different in both groups of patients compared to healthy persons (Mann-Whitney test, $p<0.05$).

FIG. 19 shows concentrations measured by our method divided according to groups, and it is clear that the concentration of CA-IX in the blood serum is higher both in patients with renal clear cell carcinoma and patients with prostate cancer than in the healthy (median successively 0.159; 0.162 and 0.062 ng·ml⁻¹) and the difference in both cases is statistically significant (p<0.05). Bivalent ssCAbis probe was also used to determine the inhibition constants of ten tested substances. Unpurified CA-IX contained either in the cell lysate of line HT-29 diluted in TBST' buffer (the total amount of protein in the well was 10 ng containing approximately 800 pg of CA-IX) or 10 µl of undiluted serum from a human donor (containing about 10 pg of CA-IX) was immobilized on the bottom of the wells using the M75 antibody. After washing away the unbound substances from the matrices, the immobilized CA-IX was incubated with the ssCAbis probe diluted in HEPESTC buffer with 10% DMSO to a concentration of 500 pmol·l⁻¹ and also individually with various tested substances at a concentration of either 100 nmol·l⁻¹ or 1 nmol·l⁻¹. After washing, the amount bound probe was determined with qPCR and the inhibitory constants of these substances were calculated according to the equation (16) from the difference between the amount of bound probe in wells with the tested substances and without them. The inhibitory constants were compared with $K_i$ref values obtained from enzyme kinetics with purified recombinant truncated protein (described in Brynda et al. 2013, Angewandte Chemie-International Edition, p. 13760). The values obtained are summarized in Table 15 and it is obvious that the values obtained by our method are identical to the values obtained from enzyme kinetics. The inhibitory constant of Compound 14 was determined in the same way to be 300 nmol·l⁻¹. Our method is therefore as appropriate as this reference method, but has several advantages in addition: unlike the reference method, it is not necessary to prepare recombinant CA-IX or to purify it, since only very small amounts are sufficient, contained for example in blood serum; further, due to the large linear range, it is sufficient to test only two concentrations of the tested substances, unlike the need for testing the entire dilution seres of tested substances in enzyme kinetics; and moreover, our method is suitable for HTS of CA-IX inhibitors, since the whole process takes place in a microplate layout and is automatable, which unfortunately is not the case of enzyme kinetics.

TABLE 15

Comparison of $K_i$ of CA-IX inhibitors with the corresponding $K_i$ref values

| Designation | $K_i$ref, $\mu mol \cdot l^{-1}$ | $K_i$ determined in cell lysate, $\mu mol \cdot l^{-1}$ | $K_i$ determined in blood serum, $\mu mol \cdot l^{-1}$ |
|---|---|---|---|
| AAZ | 0.025 | 0.052 | 0.018 |
| CB1 | 0.38 | 0.40 | 0.43 |
| CB7 | 160 | 14 | 8.2 |
| CB8 | 0.43 | 1.2 | 2.4 |
| CB19 | 1.1 | 0.18 | 0.10 |
| CB20 | 0.23 | 0.19 | 0.13 |
| CB2 | 5.1 | 2.1 | 0.94 |
| CB6 | 2.3 | 0.93 | 1.9 |
| CB18 | 26 | 11 | 6.2 |
| Substance 40 | 0.41 | 0.12 | 0.052 |

Example 4: Universal Detection Probe for Selective Binding to the Active Sites of Aspartic Proteases 4a: Preparation of Pepstatin NHS Ester All compounds were purified and characterized as described in example 1a.

Preparation of (21S,24S,27S,28S,32S,35S,36S)-1-((2,5-dioxopyrrolidin-1-yl)oxy)-28,36-dihydroxy-27,35-diisobutyl-21,24-diisopropyl-32-methyl-1,19,22,25,30,33-hexaoxo-4,7,10,13,16-pentaoxa-20,23,26,31,34-pentaazaoctatriacontan-38-oic acid, NHS-PEG$_5$-pepstatin (compound 15): Pepstatin was synthesized by standart amino-Fmoc synthesis on solid phase, using 2-Chlortrityl chloride resin (Iris-Biotech). The first amino acid (Fmoc-Sta-OH) was attached to the solid phase according to the manufacturer's instructions. The resin was left to react with Fmoc-Sta-OH (0.6 eq to resin substitution) in presence of 4 equivalents of DIEA for 2 hours in dichlormethane (DCM). The remaining reactive residues were quenched with mixture of DCM/MeOH/DIEA (17:2:1) for 15 minutes. All other amino acids were added using HOBUDIC method. The peptide was then cleaved from the solid phase using 95% (vol./vol.) TFA (2.5% (vol./vol.) water; 2.5% (vol./vol.) triisopropyl silane) and the crude product was used in further step without further purification (the purity after cleavage was above 95%). 18 mg (1.1 eq, 33 µmot) of bis-PEG5-NHS ester (Broadpharm) was dissolved in 0.25 ml of DMF along with 25 µl (5 eq, 165 µmot) of DIEA. 20 mg (1 eq, 30 µmot) of peptide was then added dropwise slowly to the stirring solution (during 1 hour) and the reaction was left for 3 hours. The volatiles were then evaporated and the final product was purified by preparative scale HPLC (gradient: 15-50% (vol./vol.) ACN in 40 minutes, RT=31 minutes). 10 mg of product were isolated with purity well above 99% (yield 33%). Analytical HPLC RT=19.5 min.

Result of analysis by HRMS (ESI−): calculated mass of $C_{47}H_{81}O_{18}N_6$ [M]⁻ 1017.56128; detected mass 1017.56079.

4b: Preparation of Detection Probe for Selective Binding of Aspartic Proteases

Detection probe for selective binding of aspartate proteases was prepared by reacting the iqPCR_amino oligonucleotide with compound 15 in the modification buffer: First, 4 µl of aqueous solution 1 mol·l⁻¹ HEPES pH 8.0 was added to 20 µl of the oligonucleotide in the modification buffer (16.3 nmol, 1 eq.). After stirring, 16.3 µl of compound 15 solution at a concentration of 20 mmol·l⁻¹ in anhydrous DMSO (326 nmol, 20 eq.) was added and stirred again. Finally, 15 µl of DMSO was added to the mixture and, after stirring, the mixture was incubated overnight at room temperature. The resulting detection probe (hereinafter ssAP, FIG. 13) was purified from the hydrolysis products of Compound 15 by ultrafiltration on Amicon Ultra 0.5 ml 10K, reaction mixture was diluted before application to the column to 1 ml of double distilled water and the volume of the retentate containing the probe was then ten times consecutively tenfold diluted in double distilled water during ultrafiltration. The concentration of ssAP probe was determined spectrophotometrically (OD 1=1744 pmol). The ssAP sample was analysed by LC/ESI-MS on Agilent 6230 TOF LC/MS in the same manner as described in Example 3b, only the gradient of ACN was 5-60% (vol./vol.) in 6 minutes. The result of analysis was a major absorption peak at 260 nm with retention time 4.54 min and the corresponding weight of 17887.10 (predicted molecular weight was 17887.20). The difference between the measured weight of ssAP and the original iqPCR_amino was 905.23, compared to the expected difference 904.20. Purity of the product was more than 95%.

4c: Determination of the Inhibitory Potency of the Prepared Detection Probe for Human Cathepsin D Inhibitory potency of the ssAP detection probe to human cathepsin D was determined by enzyme kinetics. The procedure was similar to that described in (Masa et al. 2006, Biochemistry, p. 15474), cathepsin D was prepared according to the procedure in (Fusek et al. 1992, Journal of Molecular Biology, p. 555). Wells of a white 96-well plate with a conical bottom (NUNC V96) were successively loaded with 93.5 µl of acetate buffer pH 4.0 (100 mmol·l⁻¹ $CH_3COONa$ and 300 mmol·l⁻¹ NaCl), 0.5 µl of cathepsin D solution and 1 µl of detection probe solution of known concentration. Just before the measurement, 5 µl of a solution of the fluorogenic substrate (Abz-Lys-Pro-Ala-Glu-Phe-Nph-Ala-Leu; Abz, aminobenzoic acid; Nph, 4-nitrophenyl-alanine) at a concentration of 40 nmol·l⁻¹ in 2% (vol./vol.) DMSO was added and cleavage rate of the substrate was then observed using a Tecan infinite M1000 reader (excitation at 330 nm and emission 410 nm). The $IC_{50}$ value was determined to be around 1 nmol·l⁻¹ from the dependence of $v_i/v_0$ ratio on the concentration of the detection probe. Such affinity of the probe is sufficient for very sensitive detection of cathepsin D.

Example 5: Detection Probe for Selective Binding to the Active Sites of Influenza Neuraminidases 5a: Preparation of a Selective Inhibitor of Influenza Neuraminidases with Attached Azide Group Compound 17; 1-(6-Azidohexyl)-1-methyl-(3R,4R,5S)-4-acetylamino-5-N-tert-butoxycarbonyl-amino-3-(1-ethyl-propoxy)-1-cyclohexene-1-phosphonate; was prepared analogously to the procedure described in (Carbain 2010, Doctoral thesis, University of Sussex).

Preparation of Compound 18; 1-(6-Azidohexyl)-(3R,4R,5S)-4-acetylamino-5-N-tert-butoxycarbonyl-amino-3-(1-ethylpropoxy)-1-cyclohexene-1-phosphonate: a mixture of diastereomers of Compound 17 (0.068 g, 0.12 mmol) was dissolved in 4 ml of dry THF and thiophenol (0.05 ml, 0.66 mmol) and triethylamine (0.15 ml; 1.08 mmol) were added to this solution. The reaction mixture was stirred at room temperature for two days, then thiophenol (0.05 ml, 0.66 mmol) and triethylamine (0.15 ml; 1.08 mmol) were again added. The next day, the reaction mixture was concentrated on a rotary evaporator and separated by column chromatography (silica gel; eluent ethyl acetate:methanol/3:1 to 1:2). Yield: 0.042 g of the demethylated product.

Result of analysis by HRMS (ESI−): calculated mass of $C_{24}H_{43}O_7N_5P$ 544.2906; detected 544.2902. Preparation of Compound 19; 1-(6-Azidohexyl)-(3R,4R,5S)-4-acetylamino-5-amino-3-(1-ethylpropoxy)-1-cyclohexene-1-phosphonate: Compound 18 (0.04 g; 0.073 mmol) was dissolved in 3 ml of trifluoroacetic acid and after stirring for two hours at room temperature, the reaction mixture was evaporated and the residue was purified by preparative HPLC on a reverse column (stationary phase C-18 modified silica gel; mobile phase: acetonitrile/water with 0.1% (vol./vol.) trifluoroacetic acid). Yield: 0.02 g of the final product.

Result of analysis by HRMS (ESI+): calculated mass of $C_{19}H_{37}O_5N_5P$ 446.2527; detected 446.2527.

5b: Preparation of Detection Probe for Influenza Neuraminidases

Preparation of oligonucleotide with dibenzylcyclooctyne group (hereinafter ssAD): 50 μl of 2× concentrated modification buffer was first added to the iqPCR_amino oligonucleotide (20.2 nmol; 1 eq) dissolved in 48 μl of double distilled water. 50.4 μl of dibenzylcyclooctyne NHS-ester (Sigma, cat. no. 761524) at a concentration of 20 mmol·l$^{-1}$ (1.008 μmol, 50 eq) in anhydrous DMSO was added and stirred. As precipitation was observed, an additional 70 μl of DMSO was subsequently added and stirred. After incubation for two days at room temperature, the resulting modified oligonucleotide (ssAD) was purified by ultrafiltration on Amicon Ultra 0.5 ml 10K column; the reaction mixture was diluted to 1 ml in double distilled water prior to application onto the column and then the retentate volume was ten times successively tenfold diluted in double distilled water during the ultrafiltration. Oligonucleotide concentration in the retentate was determined spectrophotometrically (OD 1=1744 pmol). A sample of the product was analysed by LC/ESI-MS on Agilent 6230 TOF LC/MS as described in Example 4b. Analysis resulted in an absorption peak at 260 nm with retention time 4.47 min corresponding to weight 17269.75. The weight of original iqPCR_amino was not found, suggesting complete conversion of the reaction. The difference between the measured weight of ssAD and the original iqPCR_amino was 278.88 compared to the expected difference of 287.40.

Figure 13:
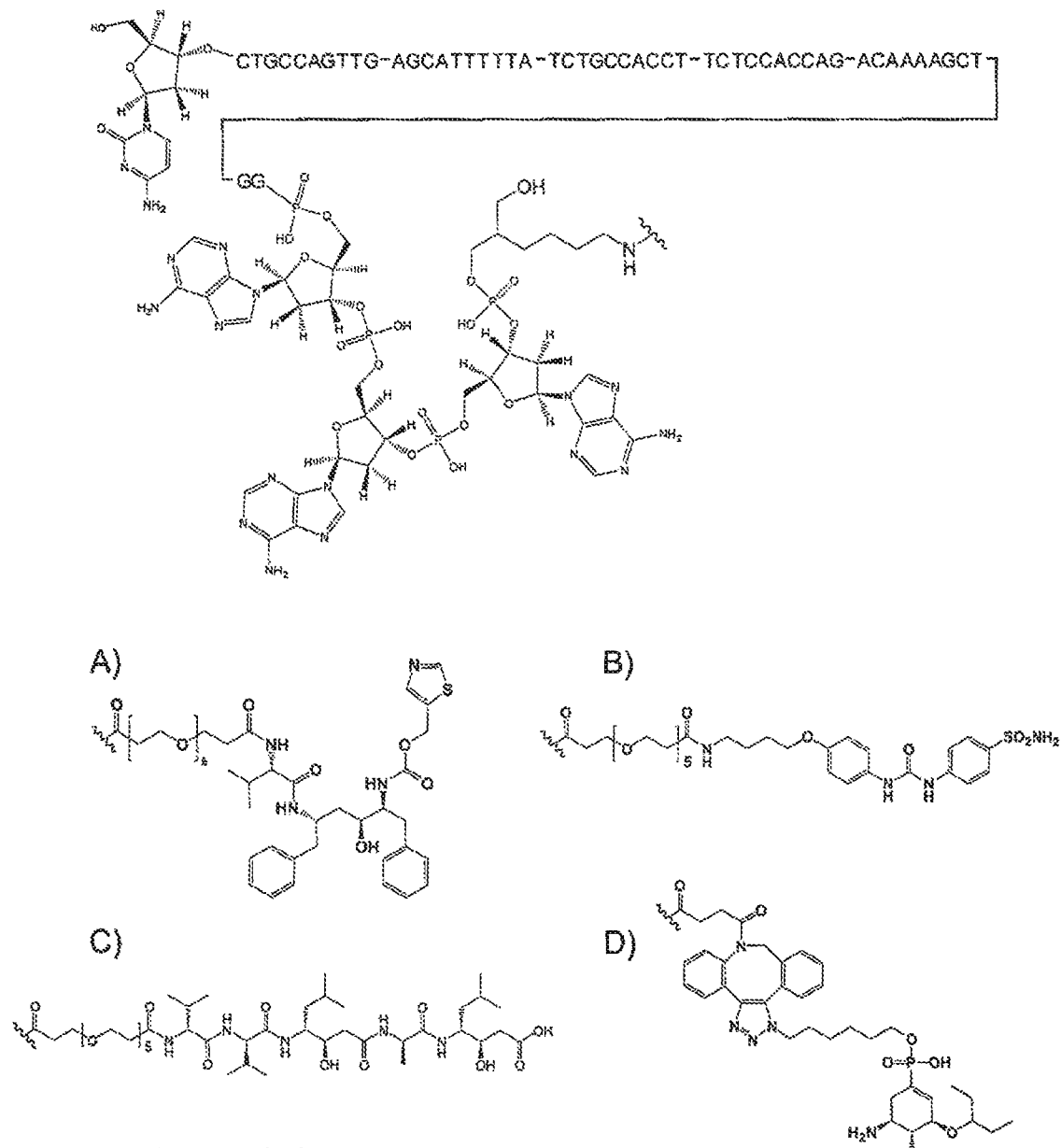
FIG. 13 shows the structure of the prepared detection probes for selective binding of analytes. The nucleotides within the oligonucleotide sequence are listed using a single letter code:
A) A detection probe with a compound for selective binding of HIV protease (ssHIV1)
B) A detection probe with a compound for selective binding of carbonic anhydrases (ssCA)
C) A detection probe with a compound for selective binding of aspartic proteases (ssAP)
D) A detection probe with a compound for selective binding of influenza neuraminidases (ssAD_NA).

Preparation of detection probe for influenza neuraminidases (hereinafter ssAD_NA; FIG. 13): 8.8 μl of 2× concentrated modification buffer was first added to the ssAD oligonucleotide (3.0 nmol; 1 eq) dissolved in 7.3 ml of double distilled water. After stirring, 1.5 μl of a solution of Compound 19 at a concentration of 20 mmol·l$^{-1}$ (30 nmol; 10 eq) in anhydrous DMSO was added and stirred again. After three days incubation at room temperature, the resulting detection probe ssAD_NA was purified by ultrafiltration on Amicon Ultra 0.5 ml 10K column; the reaction mixture was diluted to 1 ml in double distilled water prior to application onto the column and then the retentate volume was ten times successively tenfold diluted in double distilled water during the ultrafiltration. Probe concentration in the retentate was determined spectrophotometrically (OD 1=1744 pmol). A sample of the probe was analysed by LC/ESI-MS on Agilent 6230 TOF LC/MS as described in Example 4b. Analysis revealed an absorption peak at 260 nm with retention time of 4.73 min corresponding to weight of 17715.25. The weight of original ssAD was not found, suggesting complete conversion of the reaction. The difference between the measured weight of ssAD_NA and the original ssAD was 445.50 compared to the expected difference of 445.50.

5c: Determination of Inhibition Constant of the Prepared Detection Probe

The tested neuraminidase type N1 came from the pandemic virus A/California/07/2009 (GenBank CY121682). The coding sequence of the catalytic domain (amino acids 82-469) was synthesized by Genscript company, cloned into pMT BiP vector, the resulting construct contained (in addition to the signal peptide) an N-terminal Avi-tag and thrombin cleavage site for cleavage of the tag. Neuraminidase was expressed in insect S2 cells, the secreted protein was purified from SF900 medium (commercially available media from Invitrogen, USA) by precipitation with ammonium sulphate. The soluble fraction resulting from 50 percent sulphate saturation was dialyzed into 50 $mmol \cdot l^{-1}$ Tris, 150 $mmol \cdot l^{-1}$ NaCl pH 8.0; concentrated and separated by gel permeation chromatography on a Superdex 200 column. Fractions with neuraminidase catalytic activity were combined, a solution of calcium chloride to a final concentration of 10 $mmol \cdot l^{-1}$ and Thrombin-Agarose (Sigma-Aldrich, USA) were added and incubated for 12 hours at 4° C. This mixture was then divided by gel permeation chromatography on Superdex 75 column. Fractions containing the active neuraminidase without Avi-tag (determined by SDS polyacrylamide electrophoresis and Western blotting) were frozen for kinetic experiments.

Enzyme activity of neuraminidase was measured with a fluorimetric assay using a fluorescent substrate 2'-(4-methylumbelliferyl)-α-D-N-acetylneuraminic acid (4-MUNANA) in 100 $mmol \cdot l^{-1}$ MES, 150 $mmol \cdot l^{-1}$ NaCl, 10 $mmol \cdot l^{-1}$ $CaCl_2$ at pH 6.15. Final concentrations in the reaction mixture were: 16 $nmol \cdot l^{-1}$ neuraminidase, 500 $nmol \cdot l^{-1}$ 4-MUNANA substrate (at $K_M$=1.1 $mmol \cdot l^{-1}$) and 2% DMSO (vol./vol.). Cleavage of substrate was monitored at excitation and emission wavelengths $\lambda_{exc}$=365 nm and $\lambda_{em}$=450 nm on a Tecan Infinite M1000 reader, the reaction was incubated for 20 minutes at 37° C. and then quenched by addition of sodium carbonate solution to a final concentration of 0.5 $mol \cdot l^{-1}$. Values of apparent $K_i'$ and $K_i$ were obtained by evaluating the ratio of the inhibited and uninhibited reaction rates $v_i/v_0$ according to Williams and Morrison. Measured $K_i$ of clinically used Oseltamivir was 24 $nmol \cdot l^{-1}$ (±4 $nmol \cdot l^{-1}$), $K_i$ of Compound 19 was 24 $nmol \cdot l^{-1}$ (±5 $nmol \cdot l^{-1}$) and $K_i$ of the ssAD_NA detection probe was 0.79 $nmol \cdot l^{-1}$ (±0.09 $nmol \cdot l^{-1}$). Apparent $K_i$ for the Compound 19 and the detection probe ssAD_NA was also determined at physiological pH 7.4 in 100 $mmol \cdot l^{-1}$ Tris, 150 $mmol \cdot l^{-1}$ NaCl, 10 $mmol \cdot l^{-1}$ $CaCl_2$; $K_i$ of Compound 19 was approximately 40 $nmol \cdot l^{-1}$, while of the ssAD_NA probe approximately 2 $nmol \cdot l^{-1}$. Connecting the oligonucleotide to the compound 19 thus resulted in a substance having at least twenty-fold higher affinity for neuraminidase compared to both Compound 19 and Oseltamivir.

5d: Testing the Inhibitory Potency of Substances Against Influenza Neuraminidase N1

Following the procedure described in the previous examples, 1 ng of purified recombinant neuraminidase N1, containing an N-terminal strep-tag, diluted in TBST buffer with thousand-fold diluted casein blocker and $CaCl_2$ at a concentration of 5 mmol·l$^{-1}$ was immobilized to the bottom of wells of a PCR plate using an antibody recognizing the strep-tag. The immobilized neuraminidase was subsequently incubated in the same buffer with the ssAD_NA detection probe at a concentration of 250 pmol·l$^{-1}$ and also with various concentrations of several different tested substances in the range of 100 nmol·l$^{-1}$ to 1 mmol·l$^{-1}$ and after washing, the amount of bound probe was determined by qPCR. From the $\Delta C_q$ difference between wells with tested substances and wells with the detection probe itself, inhibitory constants $K_i$ of the tested substances were calculated based on equation (15) and the used concentrations of the tested substances. $K_i$ was determined 48 nmol·l$^{-1}$ for oseltamivir (reference value by enzyme kinetics as described in the previous section was 24 nmol·l$^{-1}$), for the Compound 19 it was 138 nmol·l$^{-1}$ (24 nmol·l$^{-1}$) and for other substances: for Substance 41, 85 nmol·l$^{-1}$ (26 nmol·l$^{-1}$); for Substance 42, 159 nmol·l$^{-1}$ (39 nmol·l$^{-1}$); for Substance 43, 6100 nmol·l$^{-1}$ (2100 nmol·l$^{-1}$); and for Substance 44, 38100 nmol·l$^{-1}$ (12700 nmol·l$^{-1}$). Measured values correlate very well with those obtained by enzyme kinetics reported in brackets ($R^2$=1).

INDUSTRIAL APPLICABILITY

The described method has broad application in medicine. Given the exceptional sensitivity in the order of only several tens of molecules, it offers the possibility of determining the protein markers in blood in concentrations unmeasurable so far (e.g., PSA after prostate surgery).

Furthermore, due to the probe binding to the active site of the analyte, it is possible to measure bond strength of other tested substances to the same active site. In combination with the large dynamic range, our assay allows to determine the value of inhibition constants of the tested substances from only one measurement and using a single concentration of tested substance. Due to the high sensitivity and selectivity of the method, a minimum amount of an analyte contained in a biological matrix, e.g. blood or a cell or tissue lysate, is sufficient.

The invention claimed is:

1. A method for detecting an analyte in a sample said method comprising the steps of:
   a) immobilizing the analyte on the surface of a solid carrier;
   b) incubating the solid carrier with
      a detection probe, wherein the detection probe consists of:
      (i) a compound capable of selectively binding to the analyte active site,
         said compound having a molecular weight of up to 2500 Da,
      (ii) an oligonucleotide tag, and
      (iii) a chemical linker covalently linking the compound and the oligonucleotide tag;
   c) washing the solid carrier to remove unbound detection probe; and
   d) measuring the amount of the bound detection probe directly on the solid carrier,
   thereby detecting the analyte;
   wherein the amount of the analyte in the sample is proportional to the amount of the bound detection probe.

2. The method according to claim 1, wherein the immobilizing in step (a) or the incubating in step (b) further comprises an additive selected from the group consisting of ionic detergents, nonionic detergents, casein and therefrom prepared casein blocking agents, serum albumin, DNA, and immunoglobulins.

3. A method for detecting an analyte in a sample, said method comprising the steps of:
   a) incubating the analyte with a detection probe, wherein the detection probe consists of:
      (i) a compound capable of selectively binding to the analyte active site, said compound having a molecular weight of up to 2500 Da,
      (ii) an oligonucleotide tag, and
      (iii) a chemical linker covalently linking the compound and the oligonucleotide tag;
   b) immobilizing the analyte on the surface of a solid carrier;
   c) washing the solid carrier to remove unbound detection probe; and
   d) determining the amount of the bound detection probe on the solid carrier, thereby detecting the analyte;
   wherein the amount of the analyte in the sample is proportional to the amount of the bound detection probe.

4. The method according to claim 1, wherein:
   (a) the analyte is an enzyme and the compound is an inhibitor of the enzyme,
   (b) the analyte is a receptor and the compound is an agonist or antagonist of the receptor, or
   (c) the analyte is a transporter;
   and the oligonucleotide tag is a single stranded or a double stranded DNA.

5. The method according to claim 1, wherein the detection probe contains two or more of the compound, wherein said compound is each covalently linked via the chemical linker to the oligonucleotide tag.

6. The method according to claim 1, wherein our detection probes are each attached via a biotin to an avidin, neutravidin or streptavidin.

7. The method according to claim 1, comprising determining the amount of bound detection probe by a method selected from the group consisting of quantitative polymerase chain reaction and coupled enzyme reactions by fluorescence, spectrophotometry or chemiluminescence.

8. The method according to claim 1, further comprising, prior to step (a), immobilizing on the surface of the solid carrier a binding molecule capable of selectively binding to the analyte, wherein the binding molecule is selected from the group consisting of antibodies or fragments thereof; protein molecules mimicking antibodies; affibodies; anticalins; designed ankyrin repeat proteins; lectins; avidin; neutravidin; streptavidin; oligopeptides; and chelating agents.

9. The method according to claim 8, wherein in step (a), the binding molecule immobilizes the analyte on the surface of the solid carrier through a hapten, a biotin, a universal epitope, an affinity tag, or a purification tag.

10. The method according to claim 1, wherein the sample is selected from the group consisting of blood; blood plasma; blood serum; cerebrospinal fluid; urine; bacterial, yeast, tissue or cell lysate; conditioned bacterial, yeast or cell culture medium; synovial fluid; amniotic fluid; ascites; pleural fluid; pericardial fluid; stool extract; saliva; sweat; and seminal plasma.

11. The method according to claim 1, wherein:
    (a) the analyte is a human prostate specific membrane antigen and the compound is an inhibitor of human prostate specific membrane antigen; or
    (b) the analyte is human glutamate carboxypeptidase III and the compound is an inhibitor of human glutamate carboxypeptidase III.

12. The method according to claim 1, wherein the analyte is human prostate specific antigen and the compound for binding is selective inhibitor of human prostate specific antigen.

13. The method according to claim 1, wherein:
    (a) the analyte is human carbonic anhydrase IX and the compound is an inhibitor of human carbonic anhydrase IX; or
    (b) the analyte is human carbonic anhydrase XII and the compound is an inhibitor of human carbonic anhydrase XII.

14. The method according to claim 1, wherein the analyte is influenza neuraminidase and the compound is an inhibitor of influenza neuraminidase.

15. The method according to claim 1, wherein:
    (a) the analyte is human fibroblast-activating protein and the compound is an inhibitor of human fibroblast-activating protein; or
    (b) the analyte is human dipeptidyl peptidase 4 and the compound is an inhibitor of the human dipeptidyl peptidase 4.

16. The method according to claim 1, wherein the oligonucleotide tag further comprises a covalently attached fluorophore, biotin or a reactive chemical group.

17. A method for measuring binding of a substance to an active site of an analyte, said method comprising the steps of:
    a) immobilizing the analyte on the surface of the solid carrier;
    b) incubating the solid carrier with the substance and a detection probe, wherein the detection probe consists of:
    (i) a compound capable of selectively binding to the analyte active site, said compound having a molecular weight of up to 2500 Da,
    (ii) an oligonucleotide tag, and
    (iii) a chemical linker covalently linking the compound and the oligonucleotide tag;
    c) washing the solid carrier is washed to remove unbound detection probe;
    d) measuring the amount of the bound detection probe; and
    e) comparing the amount of the bound detection probe with a control amount of the bound detection probe measured in the method in the absence of the substance, thereby measuring the binding of the substance to the active site of the analyte.

18. The method according to claim 17, wherein the oligonucleotide tag in the detection probe further comprises a covalently attached fluorophore, biotin or a reactive chemical group.

19. The method according to claim 17, wherein the amount of the bound detection probe is determined directly on the solid carrier.

20. The method according to claim 17, wherein the immobilizing in step (a) or the incubating in step (b) further comprises an additive selected from the group consisting of ionic detergents, nonionic detergents, casein and therefrom prepared casein blocking agents, serum albumin, DNA, and immunoglobulins.

21. A method for measuring binding of a substance to an active site of an analyte, said method comprising the steps of:
    a) incubating the analyte with the substance and a detection probe, wherein the detection probe consists of:
    (i) a compound capable of selectively binding to the analyte, said compound having a molecular weight of up to 2500 Da,
    (ii) an oligonucleotide tag, and
    (iii) a chemical linker covalently linking the compound and the oligonucleotide tag;
    b) immobilizing the analyte on the surface of the solid carrier;
    c) washing the solid carrier to remove unbound detection probe;
    d) measuring the amount of the bound detection probe; and
    e) comparing the amount of the bound detection probe with a control amount of the bound detection probe determined in the absence of the substance, thereby measuring the binding of the substance to the active site of the analyte.

22. The method according to claim 17, wherein:
    a) the analyte is an enzyme and the compound is an inhibitor of the enzyme,
    b) the analyte is a receptor and the compound is an agonist or antagonist of the receptor, or
    c) the analyte is a transporter;
    and the oligonucleotide tag is a single stranded or a double stranded DNA.

23. The method according to claim 17, wherein the detection probe contains two or more compounds, wherein said two or more compounds is each covalently linked via the chemical linker to the oligonucleotide tag.

24. The method according to claim 17, wherein four detection probes are attached via a biotin to an avidin, neutravidin, or streptavidin.

25. The method according to claim 17, wherein the amount of bound detection probe is determined by a method selected from the group consisting of quantitative polymerase chain reaction and coupled enzyme reactions by fluorescence, spectrophotometry, or chemiluminescence.

26. The method according to claim 17, further comprising, prior to step (a), immobilizing on the surface of the solid carrier a binding molecule capable of selectively binding to the analyte, wherein the binding molecule is selected from the group consisting of antibodies or fragments thereof; protein molecules mimicking antibodies; affibodies; anticalins; designed ankyrin repeat proteins; lectins; avidin; neutravidin; streptavidin; oligopeptides; and chelating agents.

27. The method according to claim 26, wherein in step (a), the binding molecule immobilizes the analyte on the surface of the solid carrier through a hapten, a biotin, a universal epitope, an affinity tag, or a purification tag.

28. The method according to claim 17, wherein the sample is selected from the group consisting of blood; blood plasma; blood serum; cerebrospinal fluid; urine; bacterial, yeast, tissue or cell lysate; conditioned bacterial, yeast or cell culture medium; synovial fluid; amniotic fluid; ascites; pleural fluid; pericardial fluid; stool extract; saliva; sweat; and seminal plasma.

29. The method according to claim 17, wherein the binding of the substance to the active site of the analyte is expressed as a binding constant.

30. The method according to claim 17, wherein
   (a) the analyte is a human prostate specific membrane antigen, and the compound is an inhibitor of human prostate specific membrane antigen; or
   (b) the analyte is human glutamate carboxypeptidase III and the compound is an inhibitor of human glutamate carboxypeptidase III.

31. The method according to claim 17, wherein the analyte is a human prostate specific antigen, and the compound is an inhibitor of human prostate specific antigen.

32. The method according to claim 17, wherein
   (a) the analyte is human carbonic anhydrase IX and the compound is an inhibitor of human carbonic anhydrase IX; or
   (b) the analyte is human carbonic anhydrase XII and the compound is an inhibitor of human carbonic anhydrase XII.

33. The method according to claim 17, wherein the analyte is influenza neuraminidase and the compound is an inhibitor of influenza neuraminidase.

34. The method according to claim 17, wherein
   (a) the analyte is human fibroblast-activating protein and the compound is an inhibitor of human fibroblast-activating protein; or
   (b) the analyte is human dipeptidyl peptidase 4 and the compound is an inhibitor of the human dipeptidyl peptidase 4.

35. The method according to claim 1, wherein the immobilizing in step (a) is by non-specific non-covalent adsorption,
   by covalent binding of surface functional groups of the analyte and corresponding functional groups of the solid carrier, or
   by a binding molecule bound to the surface of the solid carrier before the immobilizing, and capable of selectively binding the analyte.

36. The method according to claim 3, wherein the immobilizing in step (a) is by non-specific non-covalent adsorption,
   by covalent binding of surface functional groups of the analyte and corresponding functional groups of the solid carrier, or
   by a binding molecule bound to the surface of the solid carrier before the immobilizing, and capable of selectively binding the analyte.

37. The method according to claim 3, wherein:
   (a) the analyte is an enzyme and the compound is an inhibitor of the enzyme,
   (b) the analyte is a receptor and the compound is an agonist or antagonist of the receptor, or
   (c) the analyte is a transporter;
and the oligonucleotide tag is a single stranded or a double stranded DNA.

38. The method according to claim 3, wherein the detection probe contains two or more of the compound, wherein said compound is each covalently linked via the chemical linker to the oligonucleotide tag.

39. The method according to claim 3, wherein four detection probes are attached via a biotin to an avidin, neutravidin or streptavidin.

40. The method according to claim 3, comprising determining the amount of bound detection probe by a method selected from the group consisting of quantitative polymerase chain reaction and coupled enzyme reactions by fluorescence, spectrophotometry or chemiluminescence.

41. The method according to claim 3, further comprising, prior to step (a), immobilizing on the surface of the solid carrier a binding molecule capable of selectively binding to the analyte, wherein the binding molecule is selected from the group consisting of antibodies or fragments thereof; protein molecules mimicking antibodies; affibodies; anticalins; designed ankyrin repeat proteins; lectins; avidin; neutravidin; streptavidin; oligopeptides; and chelating agents.

42. The method according to claim 41, wherein in step (a), the binding molecule immobilizes the analyte on the surface of the solid carrier through a hapten, a biotin, a universal epitope, an affinity tag, or a purification tag.

43. The method according to claim 3, wherein the sample is selected from the group consisting of blood; blood plasma; blood serum; cerebrospinal fluid; urine; bacterial, yeast, tissue or cell lysate; conditioned bacterial, yeast or cell culture medium; synovial fluid; amniotic fluid;
   ascites; pleural fluid; pericardial fluid; stool extract; saliva; sweat; and seminal plasma.

44. The method according to claim 3, wherein the immobilizing in step (a) or the incubating in step (b) further comprises an additive selected from the group consisting of ionic detergents, nonionic detergents, casein and therefrom prepared casein blocking agents, serum albumin, DNA, and immunoglobulins.

45. The method according to claim 3, wherein the oligonucleotide tag-further comprises a covalently attached fluorophore, biotin or a reactive chemical group.

46. The method according to claim 17, wherein the immobilizing in step (a) is by non-specific non-covalent adsorption,
   by covalent binding of surface functional groups of the analyte and corresponding functional groups of the solid carrier, or
   by a binding molecule bound to the surface of the solid carrier before the immobilizing, and capable of selectively binding the analyte.

47. The method according to claim 29, wherein the binding constant is determined from the difference of the amounts of bound detection probe after incubation without the substance and after incubation with a single concentration of the substance.

48. The method according to claim 21, wherein the immobilizing in step (a) is by non-specific non-covalent adsorption,
   by covalent binding of surface functional groups of the analyte and corresponding functional groups of the solid carrier, or
   by a binding molecule bound to the surface of the solid carrier before the immobilizing, and capable of selectively binding the analyte.

49. The method according to claim 21, wherein:
   (a) the analyte is an enzyme and the compound is an inhibitor of the enzyme,
   (b) the analyte is a receptor and the compound is an agonist or antagonist of the receptor, or
   (c) the analyte is a transporter;

and the oligonucleotide tag is a single stranded or a double stranded DNA.

50. The method according to claim 21, wherein the detection probe contains two or more of the compound, wherein said compound is each covalently linked via the chemical linker to the oligonucleotide tag.

51. The method according to claim 21, wherein four detection probes are attached via a biotin to an avidin, neutravidin or streptavidin.

52. The method according to claim 21, comprising determining the amount of bound detection probe by a method selected from the group consisting of quantitative polymerase chain reaction and coupled enzyme reactions by fluorescence, spectrophotometry or chemiluminescence.

53. The method according to claim 21, further comprising, prior to step (a), immobilizing on the surface of the solid carrier a binding molecule capable of selectively binding to the analyte, wherein the binding molecule is selected from the group consisting of antibodies or fragments thereof; protein molecules mimicking antibodies; affibodies; anticalins; designed ankyrin repeat proteins; lectins; avidin; neutravidin; streptavidin; oligopeptides; and chelating agents.

54. The method according to claim 53, wherein in step (a), the binding molecule immobilizes the analyte on the surface of the solid carrier through a hapten, a biotin, a universal epitope, an affinity tag, or a purification tag.

55. The method according to claim 21, wherein the sample is selected from the group consisting of blood; blood plasma; blood serum; cerebrospinal fluid; urine; bacterial, yeast, tissue or cell lysate; conditioned bacterial, yeast or cell culture medium; synovial fluid; amniotic fluid; ascites; pleural fluid; pericardial fluid; stool extract; saliva; sweat; and seminal plasma.

56. The method according to claim 21, wherein the immobilizing in step (a) or the incubating in step (b) further comprises an additive selected from the group consisting of ionic detergents, nonionic detergents, casein and therefrom prepared casein blocking agents, serum albumin, DNA, and immunoglobulins.

57. The method according to claim 21, wherein the oligonucleotide tag further comprises a covalently attached fluorophore, biotin or a reactive chemical group.

58. The method according to claim 21, wherein the amount of the bound detection probe is determined directly on the solid carrier.

59. The method according to claim 21, wherein the binding of the substance to the active site of the analyte is expressed as a value of binding constant.

60. The method according to claim 59, wherein the binding constant is determined from the difference of the amounts of bound detection probe after incubation without the substance and after incubation with a single concentration of the substance.

\* \* \* \* \*

SEQUENCE LISTING

```
<160> NUMBER OF SEQ ID NOS: 7

<210> SEQ ID NO 1
<211> LENGTH: 55
<212> TYPE: DNA
<213> ORGANISM: Artificial
<220> FEATURE:
<223> OTHER INFORMATION: detection probe ssDNA iqPCR_amino

<400> SEQUENCE: 1
cctgccagtt gagcattttt atctgccacc ttctccacca gacaaaagct ggaaa         55

<210> SEQ ID NO 2
<211> LENGTH: 55
<212> TYPE: DNA
<213> ORGANISM: Artificial
<220> FEATURE:
<223> OTHER INFORMATION: ssDNA for dsPSMA probe

<400> SEQUENCE: 2
tttccagctt ttgtctggtg gagaaggtgg cagataaaaa tgctcaactg gcagg         55

<210> SEQ ID NO 3
<211> LENGTH: 52
<212> TYPE: DNA
<213> ORGANISM: Artificial
<220> FEATURE:
<223> OTHER INFORMATION: ssDNA for dsA3PSMA

<400> SEQUENCE: 3
ccagcttttg tctggtggag aaggtggcag ataaaaatgc tcaactggca gg            52

<210> SEQ ID NO 4
<211> LENGTH: 54
<212> TYPE: DNA
<213> ORGANISM: Artificial
<220> FEATURE:
<223> OTHER INFORMATION: ssDNA for dsbioPSMA probe - iqPCR_biotin

<400> SEQUENCE: 4
ccagcttttg tctggtggag aaggtggcag ataaaaatgc tcaactggca ggta          54

<210> SEQ ID NO 5
```

```
<211> LENGTH: 20
<212> TYPE: DNA
<213> ORGANISM: Artificial
<220> FEATURE:
<223> OTHER INFORMATION: primer

<400> SEQUENCE: 5
ccagcttttg tctggtggag                                           20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
cctgcagcca gttgattttt                                           20

<210> SEQ ID NO 7
<211> LENGTH: 58
<212> TYPE: DNA
<213> ORGANISM: Artificial
<220> FEATURE:
<223> OTHER INFORMATION: ssDNA for CA-IX probe

<400> SEQUENCE: 7
aaacctgcca gttgagcatt tttatctgcc accttctcca ccagacaaaa gctggaaa    58
```